United States Patent
Kontermann et al.

(10) Patent No.: US 10,428,120 B2
(45) Date of Patent: Oct. 1, 2019

(54) SERUM HALF-LIFE EXTENSION USING IGBD

(71) Applicant: UNIVERSITAT STUTTGART, Stuttgart (DE)

(72) Inventors: Roland Kontermann, Nurtingen (DE); Felix Unverdorben, Stuttgart (DE); Meike Hutt, Schomdorf (DE)

(73) Assignee: UNIVERSITAT STUTTGART, Stuttgart (DE)

( * ) Notice: Subject to any disclaimer, the term of this patent is extended or adjusted under 35 U.S.C. 154(b) by 0 days.

(21) Appl. No.: 15/410,363

(22) Filed: Jan. 19, 2017

(65) Prior Publication Data

US 2017/0145062 A1 May 25, 2017

Related U.S. Application Data

(63) Continuation of application No. 14/345,845, filed as application No. PCT/EP2012/068802 on Sep. 24, 2012, now abandoned.

(60) Provisional application No. 61/538,310, filed on Sep. 23, 2011.

(30) Foreign Application Priority Data

Sep. 23, 2011 (EP) .................................... 11007788

(51) Int. Cl.
| | |
|---|---|
| *C07K 14/31* | (2006.01) |
| *C07K 16/28* | (2006.01) |
| *C07K 14/315* | (2006.01) |
| *C07K 16/30* | (2006.01) |
| *A61K 39/395* | (2006.01) |

(52) U.S. Cl.
CPC ...... *C07K 14/315* (2013.01); *A61K 39/39591* (2013.01); *C07K 14/31* (2013.01); *C07K 16/2809* (2013.01); *C07K 16/2863* (2013.01); *C07K 16/2875* (2013.01); *C07K 16/3007* (2013.01); *C07K 2317/31* (2013.01); *C07K 2317/34* (2013.01); *C07K 2317/622* (2013.01); *C07K 2317/626* (2013.01); *C07K 2317/94* (2013.01); *C07K 2319/00* (2013.01); *C07K 2319/21* (2013.01); *C07K 2319/30* (2013.01); *C07K 2319/31* (2013.01)

(58) Field of Classification Search
CPC .. C07K 14/315; C07K 14/31; C07K 2317/31; C07K 2317/622; C07K 2317/626; C07K 2317/94; C07K 2317/00; C07K 2319/21; C07K 2319/30; C07K 2319/31; A61K 39/39591

See application file for complete search history.

(56) References Cited

U.S. PATENT DOCUMENTS

2009/0137416 A1 5/2009 Fandl et al.

FOREIGN PATENT DOCUMENTS

| EP | 2518078 A1 | 10/2012 |
|---|---|---|
| JP | 2007-532185 A | 11/2007 |
| WO | WO-98/01560 A1 | 1/1998 |
| WO | WO-2005097186 A2 | 10/2005 |
| WO | WO-2008052933 A2 | 5/2008 |
| WO | WO-2011074717 A1 | 6/2011 |

OTHER PUBLICATIONS

Skolnick et al., Trends in Biotechnology, vol. 18: pp. 34-39 (Year: 2000).*
Burgess et al., Journal of Cell Biology, vol. 111, pp. 2129-2138 (Year: 1999).*
Lazar et al., Molecular and Cellular Biology, vol. 8, pp. 1247-1252 (Year: 1988).*
Colman et al., in Research in Immunology (145(1):33-36 (Year: 1994).*
International Search Report in corresponding PCT/EP2012/068802 dated Nov. 14, 2012.
Kontermann et al., "Strategies to Extend Plasma Half-Lives of Recombinant Antibodies," Biodrugs, vol. 23, No. 2, pp. 93-109 (2009).
Stork et al., "A novel tri-functional antibody fusion protein with improved pharmacokinetic properties generated by fusing a bispecific single-chain diabody with an albumin-binding domain from streptococcal protein G," Protein Engineering, Design & Selection, vol. 20, No. 11, pp. 569-576 (2007).
Derrick et al., "The Third IgG-Binding Domain from Streptococcal Protein G. An Analysis by X-ray Crystallography of the Structure Alone and in a Complex with Fab," J. Mol. Biol., vol. 243, pp. 906-918 (1994).
Tashiro et al., "Structures of bacterial immunoglobulin-binding domains and their complexes with immunoglobulins," Current Opinion in Structural Biology, vol. 5, No. 4, pp. 471-481 (1995).
Bouvet, "Immunoglobulin Fab Fragment-Binding Proteins," Int. J. Immunopharmac., vol. 16, No. 5-6, pp. 419-424 (1994).

(Continued)

*Primary Examiner* — Phuong Huynh

(74) *Attorney, Agent, or Firm* — Marshall, Gerstein & Borun LLP

(57) ABSTRACT

The present invention relates to complexes comprising (i) an immunoglobulin (Ig) binding moiety and (ii) a pharmaceutically active moiety, wherein the Ig binding moiety specifically binds to the constant domain 1 of the heavy chain ($C_H1$) of an Ig molecule and their use for therapy and prophylaxis.

6 Claims, 21 Drawing Sheets

Specification includes a Sequence Listing.

(56) References Cited

OTHER PUBLICATIONS

Grimm et al., "Ribosome Display Selection of a Murine IgG$_1$ Fab Binding Affibody Molecule Allowing Species Selective Recovery of Monoclonal Antibodies," *Mol. Biotechnol.*, vol. 48, pp. 263-276 (2011).

Kraulis et al., "The serum albumin-binding domain of streptococcal protein G is a three-helical bundle: a heteronuclear NMR study," *FEBS Letters*, vol. 378, pp. 190-194 (1996).

Unverdorben et al., "Half-life extension of a single-chain diabody by fusion to domain B of Staphylococcal protein A," *Protein Engineering, Design & Selection*, vol. 25, No. 2, pp. 81-88 (2012).

International Preliminary Report on Patentability in corresponding PCT/EP2012/068802 dated Apr. 3, 2014.

Office Action in corresponding Japanese Patent Application No. 2014-531267, dated Jun. 28, 2016. (English Translation).

Office Action in corresponding Japanese Patent Application No. 2014-531267, dated Apr. 18, 2017. (English Translation).

Khaibullina et al., "Pulsed High-Intensity Focused Ultrasound Enhances Uptake of Radiolabeled Monoclonal Antibody to Human Epidermoid Tumor in Nude Mice," *J. Nucl. Med.*, vol. 49, pp. 295-302 (2008).

\* cited by examiner

Fig. 5, part 1

Fig. 5, part 2

Fig. 6

Affinity measurements

| construct | protein | $K_D$ (nM) pH 7.4 | $K_D$ (nM) pH 6 |
|---|---|---|---|
| $SpA_B$ | human IgG | 9 | 350 |
| | mouse IgG | 380 | 15000 |
| $SpA_D$ | human IgG | 22 | 148 |
| | human IgG Fab | - | n.d. |
| | human IgG Fc | 14 | 30 |
| | mouse IgG | 56 | 773 |
| | mouse IgG Fab | - | n.d. |
| | mouse IgG Fc | 54 | 980 |
| $SpA_{EZA}$ | human IgG | 37 | 65 |
| | human IgG Fab | - | n.d. |
| | human IgG Fc | 24 | 87 |
| | mouse IgG | 78 | 2480 |
| | mouse IgG Fab | - | n.d. |
| | mouse IgG Fc | 120 | 1000 |
| $SpG_{C3}$ | human IgG | 6 | 5 |
| | human IgG Fab | 190 | 150 |
| | human IgG Fc | 10 | 3.6 |
| | mouse IgG | 58 | 46 |
| | mouse IgG Fab | 190 | 190 |
| | mouse IgG Fc | 24 | n.d. |
| $PpL_{C4*}$ | human IgG | 1510 | 1130 |
| | human IgG Fab | 3100 | n.d. |
| | human IgG Fc | - | n.d. |
| | mouse IgG | - | n.d. |
| | mouse IgG Fab | - | n.d. |
| | mouse IgG Fc | - | n.d. | n.d., not determined.

Fig. 8

Pharmacokinetic properties

| construct | $M_r$ (kDa) | $S_r$ (nm) | $t_{1/2}\alpha$ (h) | $t_{1/2}\beta$ (h) | AUC (%h) |
|---|---|---|---|---|---|
| scDb | 54.5 | 2.6 | 0.2 ± 0.1 | 1.3 ± 0.3 | 52 ± 17 |
| scDb-SpA$_B$ | 59.9 | 2.6 | 2.2 ± 0.5 | 11.8 ± 1.6 | 1407 ± 352 |
| scDb-SpA$_D$ | 60.1 | 2.2 | 2.0 ± 0.8 | 9.0 ± 4.6 | 1042 ± 403 |
| scDb-SpA$_{EZ4}$ | 59.7 | 2.4 | 1.0 ± 0.3 | 4.2 ± 0.6 | 435 ± 79 |
| scDb-SpG$_{C3}$ | 59.6 | 2.7 | 2.8 ± 1.2 | 23.3 ± 5.9 | 1879 ± 279 |
| scDb-PpL$_{C4*}$ | 60.3 | 2.3 | 0.8 ± 0.1 | 2.4 ± 0.6 | 233 ± 136 |
| scFv | 26.7 | 1.2 | 0.1 ± 0.01 | 0.6 ± 0.2 | 16 ± 4 |
| scFv-SpA$_B$ | 33.6 | 2.7 | 1.0 ± 0.1 | 4.3 ± 0.7 | 376 ± 200 |
| scFv-SpA$_D$ | 33.8 | 2.3 | 1.1 ± 0.3 | 4.9 ± 1.0 | 434 ± 222 |
| scFv-SpA$_{EZ4}$ | 33.5 | 2.4 | 0.4 ± 0.2 | 1.1 ± 0.4 | 63 ± 29 |
| scFv-SpG$_{C3}$ | 33.4 | 2.7 | 0.8 ± 0.1 | 20.8 ± 11.0 | 1040 ± 589 |
| scFv-PpL$_{C4*}$ | 34.0 | 2.5 | 0.6 ± 0.2 | 2.7 ± 1.0 | 207 ± 128 |

Fig. 12

IgG CH1 domain sequences

| EU index | 122 | 123 | 124 | 125 | 126 | 127 | ... | 207 | 208 | 209 | 210 | 211 | ? | 212 | 213 | 214 |
|---|---|---|---|---|---|---|---|---|---|---|---|---|---|---|---|---|
| human γ1 | Gly | Pro | Ser | Val | Phe | Pro | ... | Ser | Asn | Thr | Lys | Val | – | Asp | Lys | Lys |
| human γ2 | Gly | Pro | Ser | Val | Phe | Pro | ... | Ser | Asn | Thr | Lys | Val | – | Asp | Lys | Thr |
| human γ3 | Gly | Pro | Ser | Val | Phe | Pro | ... | Ser | Asn | Thr | Lys | Val | – | Asp | Lys | Arg |
| human γ4 | Gly | Pro | Ser | Val | Phe | Pro | ... | Ser | Asn | Thr | Lys | Val | – | Asp | Lys | Arg |
| human μ | Ala | Pro | Thr | Leu | Phe | Pro | ... | Asn | Gly | Asn | Lys | – | – | Glu | Lys | Asn |
| human ε | Ser | Pro | Ser | Val | Phe | Pro | ... | Ser | Ser | Thr | Asp | Trp | Val | Asp | Asn | Lys |
| human δ | Ala | Pro | Asp | Val | Phe | Pro | ... | Ser | Lys | Ser | Lys | – | – | Lys | Glu | Ile |
| human α1 | Ser | Pro | Lys | Val | Phe | Pro | ... | Asn | Pro | Ser | Gln | – | – | Asp | Val | Thr |
| human α2 | Ser | Pro | Lys | Val | Phe | Pro | ... | Asn | Pro | Ser | Gln | – | – | Asp | Val | Thr |
| mouse γ1 | Pro | Pro | Ser | Val | Tyr | Pro | ... | Ser | Ser | Thr | Lys | Val | – | Asp | Lys | Lys |
| mouse γ2a | Ala | Pro | Ser | Val | Tyr | Pro | ... | Ser | Ser | Thr | Lys | Val | – | Asp | Lys | Lys |
| mouse γ2b | Ala | Pro | Ser | Val | Tyr | Pro | ... | Ser | Ser | Thr | Thr | Val | – | Asp | Lys | Lys |
| mouse γ3 | Ala | Pro | Ser | Val | Tyr | Pro | ... | Ser | Lys | Thr | Glu | Leu | – | Ile | Lys | Arg |
| rat g1 | Ala | Pro | Ser | Val | Tyr | Pro | ... | Ser | Ser | Thr | Lys | Val | – | Asp | Lys | Lys |

Differences to human γ1 are shown in bold letters

Fig. 13 scFv-SpG-C3 (anti-CEA)

```
ATG GAG ACA GAC ACA CTC CTG CTA TGG GTA CTG CTG CTC TGG GTT CCA GGT TCC ACT GGT   < 60
 M   E   T   D   T   L   L   L   W   V   L   L   L   W   V   P   G   S   T   G

GAC GCG GCC CAG CCG GCC ATG GCC CAG GTG AAA CTG CAG CAG TCT GGG GCA GAA CTT GTG   < 120
 D   A   A   Q   P   A   M   A   Q   V   K   L   Q   Q   S   G   A   E   L   V

AGG TCA GGG ACC TCA GTC AAG TTG TCC TGC ACA GCT TCT GGC TTC AAC ATT AAA GAC TCC   < 180
 R   S   G   T   S   V   K   L   S   C   T   A   S   G   F   N   I   K   D   S

TAT ATG CAC TGG TTG AGG CAG GGG CCT GAA CAG GGC CTG GAG TGG ATT GGA TGG ATT GAT   < 240
 Y   M   H   W   L   R   Q   G   P   E   Q   G   L   E   W   I   G   W   I   D

CCT GAG AAT GGT GAT ACT GAA TAT GCC CCG AAG TTC CAG GGC AAG GCC ACT TTT ACT ACA   < 300
 P   E   N   G   D   T   E   Y   A   P   K   F   Q   G   K   A   T   F   T   T

GAC ACA TCC TCC AAC ACA GCC TAC CTG CAG CTC AGC AGC CTG ACA TCT GAG GAC ACT GCC   < 360
 D   T   S   S   N   T   A   Y   L   Q   L   S   S   L   T   S   E   D   T   A

GTC TAT TAT TGT AAT GAG GGG ACT CCG ACT GGG CCG TAC TAC TTT GAC TAC TGG GGC CAA   < 420
 V   Y   Y   C   N   E   G   T   P   T   G   P   Y   Y   F   D   Y   W   G   Q

GGG ACC ACG GTC ACC GTC TCC TCA GGT GGA GGC GGT TCA GGG GGA GGT GGA TCC GGT GGA   < 480
 G   T   T   V   T   V   S   S   G   G   G   G   S   G   G   G   S   G   G

GGC GGT TCA GAC ATC GAG CTC ACC CAG TCT CCA GCA ATC ATG TCT GCA TCT CCA GGG GAG   < 540
 G   G   S   D   I   E   L   T   Q   S   P   A   I   M   S   A   S   P   G   E

AAA GTC ACC ATA ACC TGC AGT GCC AGC TCA AGT GTA AGT TAC ATG CAC TGG TTC CAG CAG   < 600
 K   V   T   I   T   C   S   A   S   S   S   V   S   Y   M   H   W   F   Q   Q

AAG CCA GGC ACT TCT CCC AAA CTC TGG ATT TAT AGC ACA TCC AAC CTG GCT TCT GGA GTC   < 660
 K   P   G   T   S   P   K   L   W   I   Y   S   T   S   N   L   A   S   G   V

CCT GCT CGC TTC AGT GGC AGT GGA TCT GGG ACC TCT TAC TCT CTC ACA ATC AGC CGA ATG   < 720
 P   A   R   F   S   G   S   G   S   G   T   S   Y   S   L   T   I   S   R   M

GAG GCT GAA GAT GCT GCC ACT TAT TAC TGC CAG CAA AGG AGT AGT TAC CCA CTC ACG TTC   < 780
 E   A   E   D   A   A   T   Y   Y   C   Q   Q   R   S   S   Y   P   L   T   F

GGT GCT GGC ACC AAG CTG GAG CTG AAA CGG GCG GCC GCA GGC GGA TCT GGC GGC ACC ACC   < 840
 G   A   G   T   K   L   E   L   K   R   A   A   A   G   G   S   G   G   T   T

TAC AAG CTG GTG ATC AAC GGC AAG ACC CTG AAG GGC GAG ACA ACC ACC AAG GCC GTC GAC   < 900
 Y   K   L   V   I   N   G   K   T   L   K   G   E   T   T   T   K   A   V   D

GCC GAG ACA GCC GAG AAG GCC TTC AAG CAG TAC GCC AAC GAC AAC GGC GTG GAC GGC GTG   < 960
 A   E   T   A   E   K   A   F   K   Q   Y   A   N   D   N   G   V   D   G   V

TGG ACC TAC GAC GAC GCC ACC AAG ACC TTC ACC GTG ACC GAG GGC GGA TCC CAC CAC CAC   < 1020
 W   T   Y   D   D   A   T   K   T   F   T   V   T   E   G   G   S   H   H   H

CAT CAC CAC TGA
 H   H   H   *
```

Fig. 14, part 1 scDb-SpG-C3 (anti-CEA x anti-CD3)

```
ATG GAG ACA GAC ACA CTC CTG CTA TGG GTA CTG CTG CTC TGG GTT CCA GGT TCC ACT GGT   < 60
 M   E   T   D   T   L   L   L   W   V   L   L   L   W   V   P   G   S   T   G

GAC GCC GCC CAG CCG GCC ATG GCC CAG GTC AAA CTG CAG CAG TCT GGG GCA GAA CTT GTG   < 120
 D   A   A   Q   P   A   M   A   Q   V   K   L   Q   Q   S   G   A   E   L   V

AGG TCA GGG ACC TCA GTC AAG TTG TCC TGC ACA GCT TCT GGC TTC AAC ATT AAA GAC TCC   < 180
 R   S   G   T   S   V   K   L   S   C   T   A   S   G   F   N   I   K   D   S

TAT ATG CAC TGG TTG AGG CAG GGG CCT GAA CAG GGC CTG GAG TGG ATT GGA TGG ATT GAT   < 240
 Y   M   H   W   L   R   Q   G   P   E   Q   G   L   E   W   I   G   W   I   D

CCT GAA AAT GGT GAT ACT GAA TAT GCC CCG AAG TTC CAG GGC AAG GCC ACT TTT ACT ACA   < 300
 P   E   N   G   D   T   E   Y   A   P   K   F   Q   G   K   A   T   F   T   T

GAC ACA TCC TCC AAC ACA GCC TAC CTG CAG CTC AGC AGC CTG ACA TCT GAG GAC ACT GCC   < 360
 D   T   S   S   N   T   A   Y   L   Q   L   S   S   L   T   S   E   D   T   A

GTC TAT TAT TGT AAT GAG GGG ACT CCG ACT CCG GGG ACT TAC TTT GAC TAC TGG GGC CAA   < 420
 V   Y   Y   C   N   E   G   T   P   T   P   G   T   Y   F   D   Y   W   G   Q

GGG ACC ACG GTC ACC GTC TCC TCA GGT GGC GGT GGA TCG GAT ATC CAG ATG ACC CAG TCC   < 480
 G   T   T   V   T   V   S   S   G   G   G   G   S   D   I   Q   M   T   Q   S

CCG AGT TCC CTG TCC GCC TCT GTG GGC GAT AGA GTC ACC ATC ACT TGC CGT GCC AGT CAG   < 540
 P   S   S   L   S   A   S   V   G   D   R   V   T   I   T   C   R   A   S   Q

GAC ATC CGT AAT TAT CTG AAC TGG TAT CAA CAG AAA CCA GGA AAA GCT CCG AAA CTA CTG   < 600
 D   I   R   N   Y   L   N   W   Y   Q   Q   K   P   G   K   A   P   K   L   L

ATT TAC TAC ACC TCC CGC CTG GAG TCT GGA GTC CCT TCT CGC TTC TCT GGT TCT GGT TCT   < 660
 I   Y   Y   T   S   R   L   E   S   G   V   P   S   R   F   S   G   S   G   S

GGG ACG GAT TAC ACT CTC ACC ATC AGC AGT CTG CAA CCG GAG GAC TTC GCA ACC TAT TAC   < 720
 G   T   D   Y   T   L   T   I   S   S   L   Q   P   E   D   F   A   T   Y   Y

TGT CAG CAA GGT AAT ACT CTG CCG TGG ACG TTC GGA CAG GGT ACC AAG GTG GAG GTT AAA   < 780
 C   Q   Q   G   N   T   L   P   W   T   F   G   Q   G   T   K   V   E   V   K

CGT GGA GGC GGT GGC AGC AGC GGG CGC GCC TCG GGC GCC GGT GGC TCA GAG GTT CAG CTG   < 840
 R   G   G   G   G   S   S   G   R   A   S   G   A   G   G   S   E   V   Q   L

GTG GAG TCT GGC GGT GGC CTG GTG CAG CCA GGG GGG TCA CTC CGT TTG TCC TGT GCA GCT   < 900
 V   E   S   G   G   G   L   V   Q   P   G   G   S   L   R   L   S   C   A   A
```

Fig. 14, part 2

Fig. 15, part 1

SpG-C3-Db-scTRAIL (anti-human EGFR)

```
ATG GAC TGG ACC TGG CGC GTG TTT TGC CTG CTC GCC GTG GCT CCT GGG GCC CAC AGC CTC  < 60
 M   D   W   T   W   R   V   F   C   L   L   A   V   A   P   G   A   H   S   L

GAG GCC AGC GAC TAC AAA GAC GAT GAC GAT AAA GGA GCC ACC ACC TAC AAG CTG GTG ATC  < 120
 E   A   S   D   Y   K   D   D   D   D   K   G   A   T   T   Y   K   L   V   I

AAC GGC AAG ACC CTG AAG GGC GAG ACA ACC ACC AAG GCC GTG GAC GCC GAG ACA GCC GAG  < 180
 N   G   K   T   L   K   G   E   T   T   T   K   A   V   D   A   E   T   A   E

AAG GCC TTC AAG CAG TAC GCC AAC GAC AAC GGC GTG GAC GGC GTG TGG ACC TAC GAC GAC  < 240
 K   A   F   K   Q   Y   A   N   D   N   G   V   D   G   V   W   T   Y   D   D

GCC ACC AAG ACC TTC ACC GTG ACC GAG GGC GGA TCC GGA GGT GGT GGT TCA GGA GGT GAG  < 300
 A   T   K   T   F   T   V   T   E   G   G   S   G   G   G   G   S   G   G   E

GTG CAG CTG GTC GAG TCT GGC GGC GGA CTG GTG CAG CCT GGC GGC TCC CTG AGA CTG TCT  < 360
 V   Q   L   V   E   S   G   G   G   L   V   Q   P   G   G   S   L   R   L   S

TGC GCT GCC TCC GGC TTC TCC CTG ACC AAC TAC GGC GTG CAC TGG GTC CGG CAG GCT CCC  < 420
 C   A   A   S   G   F   S   L   T   N   Y   G   V   H   W   V   R   Q   A   P

GGC AAG GGA CTG GAA TGG CTG GGC GTG ATT TGG TCC GGC GGC AAC ACC GAC TAC AAC ACC  < 480
 G   K   G   L   E   W   L   G   V   I   W   S   G   G   N   T   D   Y   N   T

CCT TTC ACC TCC CGG TTC ACC ATC TCC CGG GAC AAC TCC AAG AAC ACC CTG TAC CTG CAG  < 540
 P   F   T   S   R   F   T   I   S   R   D   N   S   K   N   T   L   Y   L   Q

ATG AAC TCC CTG CGG GCC GAG GAC ACC GCC GTG TAC TAC TGC GCC AGG GCT CTC ACC TAC  < 600
 M   N   S   L   R   A   E   D   T   A   V   Y   Y   C   A   R   A   L   T   Y

TAC GAC TAC GAG TTC GCC TAC TGG GGC CAG GGC ACC ACA GTG ACC GTG TCT AGT GGC GGT  < 660
 Y   D   Y   E   F   A   Y   W   G   Q   G   T   T   V   T   V   S   S   G

GGC GGC TCT GAT ATT CAG CTG ACC CAG TCC CCC TCC TTC CTG TCC GCC TCC GTG GGC GAC  < 720
 G   G   S   D   I   Q   L   T   Q   S   P   S   F   L   S   A   S   V   G   D

AGA GTG ACC ATC ACC TGC CGG GCC TCC CAG TCC ATC GGC ACC AAC ATC CAC TGG TAT CAG  < 780
 R   V   T   I   T   C   R   A   S   Q   S   I   G   T   N   I   H   W   Y   Q

CAG AAG CCT GGC AAG GCC CCT AAG CTG CTG ATC AAG TAC GCC TCC GAG TCT ATC TCC GGC  < 840
 Q   K   P   G   K   A   P   K   L   L   I   K   Y   A   S   E   S   I   S   G

GTG CCT TCC CGG TTC TCC GGC TCC GGC TCT GGA ACC GAG TTC ACC CTG ACC ATC TCC AGC  < 900
 V   P   S   R   F   S   G   S   G   S   G   T   E   F   T   L   T   I   S   S

CTG CAG CCT GAG GAC TTC GCC ACC TAC TAC TGC CAG CAG AAC AAC AAC TGG CCT ACC ACC  < 960
 L   Q   P   E   D   F   A   T   Y   Y   C   Q   Q   N   N   N   W   P   T   T

TTC GGC GCT GGC ACC AAG CTG GAA ATC AAG AGA GCG GCC GCA GGC AAC GGC ACC AGC AAC  < 1020
 F   G   A   G   T   K   L   E   I   K   R   A   A   A   G   N   G   T   S   N

GGG ACA TCC GAA TTC ACG CGT GGC ACC AGC GAG GAA ACC ATT AGC ACC GTC CAG GAA AAG  < 1080
 G   T   S   E   F   T   R   G   T   S   E   E   T   I   S   T   V   Q   E   K

CAG CAG AAC ATC AGC CCC CTG GTC CGG GAG AGA GGC CCC CAG AGA GTC GCC GCC CAC ATC  < 1140
 Q   Q   N   I   S   P   L   V   R   E   R   G   P   Q   R   V   A   A   H   I

ACC GGC ACC CGG GGC AGA AGC AAC ACC CTG AGC AGC CCC AAC AGC AAG AAC GAG AAG GCC  < 1200
 T   G   T   R   G   R   S   N   T   L   S   S   P   N   S   K   N   E   K   A

CTG GGC CGG AAG ATC AAC AGC TGG GAG AGC AGC AGA AGC GGC CAC AGC TTT CTG AGC AAC  < 1260
 L   G   R   K   I   N   S   W   E   S   S   R   S   G   H   S   F   L   S   N

CTG CAC CTG CGG AAC GGC GAG CTG GTC ATC CAC GAG AAG GGC TTC TAC TAC ATC TAC AGC  < 1320
 L   H   L   R   N   G   E   L   V   I   H   E   K   G   F   Y   Y   I   Y   S

CAG ACC TAC TTC AGA TTC CAA GAA GAG ATC AAA GAG AAC ACC AAG AAC GAC AAG CAG ATG  < 1380
 Q   T   Y   F   R   F   Q   E   E   I   K   E   N   T   K   N   D   K   Q   M
```

Fig. 15, part 2

```
GTG CAG TAC ATC TAC AAG TAC ACC AGC TAC CCC GAC CCC ATC CTG CTG ATG AAG TCC GCC   < 1440
 V   Q   Y   I   Y   K   Y   T   S   Y   P   D   P   I   L   L   M   K   S   A

CGG AAC AGC TGC TGG TCC AAG GAC GCC GAG TAC GGC CTG TAC AGC ATC TAC CAG GGC GGC   < 1500
 R   N   S   C   W   S   K   D   A   E   Y   G   L   Y   S   I   Y   Q   G   G

ATC TTC GAG CTG AAA GAG AAC GAC CGG ATC TTC GTG AGC GTG ACC AAC GAG CAC CTG ATC   < 1560
 I   F   E   L   K   E   N   D   R   I   F   V   S   V   T   N   E   H   L   I

GAC ATG GAC CAC GAG GCC AGC TTT TTC GGC GCA TTC CTG GTC GGC GGA GGG GGA TCC GGC   < 1620
 D   M   D   H   E   A   S   F   F   G   A   F   L   V   G   G   G   G   S   G

GGA GGA AGC ACC TCC GAA GAG ACT ATC TCT ACA GTC CAG GAA AAA CAG CAG AAT ATC TCC   < 1680
 G   G   S   T   S   E   E   T   I   S   T   V   Q   E   K   Q   Q   N   I   S

CCT CTC GTG CGG GAG CGG GGA CCT CAG CGG GTG GCC GCC CAT ATT ACA GGC ACA AGA GGC   < 1740
 P   L   V   R   E   R   G   P   Q   R   V   A   A   H   I   T   G   T   R   G

CGG TCC AAC ACC CTG TCC TCC CCC AAC TCT AAG AAT GAA AAG GCC CTC GGG AGA AAG ATC   < 1800
 R   S   N   T   L   S   S   P   N   S   K   N   E   K   A   L   G   R   K   I

AAC TCC TGG GAG TCC AGC CGC TCC GGC CAC TCC TTT CTG TCC AAT CTG CAC CTG AGA AAT   < 1860
 N   S   W   E   S   S   R   S   G   H   S   F   L   S   N   L   H   L   R   N

GGG GAG CTG GTC ATT CAC GAA AAG GGG TTT TAC TAT ATC TAC TCT CAG ACA TAC TTT AGG   < 1920
 G   E   L   V   I   H   E   K   G   F   Y   Y   I   Y   S   Q   T   Y   F   R

TTT CAG GAA GAA ATT AAA GAA AAT ACA AAG AAT GAT AAA CAG ATG GTC CAG TAT ATC TAT   < 1980
 F   Q   E   E   I   K   E   N   T   K   N   D   K   Q   M   V   Q   Y   I   Y

AAA TAC ACT TCC TAC CCT GAT CCT ATT CTG CTG ATG AAA AGC GCC AGA AAC AGC TGT TGG   < 2040
 K   Y   T   S   Y   P   D   P   I   L   L   M   K   S   A   R   N   S   C   W

AGC AAG GAT GCC GAA TAT GGG CTC TAC TCT ATC TAC CAG GGG GGG ATT TTT GAA CTT AAG   < 2100
 S   K   D   A   E   Y   G   L   Y   S   I   Y   Q   G   G   I   F   E   L   K

GAG AAT GAC AGA ATC TTT GTG TCT GTG ACA AAT GAG CAT CTG ATT GAT ATG GAT CAC GAA   < 2160
 E   N   D   R   I   F   V   S   V   T   N   E   H   L   I   D   M   D   H   E

GCC TCA TTC TTT GGA GCC TTT CTT GTG GGA GGG GGC GGA TCT GGT GGC GGA TCC ACC TCT   < 2220
 A   S   F   F   G   A   F   L   V   G   G   G   G   S   G   G   G   S   T   S

GAG GAA ACA ATA TCC ACC GTC CAG GAG AAG CAA CAA AAC ATT TCC CCC CTC GTG CGC GAA   < 2280
 E   E   T   I   S   T   V   Q   E   K   Q   Q   N   I   S   P   L   V   R   E

CGG GGC CCA CAG AGG GTC GCC GCT CAC ATT ACA GGG ACC AGG GGC CGC AGC AAT ACC CTG   < 2340
 R   G   P   Q   R   V   A   A   H   I   T   G   T   R   G   R   S   N   T   L

TCC AGC CCG AAC TCC AAA AAT GAG AAA GCG CTG GGG CGG AAG ATT AAT TCC TGG GAA AGC   < 2400
 S   S   P   N   S   K   N   E   K   A   L   G   R   K   I   N   S   W   E   S

TCC AGA AGC GGG CAC TCC TTC CTC AGC AAT CTG CAT CTG CGC AAC GGG GAA CTC GTG ATT   < 2460
 S   R   S   G   H   S   F   L   S   N   L   H   L   R   N   G   E   L   V   I

CAT GAG AAG GGA TTC TAT TAT ATC TAT TCC CAG ACA TAC TTC CGC TTC CAA GAG GAA ATT   < 2520
 H   E   K   G   F   Y   Y   I   Y   S   Q   T   Y   F   R   F   Q   E   E   I

AAA GAG AAC ACT AAA AAC GAT AAA CAA ATG GTT CAA TAC ATC TAC AAA TAT ACC TCT TAC   < 2580
 K   E   N   T   K   N   D   K   Q   M   V   Q   Y   I   Y   K   Y   T   S   Y

CCA GAT CCC ATC CTC CTC ATG AAG AGT GCC AGA AAC TCC TGC TGG TCT AAG GAT GCG GAA   < 2640
 P   D   P   I   L   L   M   K   S   A   R   N   S   C   W   S   K   D   A   E

TAC GGA TTG TAC TCC ATC TAT CAA GGG GGA ATC TTT GAG TTG AAA GAA AAT GAT CGC ATT   < 2700
 Y   G   L   Y   S   I   Y   Q   G   G   I   F   E   L   K   E   N   D   R   I

TTC GTG TCC GTC ACG AAT GAG CAC CTC ATA GAC ATG GAT CAT GAA GCG AGT TTC TTC GGG   < 2760
 F   V   S   V   T   N   E   H   L   I   D   M   D   H   E   A   S   F   F   G

GCT TTC CTC GTG GGT TGA C   < 2779
 A   F   L   V   G   *
```

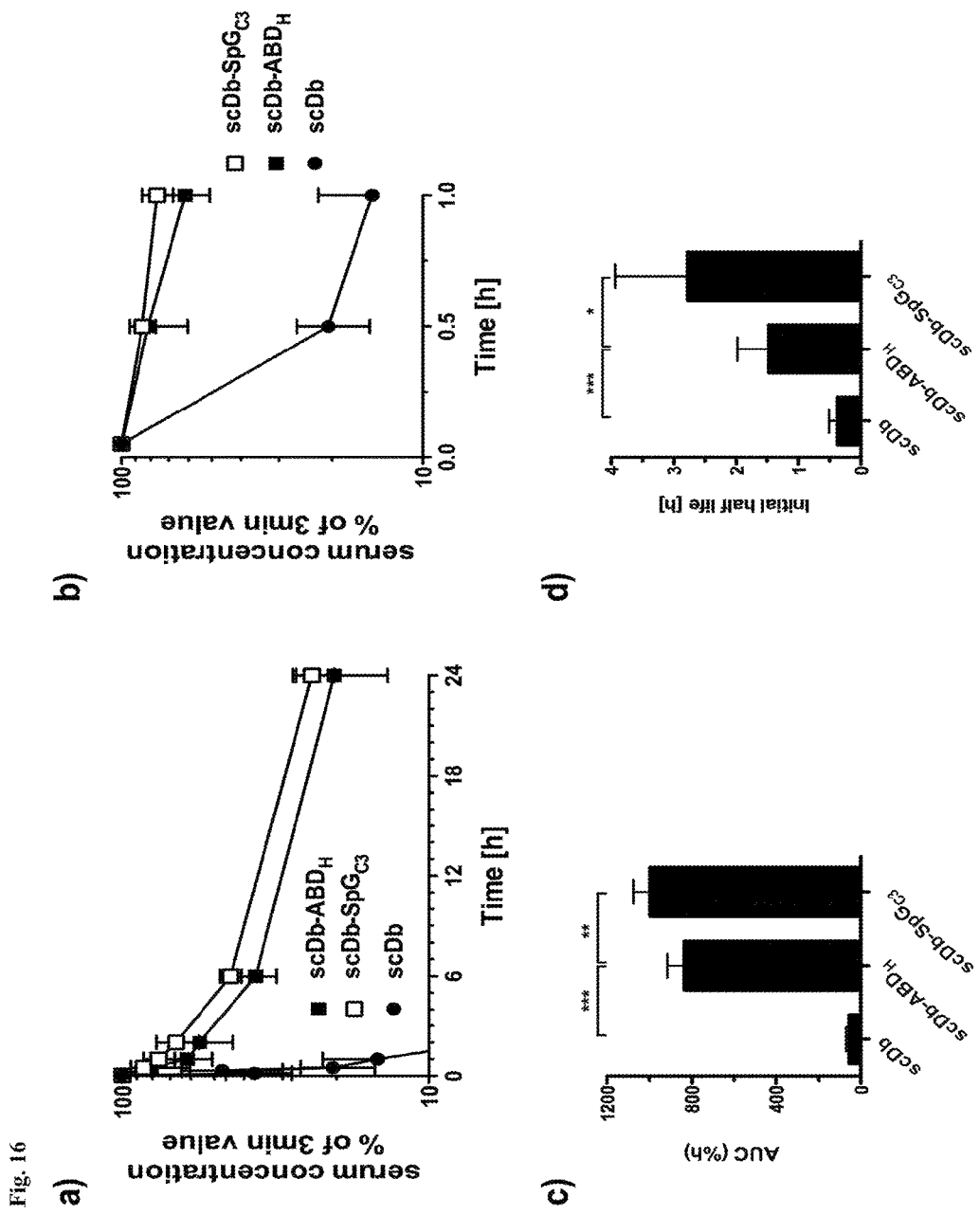

SERUM HALF-LIFE EXTENSION USING IGBD

CROSS-REFERENCE TO RELATED APPLICATIONS

This application claims the priority benefit of U.S. patent application Ser. No. 14/345,845 filed Mar. 19, 2014, now abandoned, which is a U.S. National Stage of PCT/EP2012/068802 filed Sep. 24, 2012 which claims priority to U.S. Patent Application No. 61/538,310 filed Sep. 23, 2011 and European Application No. 11 007 788.0 filed Sep. 23, 2011, the disclosures of which are incorporated herein by reference in their entireties.

TECHNICAL FIELD

The present invention relates to complexes comprising (i) an immunoglobulin (Ig) binding moiety and (ii) a pharmaceutically active moiety, wherein the Ig binding moiety specifically binds to the constant domain 1 of the heavy chain ($C_H1$) of an Ig molecule and their use for therapy and prophylaxis.

BACKGROUND

Most of the therapeutic applications of pharmaceuticals benefit from maintaining a therapeutic effective concentration over a prolonged period of time, often requiring a frequent administration or infusions, or a loco-regional application or subcutaneously of the drug utilizing a slow adsorption into the blood stream in order to maintain an effective concentration over a prolonged period of time. When a drug is administered by rapid intravenous injection into the vascular system, its removal from the blood almost always occurs in a biphasic fashion (see Greenblatt (1985) Ann. Rev. Med. 36:421-427). This can be mathematically described by a two-compartment model, which resolves the body into a central compartment and a peripheral compartment (see Dhillon and Gill: Basic Pharmacokinetics). These compartments have no distinct physiological or anatomical delimitation, however, the central compartment is considered to comprise tissues that are highly perfused (e.g. heart, lungs, kidneys, liver and brain) whilst the peripheral compartment comprises less well-perfused tissues (e.g. muscle, fat and skin). A two-compartment model assumes that upon drug administration into the central compartment, e.g. into the blood stream, the drug distributes between the central compartment and the peripheral compartment. However, the drug does not achieve instantaneous distribution, i.e. equilibration, between the two compartments. The drug concentration-time profile shows a curve, with the log drug concentration-time plot showing a biphasic response which can be used to distinguish whether a drug shows a one- or two-compartment model (see Dhillon and Gill: Basic Pharmacokinetics). Immediately after the dose is given, there is a phase of rapid drug disappearance from the blood, usually lasting from a few minutes to an hour or two, which may lead to a very substantial decrement in drug concentrations in blood. This initial phase (described by the initial or distribution plasma half-life; $t_{1/2}\alpha$) of rapid drug disappearance is determined mainly by reversible distribution of drug out of the "central" compartment, of which the vascular system is a component, into storage sites in peripheral tissues; very little of this initial rapid decline is determined by elimination or clearance. After distribution is complete, the blood concentration curve enters a less rapid phase of drug disappearance, termed the elimination phase (described by the terminal or elimination plasma half-life; $t_{1/2}\beta$), during which drug disappearance is determined mainly by irreversible clearance. The pattern of drug decline during this elimination phase is used to calculate the elimination plasma half-life which is generally determined only after drug distribution equilibrium has been attained (see Greenblatt (1985) Ann. Rev. Med. 36:421-427). Both, the initial plasma half-life and the terminal plasma half-life of a substance, e.g. a pharmaceutical, can be influenced in order to extend the bioavailability of such substance in the body by preventing its rapid clearance from the blood.

Small molecule pharmaceuticals, in particular most small protein therapeutics, including many of the alternative recombinant antibody formats (Kontermann (2010) Curr. Opin. Mol. ther. 12:176-183) but also the emerging class of alternative scaffold proteins (Nuttall & Walsh (2008) Curr. Opin. Pharmacol. 8:609-615; Gebauer & Skerra (2009) Curr. Opin. Chem. Biol. 13:245-255), suffer from a short serum half-life mainly due to their rapid clearance from circulation (Batra et al. (2002) Curr. Opin. Biotechnol. 13:603-608). These limitations of small size drugs has led to the development and implementation of half-life extension strategies to prolong circulation of these recombinant antibodies in the blood and thus to improve administration and pharmacokinetic as well as pharmacodynamic properties.

Extension of the half-life can help to reduce the number of applications and to lower doses, thus are beneficial for therapeutic but also economic reasons. Strategies to extend the plasma half-life of pharmaceuticals and therapeutic proteins have, therefore, attracted increasing interest (Pisal et al., (2010) J. Pharmaceut. Sci. 99:2557-2575; Kontermann (2009) BioDrugs 23:93-109; Kontermann (2011) Curr. Opin. Biotechnol. in press).

Several mechanisms are involved in clearance of drugs from circulation including peripheral blood-mediated elimination by proteolysis, renal and hepatic elimination, and elimination by receptor-mediated endocytosis (Tang et al. (2004) J. Pharmaceut. Sci. 93:2184-2204). Molecules possessing a small size, i.e. a low molecular mass with a threshold in the range of 40-50 kDa, are rapidly cleared by renal filtration and degradation. Responsible for renal clearance is the glomerular filtration barrier (GBM) formed by the fenestrated endothelium, the glomerular basement membrane and the slit diaphragm located between the podocyte foot processes (Tryggvason & Wartiovaara (2005) Physiology 20:96-101). While the fenestrae between the glomerular endothelial cells are rather large (50-100 nm) allowing free diffusion of molecules, the slit diaphragm represents the ultimate macromolecular barrier, forming an isoporous, zipper-like filter structure with numerous small, 4-5 nm diameter pores and a lower number of 8-10 nm diameter pores (Haraldsson & Sirensson (2004) New Physiol. Sci. 19:7-10; Wartiovaara et al. (2004) J. Clin. Invest. 114:1475-1483). Molecules with a hydrodynamic radius smaller than approximately 4-5 nm are therefore rapidly cleared from the blood. In addition, the charge of a protein contributes to renal filtration. Proteoglycans of the endothelial cells and the GBM form an anionic barrier, which partially prevents the traversal of negatively charged plasma macromolecules (Tryggvason & Wartiovaara (2005) Physiology 20:96-101). Consequently, the size of a protein therapeutic, i.e. its hydrodynamic radius, but also its physicochemical properties represent starting points in order to improve half-life. Furthermore, some plasma proteins such as serum albumin and IgG molecules possess an extraordinary long half-life in the range of 2-4 weeks in humans, which clearly discriminates these molecules from all the other plasma proteins (Kontermann (2009) BioDrugs 23:93-109). Responsible is a recycling through the neonatal Fc receptor (FcRn, Brambell receptor) (Roopenian & Akilesh (2007) Nat. Rev. Immunol. 7:715-725). Albumin and IgGs taken up by cells, e.g. endothelial cells, through macropinocytosis bind to the FcRn in a pH-dependent manner in the acidic environment of the early endosome. This binding diverges albumin and IgG from degradation in the lysosomal compartment and redirects them to the plasma membrane, where they are released back into the blood plasma due to the neutral pH. This offers additional opportunities to extend or modulate the half-life of proteins, e.g. through fusion to albumin or the Fc-region of IgG (Kontermann (2009) BioDrugs 23, 93-109). Finally, protein drugs that bind to a cellular surface receptor will be internalized by receptor-mediated endocytosis and subjected to lysosomal degradation if the protein drug stays bound to the receptor (Tang et al. (2004) J. Pharmaceut. Sci. 93:2184-2204; Lao & Kamei (2008) Biotechnol. Prog. 24:2-7). Hence, engineering of the interaction of the therapeutic protein with its receptor(s) at acidic pH can therefore also prolong half-life of the protein by allowing recycling of the unbound molecules into the blood stream as shown for engineered G-CSF and an anti-IL6 receptor antibody (Sarkar et al. (2002) Nat. Biotechnol. 20:908-913; Igawa et al. (2010) Nat. Biotechnol. 28:1203-1208).

Several half-life extension strategies have been developed in recent years (Kontermann (2009) BioDrugs 23:93-109; Kontermann (2011) Curr. Opin. Biotechnol. in press), including strategies such as PEGylation and hyperglycosylation with the aim to increase the hydrodynamic volume of the protein to reduce renal clearance, as well as strategies utilizing recycling processes executed by the neonatal Fc receptor (FcRn), which is responsible for the extraordinary long half-lives of serum IgGs and of serum albumin (Kim et al. (2006) Clin. Immunol. 122:146-155). For example, albumin has been employed for half-life extension through the generation of albumin fusion proteins. Several albumin fusion proteins, e.g. albinterferon alfa-2b and a coagulation factor IX-HSA fusion protein, have already entered clinical trials (Nelson et al. (2010) Gastroenterology 139:1267-1276; Metzner et al. (2009) Thromb. Haemost. 102:634-644). In addition, various molecules exhibiting albumin-binding activity have been used for half-life extension. For this approach, the albumin-binding moiety is coupled or fused to the therapeutic protein leading to reversible binding to serum albumin after administration. Such albumin-binding molecules include fatty acids, organic molecules, peptides, single-chain Fv, domain antibodies, nanobodies but also domains from naturally occurring proteins capable of binding albumin (for review see: Kontermann (2009) BioDrugs 23:93-109). For example, an albumin-binding domain (ABD) from streptococcal protein G was used to prolong the plasma half-life of recombinant antibodies and Affibody molecules (Stork et al. (2007) Protein Eng. Des. Sel. 20:569-576; Andersen et al. (2010) J. Biol. Chem. 286:5234-5241). Fusion of the ABD resulted in similar half-lives as seen for an albumin fusion protein and an improved tumor accumulation as shown for a bispecific single-chain diabody (Stork et al. (2007) Protein Eng. Des. Sel. 20:569-576; Stork et al. (2009) J. Biol. Chem. 284:25612-25619). These studies, however, also revealed that albumin and ABD fusion proteins do not reach the long half-life of IgG molecules. Attempts to further prolong half-life by applying an ABD with increased affinity for albumin resulted only in a marginal improvement (Hopp et al., 2010, Protein Eng. Des. Sel. 23:827-834). Non-covalent interaction with serum IgG also represents a feasible alternative to binding to serum albumin. This approach was already tested with a bispecific diabody with affinity for mouse Fcγ1, which prolonged the terminal plasma half-life of the diabody from 1.7 h to 10 h in mice (Holliger et al. (1997) Nat. Biotechnol. 15:632-636).

However, many disadvantages are associated with above strategies of extending the plasma half-life of pharmaceuticals. The usage of PEG, polysialic acid and HES requires their chemical conjugation to the pharmaceutical, which consequently complicates the production and analysis of the final product. PEG is not biologically degradable and may accumulate in the body of a patient which may lead to further complications. Moreover, it has been shown that these modification were only able to prolong the serum half-life of pharmaceuticals to a limited extend. Similarly, also the serum half-life extension via the conjugation, fusion or binding of the pharmaceutical to serum albumin or via Fc-fusion proteins remains significantly below the serum half-life of IgG. There is thus, a clear need for the development of new strategies allowing for the extension of the serum half-life of pharmaceuticals, especially of therapeutic proteins, which overcome these disadvantages.

Present inventors surprisingly found that the fusion of pharmaceuticals to an immunoglobulin-binding domain (IgBD) solves this problem. IgBDs are known from various bacterial proteins, e.g. staphylococcal protein A (SpA), streptococcal protein G (SpG) and protein L of *Peptostreptococcus* (PpL) (Tashiro & Montelione (1995) Curr. Biol. 5:471-481; Sidorin & Solov'eva (2011) Biochemistry (Mosc.) 76:363-378). These IgBDs have a length of 50 to 60 amino acid residues and form either a 3-α-helix bundle or a compact structure composed of a 4-stranded β-sheet and one α-helix (Tashiro & Montelione (1995) Curr. Biol. 5:471-481). IgBDs are, thus, particularly stable which benefits the production and storage properties of fusion proteins comprising them.

IgBDs show a high affinity to serum immunoglobulins, with most of them binding to the same location on the Fc domain of an immunoglobulin as the neonatal Fc receptor, e.g. in IgG the primary binding site is located at the $C_H2$-$C_H3$ interface of one heavy chain (Deisenhofer (1981) Biochemistry 20:2361-2370). They are thus, competing with the FcRn binding and may negatively influence the recycling of the immunoglobulin molecule via the FcRn. For these reasons, IgBDs have so far not been considered for the extension of the serum half-life of pharmaceuticals. However, some bacterial IgBDs are also capable of binding to different regions of the Fab fragment (Tashiro & Montelione (1995) Curr. Biol. 5:471-481). Present inventors were able to show that the fusion of pharmaceuticals to an IgBD significantly prolongs the serum half-life of such pharmaceutical, probably due to the fact that these IgBDs do not compete with the Fc receptor binding.

The fusion or conjugation of a pharmaceutical to such IgBD thus, represents an advantageous possibility of extending their serum half-life as the binding of such fusion protein to an immunoglobulin molecule has a twofold effect; firstly, the clearance by renal filtration and degradation is limited or prevented, and secondly, the recycling of the fusion protein via the FcRn is allowed for.

The complexes of the present invention provide inter alia the following advantageous properties increase of the solubility of the respective pharmaceutically active moiety in vivo, increase of the in vitro stability of the respective pharmaceutically active moiety, which results in an extended shelf-life of such fusion protein. In cases wherein the pharmaceutical active moiety is a protein or peptide, a further advantage of fusing such moiety to an IgBD of the present invention is the increased expression of such fusion proteins, e.g. in mammalian expression systems. In addition, the complexing of the pharmaceutical moiety to an immunoglobulin binding moiety, in particular if the pharmaceutical moiety is a protein or peptide allows an easier and/or faster purification of such pharmaceutical.

SUMMARY OF THE INVENTION

In a first aspect, the present invention relates to a complex comprising (i) an immunoglobulin (Ig) binding moiety and (ii) a pharmaceutically active moiety, wherein the Ig binding moiety specifically binds to the constant domain 1 of the heavy chain ($C_H1$) of an Ig molecule.

In a second aspect, the present invention provides a nucleic acid molecule comprising a sequence encoding the complex of the first aspect.

In a third aspect, the present invention provides a vector comprising the nucleic acid of the second aspect.

In a fourth aspect, the present invention provides an isolated cell containing the complex of the first aspect and/or the nucleic acid molecule of the second aspect and/or the vector of the third aspect In a fifth aspect, the present invention provides a pharmaceutical composition comprising the complex of the first aspect, the nucleic acid of the second aspect, the vector of the third aspect and/or the cell of the fourth aspect and a pharmaceutical acceptable carrier and/or excipient.

In a sixth aspect, the present invention provides the complex of the first aspects, the nucleic acid of the second aspect, the vector of third aspect, the cell of the fourth aspect, the pharmaceutical composition of the fifth aspect for use in extending the serum half-life.

In a seventh aspect, the present invention provides the complex of the first aspects, the nucleic acid of the second aspect, the vector of third aspect, the cell of the fourth aspect, the pharmaceutical composition of the fifth aspect for use as a medicament.

BRIEF DESCRIPTION OF THE DRAWINGS

FIG. 8: Biochemical and pharmacokinetic properties of scDb-IgBD and scFv-IgBD fusion proteins in the mouse. ScDb-IgBD and scFv-IgBD fusion proteins were i.v. injected into CD1 mice (25 g/animal) and serum concentrations of the antibody molecules were determined at different time points by ELISA. Data were normalized considering maximal concentration at the first time point (3 min). tact indicates the initial plasma half-life; $t_{1/2}\beta$ indicates the terminal plasma half-life; AUC indicates the bioavailability of the tested scDb-IgBD and scFv-IgBD fusion proteins. The moleuclar masses were calculated from the amino acid sequences. Stokes radii (Sr) were determined by size exclusion chromatography.

FIG. 12: Amino acid sequences of the SpG-C3 binding epitope on the CH1 domains of human, mouse, and rat IgG according to EU index as in Kabat.

FIG. 13: Nucleic acid and amino acid sequence of scFv-SpG-C3 fusion protein (anti-CEA). SpG$_{C3}$ sequence is markes with a grey box, the leader sequence is underlined.

FIG. 14: Nucleic acid and amino acid sequence of scDb-SpG-C3 fusion protein (anti-CEA×anti-CD3). SpG$_{C3}$ sequence is markes with a grey box, the leader sequence is underlined.

FIG. 15: Nucleic acid and amino acid sequence of SpG-C3-Db-scTRAIL (anti-human EGFR) fusion protein. SpG$_{C3}$ sequence is markes with a grey box, the leader sequence is underlined.

FIG. 16: Pharmakocinetic properties of scDb-SpG$_{C3}$ and scDb-ABD$_H$. a) ScDb, scDb-SpG$_{C3}$ and scDb-ABD$_H$ fusion proteins were i.v. injected into CD1 mice (25 g/animal) and serum concentrations at different time points were determined by ELISA. The 3 min value was set to 100% for normalization. b) Plasma concentrations shown for the first 1 h. c) AUC determined over the first 24 h. d) Initial plasma half-lives determined for the first 3 time points (up to 1 h). Plasma half-lives and AUC$_{0-24h}$ of scDb, scDb-SpG$_{C3}$ and scDb-ABD$_H$ were calculated from the serum concentrations by Excel and statistics were performed using a T-test with GraphPad Prism.

DETAILED DESCRIPTION

Figure 1:
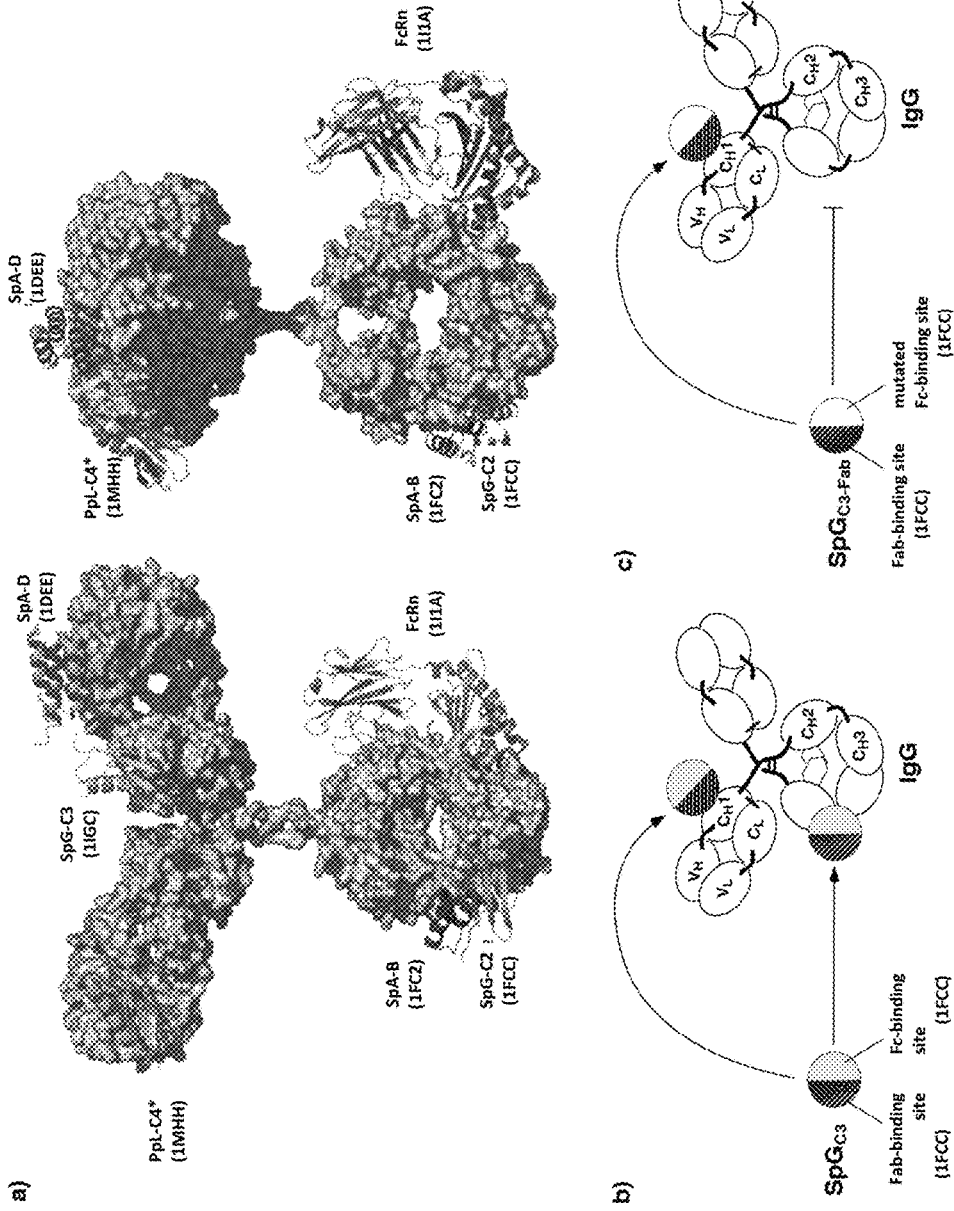
FIG. 1: Summary of IgBD bound to human IgG1. IgBDs from protein A ($SpA_B$, $SpA_D$), protein G ($SpG_{C2}$, $SpG_{C3}$) and protein L ($PpL_{C4}$*) in complex with IgG were visualized on a human IgG1 model (Clark (1997) Chem. Immunol. 65:88-110). In addition, the extracellular region of human FcRn bound to the Fc region was included (Burmeister et al. (1994) Nature 372:379-383). PDB entries are indicated for each IgBD and the FcRn. The structures were visualized with the PyMOL Molecular Graphics System (Version 1.3, Schridinger, LLC). b) Schematic illustration of binding of $SpG_{C3}$, possessing one binding site for CH1 and one binding site for the Fc part, to IgG. c) Schematic illustration of binding of $SpG_{C3-Fab}$, possessing one binding site for CH1 and a mutated inactive Fc binding site, to the CH1 domain of IgG only.

Before the present invention is described in detail below, it is to be understood that this invention is not limited to the particular methodology, protocols and reagents described herein as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art.

Preferably, the terms used herein are defined as described in "A multilingual glossary of biotechnological terms: (IUPAC Recommendations)", Leuenberger, H. G. W, Nagel, B. and Kölbl, H. eds. (1995), Helvetica Chimica Acta, CH-4010 Basel, Switzerland).

Several documents are cited throughout the text of this specification. Each of the documents cited herein (including all patents, patent applications, scientific publications, manufacturer's specifications, instructions, GenBank Accession Number sequence submissions etc.), whether supra or infra, is hereby incorporated by reference in its entirety. Nothing herein is to be construed as an admission that the invention is not entitled to antedate such disclosure by virtue of prior invention.

Definitions

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

The term "complex" as used herein, refers to a whole that comprehends a number of individual components, parts or moieties which are in close proximity to each other and fulfil a common or interrelated function. The individual parts of such complex may fulfil differing functions in order to achieve the common function of the complex, i.e. one part of the complex may mediate one function (e.g. the binding of the complex) whilst the other part of the complex may mediate a different function (e.g. the activity of the complex) in order to fulfil the common function (e.g. of a site specific activity). The individual moieties of a complex may be of the same or of differing nature, i.e. they may be composed of the same, a similar or of differing chemical entities such as but not limited to nucleotides, amino acids, nucleic acids, peptides, polypeptides, proteins, carbohydrates, and/or lipids. Exemplified, a complex may comprise a number of associated proteins, or a mixture of one or more proteins and one or more nucleic acids or a mixture of one or more proteins and one or more lipids and/or carbohydrates. It is understood that any other combination of identical, similar or differing chemical entities is also encompassed. The individual moieties of a complex may or may not be interconnected. Typically, the individual parts of a complex are connected via covalent or non-covalent bonds.

The terms "polynucleotide" and "nucleic acid" are used interchangeably herein and are understood as a polymeric or oligomeric macromolecule made from nucleotide monomers. Nucleotide monomers are composed of a nucleobase, a five-carbon sugar (such as but not limited to ribose or 2'-deoxyribose), and one to three phosphate groups. Typically, a polynucleotide is formed through phosphodiester bonds between the individual nucleotide monomers. In the context of the present invention referred to nucleic acid molecules include but are not limited to ribonucleic acid (RNA), deoxyribonucleic acid (DNA), and mixtures thereof such as e.g. RNA-DNA hybrids. The nucleic acids, can e.g. be synthesized chemically, e.g. in accordance with the phosphotriester method (see, for example, Uhlmann & Peyman (1990) Chemical Reviews 90:543-584). "Aptamers" are nucleic acids which bind with high affinity to a polypeptide. Aptamers can be isolated by selection methods such as SELEmir146-a (see e.g. Jayasena (1999) Clin. Chem. 45:1628-50; Klug and Famulok (1994) M. Mol. Biol. Rep. 20:97-107; U.S. Pat. No. 5,582,981) from a large pool of different single-stranded RNA molecules. Aptamers can also be synthesized and selected in their mirror-image form, for example as the L-ribonucleotide (Nolte et al. (1996) Nat. Biotechnol. 14:1116-1119; Klussmann et al. (1996) Nat. Biotechnol. 14:1112-1115). Forms which have been isolated in this way enjoy the advantage that they are not degraded by naturally occurring ribonucleases and, therefore, possess greater stability.

The terms "protein" and "polypeptide" are used interchangeably herein and refer to any peptide-bond-linked chain of amino acids, regardless of length or post-translational modification. Proteins usable in the present invention (including protein derivatives, protein variants, protein fragments, protein segments, protein epitops and protein domains) can be further modified by chemical modification. This means such a chemically modified polypeptide comprises other chemical groups than the 20 naturally occurring amino acids. Examples of such other chemical groups include without limitation glycosylated amino acids and phosphorylated amino acids. Chemical modifications of a polypeptide may provide advantageous properties as compared to the parent polypeptide, e.g. one or more of enhanced stability, increased biological half-life, or increased water solubility.

As used herein, the term "variant" is to be understood as a polynucleotide or protein which differs in comparison to the polynucleotide or protein from which it is derived by one or more changes in its length or sequence. The polypeptide or polynucleotide from which a protein or nucleic acid variant is derived is also known as the parent or parental polypeptide or polynucleotide. The term "variant" comprises "fragments" or "derivatives" of the parent molecule. Typically, "fragments" are smaller in length or size than the parent molecule, whilst "derivatives" exhibit one or more differences in their sequence in comparison to the parent molecule. Also encompassed are modified molecules such as but not limited to post-translationally modified proteins (e.g. glycosylated, biotinylated, phosphorylated, ubiquitinated, palmitoylated, or proteolytically cleaved proteins) and modified nucleic acids such as methylated DNA. Also mixtures of different molecules such as but not limited to RNA-DNA hybrids, are encompassed by the term "variant". Typically, a variant is constructed artificially, preferably by gene-technological means whilst the parent polypeptide or polynucleotide is a wild-type protein or polynucleotide. However, also naturally occurring variants are to be understood to be encompassed by the term "variant" as used herein. Further, the variants usable in the present invention may also be derived from homologs, orthologs, or paralogs of the parent molecule or from artificially constructed variant, provided that the variant exhibits at least one biological activity of the parent molecule, i.e. is functionally active.

The changes in the nucleotide or amino acid sequence may be nucleotide or amino acid exchanges, insertions, deletions, 5'- or 3' truncations, N- or C-terminal truncations, or any combination of these changes, which may occur at one or several sites. In preferred embodiments, a variant usable in the present invention exhibits a total number of up to 200 (up to 1, 2, 3, 4, 5, 6, 7, 8, 9, 10, 15, 20, 25, 30, 35, 40, 45, 50, 55, 60, 65, 70, 75, 80, 85, 90, 95, 100, 110, 120, 130, 140, 150, 160, 170, 180, 190, or 200) changes in the nucleotide or amino acid sequence (i.e. exchanges, insertions, deletions, and/or truncations). Amino acid exchanges may be conservative and/or non-conservative. Alternatively or additionally, a "variant" as used herein, can be characterized by a certain degree of sequence identity to the parent polypeptide or parent polynucleotide from which it is derived. More precisely, a protein variant in the context of the present invention exhibits at least 70% sequence identity to its parent polypeptide. A polynucleotide variant in the context of the present invention exhibits at least 70% sequence identity to its parent polynucleotide. Preferably, the sequence identity of protein variants is over a continuous stretch of 20, 30, 40, 45, 50, 60, 70, 80, 90, 100 or more amino acids. Preferably, the sequence identity of polynucleotide variants is over a continuous stretch of 60, 90, 120, 135, 150, 180, 210, 240, 270, 300 or more nucleotides.

The term "at least 70% sequence identity" is used throughout the specification with regard to polypeptide and polynucleotide sequence comparisons. This expression preferably refers to a sequence identity of at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% to the respective reference polypeptide or to the respective reference polynucleotide.

In case where two sequences are compared and the reference sequence is not specified in comparison to which the sequence identity percentage is to be calculated, the sequence identity is to be calculated with reference to the longer of the two sequences to be compared, if not specifically indicated otherwise. If the reference sequence is indicated, the sequence identity is determined on the basis of the full length of the reference sequence indicated by SEQ ID, if not specifically indicated otherwise. For example, a peptide sequence consisting of 358 amino acids compared to the amino acid sequence of an IgG molecule may exhibit a maximum sequence identity percentage of 80.09% (358/447) while a sequence with a length of 224 amino acids may exhibit a maximum sequence identity percentage of 50.11% (224/447). The similarity of nucleotide and amino acid sequences, i.e. the percentage of sequence identity, can be determined via sequence alignments. Such alignments can be carried out with several art-known algorithms, preferably with the mathematical algorithm of Karlin and Altschul (Karlin & Altschul (1993) Proc. Natl. Acad. Sci. USA 90:5873-5877), with hmmalign (HMMER package, or with the CLUSTAL algorithm (Thompson et al. (1994) Nucleic Acids Res. 22:4673-4680). The grade of sequence identity (sequence matching) may be calculated using e.g. BLAST, BLAT or BlastZ (or BlastX). A similar algorithm is incorporated into the BLASTN and BLASTP programs of Altschul et al. (1990) J. Mol. Biol. 215:403-410. BLAST polynucleotide searches are performed with the BLASTN program, score=100, word length=12. BLAST protein searches are performed with the BLASTP program, score=50, word length=3. To obtain gapped alignments for comparative purposes, Gapped BLAST is utilized as described in Altschul et al. (1997) Nucleic Acids Res. 25:3389-3402. When utilizing BLAST and Gapped BLAST programs, the default parameters of the respective programs are used. Sequence matching analysis may be supplemented by established homology mapping techniques like Shuffle-LAGAN (Brudno M. (2003b) Bioinformatics 19 Suppl 1:154-162) or Markov random fields. When percentages of sequence identity are referred to in the present application, these percentages are calculated in relation to the full length of the longer sequence, if not specifically indicated otherwise. "Hybridization" can also be used as a measure of sequence identity or homology between two nucleic acid sequences. A nucleic acid sequence encoding F, N, or M2-1, or a portion of any of these can be used as a hybridization probe according to standard hybridization techniques. Hybridization conditions are known to those skilled in the art and can be found, for example, in Current Protocols in Molecular Biology, John Wiley & Sons, N.Y., 6.3.1-6.3.6, 1991. "Moderate hybridization conditions" are defined as equivalent to hybridization in 2× sodium chloride/sodium citrate (SSC) at 30° C., followed by a wash in 1×SSC, 0.1% SDS at 50° C. "Highly stringent conditions" are defined as equivalent to hybridization in 6× sodium chloride/sodium citrate (SSC) at 45° C., followed by a wash in 0.2×SSC, 0.1% SDS at 65° C.

The term "immunoglobulin (Ig)" as used herein refers to immunity conferring glycoproteins of the immunoglobulin superfamily. "Surface immunoglobulins" are attached to the membrane of effector cells by their transmembrane region and encompass molecules such as but not limited to B-cell receptors, T-cell receptors, class I and II major histocompatibility complex (MHC) proteins, beta-2 microglobulin (β2M), CD3, CD4 and CD8. Typically, the term "antibody" as used herein refers to secreted immunoglobulins which lack the transmembrane region and can thus, be released into the bloodstream and body cavities. Human antibodies are grouped into different isotypes based on the heavy chain they possess. There are five types of human Ig heavy chains denoted by the Greek letters: α, δ, ε, γ, and μ. The type of heavy chain present defines the class of antibody, i.e. these chains are found in IgA, IgD, IgE, IgG, and IgM antibodies, respectively, each performing different roles, and directing the appropriate immune response against different types of antigens. Distinct heavy chains differ in size and composition; α and γ comprise approximately 450 amino acids, while and c have approximately 550 amino acids (Janeway et al. (2001) Immunobiology, Garland Science). IgA is found in mucosal areas, such as the gut, respiratory tract and urogenital tract, as well as in saliva, tears, and breast milk and prevents colonization by pathogens (Underdown & Schiff (1986) Annu. Rev. Immunol. 4:389-417). IgD mainly functions as an antigen receptor on B cells that have not been exposed to antigens and is involved in activating basophils and mast cells to produce antimicrobial factors (Geisberger et al. (2006) Immunology 118:429-437; Chen et al. (2009) Nat. Immunol. 10:889-898). IgE is involved in allergic reactions via its binding to allergens triggering the release of histamine from mast cells and basophils. IgE is also involved in protecting against parasitic worms (Pier et al. (2004) Immunology, Infection, and Immunity, ASM Press). IgG provides the majority of antibody-based immunity against invading pathogens and is the only antibody isotype capable of crossing the placenta to give passive immunity to fetus (Pier et al. (2004) Immunology, Infection, and Immunity, ASM Press). In humans there are four different IgG subclasses (IgG1, 2, 3, and 4), named in order of their abundance in serum with IgG1 being the most abundant (~66%), followed by IgG2 (~23%), IgG3 (~7%) and IgG (~4%). The biological profile of the different IgG classes is determined by the structure of the respective hinge region. IgM is expressed on the surface of B cells in a monomeric form and in a secreted pentameric form with very high avidity. IgM is involved in eliminating pathogens in the early stages of B cell mediated (humoral) immunity before sufficient IgG is produced (Geisberger et al. (2006) Immunology 118:429-437).

Antibodies are not only found as monomers but are also known to form dimers of two Ig units (e.g. IgA), tetramers of four Ig units (e.g. IgM of teleost fish), or pentamers of five Ig units (e.g. mammalian IgM). Antibodies are typically made of four polypeptide chains comprising two identical heavy chains and identical two light chains which are connected via disulfide bonds and resemble a "Y"-shaped macro-molecule. Each of the chains comprises a number of immunoglobulin domains out of which some are constant domains and others are variable domains. Immunoglobulin domains consist of a 2-layer sandwich of between 7 and 9 antiparallel β-strands arranged in two β-sheets. Typically, the heavy chain of an antibody comprises four Ig domains with three of them being constant ($C_H$ domains: $C_H1$, $C_H2$, $C_H3$) domains and one of the being a variable domain ($V_H$). The light chain typically comprises one constant Ig domain ($C_L$) and one variable Ig domain ($V_L$). Exemplified, the human IgG heavy chain is composed of four Ig domains linked from N- to C-terminus in the order $V_H$-$C_H1$-$C_H2$-$C_H3$ (also referred to as $V_H$-Cγ1-Cγ2-Cγ3), whereas the human IgG light chain is composed of two immunoglobulin domains linked from N- to C-terminus in the order $V_L$-$C_L$, being either of the kappa or lambda type (Vκ-Cκ or Vλ-Cλ).

Exemplified, the constant chain of human IgG comprises 447 amino acids. Throughout the present specification and claims, the numbering of the amino acid positions in an immunoglobulin are that of the "EU index" as in Kabat, E. A., Wu, T. T., Perry, H. M., Gottesman, K. S., and Foeller, C., (1991) Sequences of proteins of immunological interest, 5th ed. U.S. Department of Health and Human Service, National Institutes of Health, Bethesda, Md. The "EU index as in Kabat" refers to the residue numbering of the human IgG1EU antibody. Accordingly, $C_H$ domains in the context of IgG are as follows: "$C_H$" refers to amino acid positions 118-220 according to the EU index as in Kabat; "$C_H2$" refers to amino acid positions 237-340 according to the EU index as in Kabat; and "$C_H3$" refers to amino acid positions 341-447 according to the EU index as in Kabat.

Papain digestion of antibodies produces two identical antigen binding fragments, called "Fab fragments" (also referred to as "Fab portion" or "Fab region") each with a single antigen binding site, and a residual "Fc fragment" (also referred to as "Fc portion" or "Fc region") whose name reflects its ability to crystallize readily. The crystal structure of the human IgG Fc region has been determined (Deisenhofer (1981) Biochemistry 20:2361-2370). In IgG, IgA and IgD isotypes, the Fc region is composed of two identical protein fragments, derived from the $C_H2$ and $C_H3$ domains of the antibody's two heavy chains; in IgM and IgE isotypes, the Fc regions contain three heavy chain constant domains ($C_H2$-4) in each polypeptide chain. In addition, smaller immunoglobulin molecules exist naturally or have been constructed artificially. The term "Fab' fragment" refers to a Fab fragment additionally comprise the hinge region of an Ig molecule whilst "F(ab')$_2$ fragments" are understood to comprise two Fab' fragments being either chemically linked or connected via a disulfide bond. Whilst "single domain antibodies (sdAb)" (Desmyter et al. (1996) Nat. Structure Biol. 3:803-811) and "Nanobodies" only comprise a single $V_H$ domain, "single chain Fv (scFv)" fragments comprise the heavy chain variable domain joined via a short linker peptide to the light chain variable domain (Huston et al. (1988) Proc. Natl. Acad. Sci. USA 85, 5879-5883). Divalent single-chain variable fragments (di-scFvs) can be engineered by linking two scFvs (scFvA-scFvB). This can be done by producing a single peptide chain with two $V_H$ and two $V_L$ regions, yielding "tandem scFvs" ($V_H$A-$V_L$A-$V_H$B-

$V_LB$). Another possibility is the creation of scFvs with linkers that are too short for the two variable regions to fold together, forcing scFvs to dimerize. Usually linkers with a length of 5 residues are used to generate these dimers. This type is known as "diabodies". Still shorter linkers (one or two amino acids) between a $V_H$ and $V_L$ domain lead to the formation of monospecific trimers, so-called "triabodies" or "tribodies". Bispecific diabodies are formed by expressing to chains with the arrangement $V_HA$-$V_LB$ and $V_HB$-$V_LA$ or $V_LA$-$V_HB$ and $V_LB$-$V_HA$, respectively. Single-chain diabodies (scDb) comprise a $V_HA$-$V_LB$ and a $V_HB$-$V_LA$ fragment which are linked by a linker peptide (P) of 12-20 amino acids, preferably 14 amino acids, ($V_HA$-$V_LB$-P-$V_HB$-$V_LA$). "Bi-specific T-cell engagers (BiTEs)" are fusion proteins consisting of two scFvs of different antibodies wherein one of the scFvs binds to T cells via the CD3 receptor, and the other to a tumor cell via a tumor specific molecule (Kufer et al. (2004) Trends Biotechnol. 22:238-244). Dual affinity retargeting molecules ("DART" molecules) are diabodies additionally stabilized through a C-terminal disulfide bridge.

The term "immunoglobulin (Ig) binding moiety" as used herein refers to a moiety or part of a complex which interacts with an immunoglobulin. Typically an Ig binding moiety comprises a polypeptide or a protein which binds to the heavy and/or to the light chain of an Ig, preferably an antibody. An Ig binding moiety may comprise an "Ig binding domain (IgBD)" as well as further domains fulfilling additional functions such as but not limited to stabilizing the Ig binding moiety, or promoting the Ig binding potential of the IgBD.

The term "Ig binding domain (IgBD)" as used herein refers to domains which mediate the actual binding of the Ig binding moiety to the Ig molecule. An IgBD may bind to any of the domains of an Ig molecule, i.e. to the variable domains $V_H$ or $V_L$ and/or to the constant domains $C_H1$, $C_H2$, $C_H3$ and/or $C_L$ of an Ig molecule. Typically an IgBD has an affinity to bind to an Ig molecule at neutral pH (i.e. pH 7), however also binding at lower of higher pH values, e.g. at pH values 5, 6, or 8, may occur. The affinity of an IgBD to bind to Ig molecules may lie below $10^{-6}$M, often below $10^{-7}$ M, or even below $10^{-8}$ M. Typically, IgBDs are derived from Ig binding proteins of gram-positive bacteria. These include but are not limited to Protein A from *Staphylococcus aureus*, streptococcal Protein G, and Protein L from *Peptostreptococcus magnus* (now: *Finegoldia magna*).

"Protein A (SpA)" is a 40-60 kDa surface protein originally found in the cell wall of *Staphylococcus aureus*. It binds immunoglobulins, most notably IgGs, from many mammalian species through an interaction of two α-helices of its IgBDs (A, B, C, D, E) with the $C_H2$ and $C_H3$ domains in the Fc fragment of an Ig molecule. Protein A binds with high affinity to human IgG1 and IgG2 as well as mouse IgG2a and IgG2b but only with moderate affinity to human IgM, IgA and IgE as well as to mouse IgG3 and IgG1.

"Protein G (SpG)" is an immunoglobulin-binding protein expressed in group C and G streptococcal strains which is similar to Protein A but exhibits different specificities. It is a cell surface protein of about 65-kDa that binds to the Fc region of IgG molecules (in particular to IgG1, IgG2 or IgG4) as well as to serum albumin. The amino acid sequences of the individual IgBDs are identical from streptococcal strains G148, GX7805, and GX7809 (Guss et al. (1986) EMBO J. 5:1567-1575). Protein G consists of repetitively arranged domains with the C-terminal domains (C1, C2, C3, also referred to as domains B1-B3) being responsible for IgG binding and the domains in the N-terminal half of the protein (domains A1, A2, A3) binding to serum albumin. The single IgBDs of Protein G show a common secondary structure consisting of a central α-helix packed against a four-stranded, antiparallel-parallel-antiparallel β-sheet. The amino acid sequences of domains C1 and C2 are 90% and 93%, respectively, identical to the sequence of domain C3. The amino acid sequences of Ig-binding domains C1, C2, and C3 of streptococcal Protein G are as followed:

SpG-C1:
(SEQ ID NO: 16)
TYKLILNGKTLKGETTTEAVDAATAEKVFKQYANDNGVDGEWTYDDATKT
FTVTE

SpG-C2:
(SEQ ID NO: 17)
TYKLVINGKTLKGETTTEAVDAATAEKVFKQYANDNGVDGEWTYDDATKT
FTVTE

SpG-C3:
(SEQ ID NO: 1)
TYKLVINGKTLKGETTTKAVDAETAEKAFKQYANDNGVDGVWTYDDATKT
FTVTE

Whilst in most streptococcal strains Protein G comprises all three Ig-binding domains (C1-C3), some stains contain a Protein G only comprising two Ig-binding domains. Exemplified, streptococcal strain GX7809 contains a Protein G with only two Ig-binding domains, wherein the first domain is identical to C1 of G148 and GX7805 and the last domain identical to C3 of G148 and GX7805.

The interaction between the IgBD of Protein G, in particular the C1 and C2 domains of SpG, and the Fc fragment of an immunoglobulin is mediated by the α-helix and the third β-strand within the IgBD (Gronenborn & Clore (1993) J. Mol. Biol. 233:331-335). The C3 domain interacts with the Fab fragment of an Ig molecule by binding to the surface exposed region of the $C_H1$ domain of the Ig molecule. This interaction of the C3 domain with the Fab fragment is mediated through an antiparallel alignment of the second β-strand from domain C3 with the seventh β-strand from the $C_H1$ domain of the Ig molecule which affects the extension of the four stranded β-sheet of domain C3 into the $C_H1$ domain (Derrick & Wigley (1994) J. Mol. Biol. 243:906-918). More specifically, the C3 domain interacts with the amino acid positions 122-127 and/or 207-214 of the $C_H1$ domain according to the EU index as in Kabat (see FIG. 1).

Unlike Protein A and Protein G, which bind to the heavy chain of immunoglobulins, "Protein L (PpL)" from *Peptostreptococcus magnus* binds through light chain interactions to those Ig molecules that contain kappa light chains. In the process PpL does not interfere with the antigen-binding site of the Ig molecule. Protein L binds to representatives of all antibody classes, including IgG, IgM, IgA, IgE and IgD as well as to scFv and Fab fragments.

The availability of a substance (for example a metabolite, drug, signaling molecule, radioactive nuclide, or other substance) in the body is dependent on several factors, such as its concentration in the blood plasma and the speed of its clearance from the body. The overall persistence of a substance in the body, i.e. the length of time a substance spends in the body, is expressed as the "mean resistance time (MRT)". The MRT depends on various factors such as the individual's body size, the rate at which the substance moves through and react within the body, and if applicable the amount of a substance, e.g. a pharmaceutical, administered. The MRT is also dependent on the overall ability of the body to eliminate a certain substance, e.g. a drug, from the plasma. In mammals, plasma clearance is achieved by the main clearing organs: the kidney and the liver. The term "plasma clearance" as used herein thus, refers to the volume of plasma that is cleared of a certain substance in a given time and is measured in units of a volumetric flow rate (volume/time).

The time it takes for the blood concentration of a substance to fall by one half is referred to as the "plasma half-life" or the "serum half-life" of a substance, irrespective of the factors (e.g. plasma clearance, absorbance by the tissue) which cause the decrease in concentration. The term "plasma" refers to the complete soluble fraction of the blood, whilst the term "serum" refers to plasma devoid of coagulation factors, i.e. obtained after coagulation of blood. Both, the plasma half-life and the serum half-life are measured as concentration in the blood.

A differentiation may be made between the initial and the terminal plasma or serum half-life of a substance. The terms "initial plasma half-life" (or "initial serum half-life") and "distribution plasma half-life" (or "distribution serum half-life") are used interchangeably herein and are abbreviated as $t_2\alpha$. The initial plasma half-life refers to the phase of rapid drug disappearance from the blood which occurs immediately after the dose is given, and which may lead to a very substantial decrement in drug concentrations in the blood. This initial phase of rapid drug disappearance is determined mainly by reversible distribution of drug out of the "central" compartment, of which the vascular system is a component, into storage sites in peripheral tissues; very little of this initial rapid decline is determined by elimination or clearance. Typically, the initial phase lasts from a few minutes (i.e. 1, 2, 3, 4, 5, 6, 7, 8, 9, or 10 min) to a few hours (i.e. 1, 2, 3, 4, 5, 6, 7, 8, 9, or 10 hours).

The terms "terminal plasma half-life" (or "terminal serum half-life") or "elimination plasma half-life" (or "elimination serum half-life") are used interchangeably herein and are abbreviated as $t_{1/2}\beta$. The elimination plasma half-life is generally determined only after drug distribution equilibrium has been attained, i.e. after the distribution of the administered substance in the various body tissues is complete. The blood concentration curve enters a less rapid phase of drug disappearance, termed the elimination phase, during which drug disappearance is determined mainly by irreversible clearance. Accordingly, the terminal plasma half-life ($t_{1/2}\beta$) is determined by clearance (CL) and volume of distribution ($V_D$) and the relationship is described by the following equation:

$$t_{1/2} = \frac{\ln 2 \cdot V_D}{CL}$$

Depending on the substance in question, the relationship between the initial plasma half-life and the terminal plasma half-life of such substance may be complex, taking into account factors including its accumulation in the tissues and receptor interactions (Toutain & Bousquet-Melou (2004) J. Vet. Pharmacol. Therap. 27:427-439). Both, the initial plasma half-life (or "initial serum half-life") and the terminal plasma half-life (or "terminal serum half-life") of a substance, e.g. a pharmaceutical, can be influenced in order to extend the bioavailability of such substance in the body. The bioavailability of a substance may be determined by measuring the concentration of said substance in the blood (plasma or serum) at certain time intervals after administration and establishing the area under the concentration-time-curve. The value of the "Area under the curve (AUC)" is proportional to the amount of the substance being available in the bloodstream.

Exemplified, the reduction of plasma clearance, e.g. by increasing the hydrodynamic volume of such substance to reduce renal clearance or by utilizing recycling processes via the FcRn, may lead to a prolonged terminal plasma half-life of the respective substance and thereby to an increased bioavailability in the body.

In the context of the present application it is preferred that the serum half-life, preferably the terminal serum half-life, of a pharmaceutically active moiety can be prolonged by reducing its plasma clearance and allowing for its recycling via the FcRn by complexing the pharmaceutically active moiety to an IgBD, preferably the C3 IgBD of streptococcal Protein G as described in detail above. The terms "prolonged" and "extended" or "prolongation" and "extension" are used interchangeably herein referring to an increase in the length of time, preferably in the lengths of the serum half-life, in particular the initial and/or terminal serum half-life.

The term "pharmaceutically active moiety" as used herein, is understood to refer to a part or moiety of a complex which mediates a pharmaceutical effect including but not limited to prophylactic, therapeutic, and/or diagnostic effects.

As used herein, "prevent", "preventing", "prevention", or "prophylaxis" of a disease or disorder means preventing that such disease or disorder occurs in a patient. Accordingly, a moiety having a prophylactic effect prevents the onset of a disease or disorder in a patient.

As used herein, "treat", "treating", "treatment" or "therapy" of a disease or disorder means accomplishing one or more of the following: (a) reducing the severity of the disorder; (b) limiting or preventing development of symptoms characteristic of the disorder(s) being treated; (c) inhibiting worsening of symptoms characteristic of the disorder(s) being treated; (d) limiting or preventing recurrence of the disorder(s) in an individual that has previously had the disorder(s); and (e) limiting or preventing recurrence of symptoms in individuals that were previously symptomatic for the disorder(s). Accordingly, a moiety having a therapeutic effect treats the symptoms of a disease or disorder by accomplishing one or more of above named effects (a)-(e).

The terms "identify", "identifying", "identification" or "diagnosis" of a disease or disorder are used herein to refer to the determination of the nature and the cause of a disease or disorder. Accordingly, a moiety having a diagnostic effect allows for the determination of the nature and the cause of a disease or disorder.

"Symptoms" of a disease or disorder are implication of the disease or disorder noticeable by the tissue, organ or organism having such disease or disorder and include but are not limited to pain, weakness, tenderness, strain, stiffness, and spasm of the tissue, an organ or an individual as well as the presence, absence, increase, decrease, of specific indicators such as biomarkers or molecular markers. The term "disease" and "disorder" as used herein, refer to an abnormal condition, especially an abnormal medical condition such as an illness or injury, wherein a tissue, an organ or an individual is not able to efficiently fulfil its function anymore. Typically, but not necessarily, a disease or disorder is associated with specific symptoms or signs indicating the presence of such disease or disorder.

A pharmaceutically active moiety typically comprises a biological and/or chemical pharmaceutical. "Chemical pharmaceuticals" are typically understood to refer to chemical compounds synthesized artificially which are effective in the prevention, treatment or diagnosis of disorders or diseases. "Biologicals" are typically understood to refer to medical drugs produced using biotechnological means and are used for prophylactic, therapeutic, and/or in vivo diagnostic purposes. Biologicals include but are not limited to peptides, polypeptides, proteins and nucleic acids (e.g. DNA, RNA, or hybrids thereof). Approved therapeutic biologicals include but are not limited to hormones (e.g. insulin, hGH, FSH, Glucagon-like peptide 1, parathyroid hormone, calcitonin, lutropin, glucagon), growth factors (e.g. erythropoietin, G-CSF/GM-CSF, IGF-1), interferons (e.g. IFN-α, IFN-β, IFN-γ), interleukins (e.g. IL-2, IL-11, IL-1Ra), coagulation factors (e.g. factor VIII, factor IX, factor VIIa, thrombin), thrombolytics and anti-coagulants (e.g. t-PA, hirudin, activated protein C), enzymes (e.g. α-glucosidase, glucocerebrosidase, iduronate-2-sulfatase, galactosidase, urate oxidase, DNase), antigen-binding molecule such as antibodies and antibody fragments (e.g. IgG, Fab), and fusion proteins thereof (e.g. TNFR2-Fc, TMP-Fc, CTLA-4-Fc, IL-1R-Fc, LFA-3-Fc, IL-2-DT).

A "peptide linker" (or short: "linker") in the context of the present invention refers to an amino acid sequence which sterically separates two parts or moieties of a complex, e.g. two peptides or proteins. Typically such linker consists of between 1 and 100 amino acids having a minimum length of at least 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 amino acids, and a maximum length of at least 100, 95, 90, 85, 80, 75, 70, 65, 60, 55, 50, 45, 40, 35, 34, 33, 32, 31, 30, 29, 28, 27, 26, 25, 24, 23, 22, 21, 20, 19, 18, 17, 16, or 15 amino acids or less. The indicated preferred minimum and maximum lengths of the peptide linker according to the present invention may be combined, if such a combination makes mathematically sense, e.g. such linker may consist of 1-15, or 12-40, or 25-75, or 1-100 amino acids. Peptide linkers may also provide flexibility among the two moieties that are linked together. Such flexibility is generally increased if the amino acids are small. Accordingly, flexible peptide linkers comprise an increased content of small amino acids, in particular of glycins and/or alanines, and/or hydrophilic amino acids such as serines, threonines, asparagines and glutamines. Preferably, more than 20%, 30%, 40%, 50%, 60% or more of the amino acids of the peptide linker are small amino acids.

The term "cleavage site" as used herein refers to an amino acid sequence or nucleotide sequence wherein this sequence directs the division of a complex or a macromolecule (e.g. a nucleic acid or a protein), e.g. because it is recognized by a cleaving enzyme, and/or can be divided. Typically, a polypeptide chain is cleaved by hydrolysis of one or more peptide bonds that link the amino acids and a polynucleotide chain is cleaved by hydrolysis of one or more of the phosphodiester bond between the nucleotides. Cleavage of peptide- or phosphodiester-bonds may originate from chemical or enzymatic cleavage. Enzymatic cleavage refers to such cleavage being attained by proteolytic enzymes including but not limited to restriction endonuclease (e.g. type I, type II, type II, type IV or artificial restriction enzymes) and endo- or exo-peptidases or -proteases (e.g. serine-proteases, cysteine-proteases, metallo-proteases, threonine proteases, aspartate proteases, glutamic acid proteases). Typically, enzymatic cleavage occurs due to self-cleavage or is affected by an independent proteolytic enzyme. Enzymatic cleavage of a protein or polypeptide can happen either co- or post-translational. Accordingly, the term "endopeptidase cleavage site" used herein, refers to a cleavage cite within the amino acid or nucleotide sequence where this sequence is cleaved or is cleavable by an endopeptidase (e.g. trypsin, pepsin, elastase, thrombin, collagenase, furin, thermolysin, endopeptidase V8, cathepsins).

The term "self-cleavage site" as used herein refers to a cleavage site within the amino acid sequence where this sequence is cleaved or is cleavable without such cleavage involving any additional molecule. It is understood that cleavage sites typically comprise several amino acids. Thus, the cleavage site may also serve the purpose of a peptide linker, i.e. sterically separating two peptides or proteins.

As used herein, the term "vector" refers to a protein or a polynucleotide or a mixture thereof which is capable of being introduced or of introducing the proteins and/or nucleic acid comprised therein into a cell. In the context of the present invention it is preferred that the genes of interest encoded by the introduced polynucleotide are expressed within the cell upon introduction of the vector or vectors. Examples of suitable vectors include but are not limited to plasmids, cosmids, phages, viruses or artificial chromosomes.

The terms "pharmaceutical", "medicament" and "drug" are used interchangeably herein, referring to a substance and/or a combination of substances being used for the identification, prevention or treatment of a disease or disorder.

The terms "preparation" and "composition" are intended to include the formulation of the active compound with encapsulating material as a carrier providing a capsule in which the active component with or without other carriers, is surrounded by a carrier, which is thus in association with the active compound.

"Pharmaceutically acceptable" means approved by a regulatory agency of the Federal or a state government or listed in the U.S. Pharmacopeia or other generally recognized pharmacopeia for use in animals, and more particularly in humans.

The term "active ingredient" refers to the substance in a pharmaceutical composition or formulation that is biologically active, i.e. that provides pharmaceutical value. A pharmaceutical composition may comprise one or more active ingredients which may act in conjunction with or independently of each other. The active ingredient can be formulated as neutral or salt forms. Pharmaceutically acceptable salts include those formed with free amino groups such as but not limited to those derived from hydrochloric, phosphoric, acetic, oxalic, tartaric acids, etc., and those formed with free carboxyl groups such as but not limited to those derived from sodium, potassium, ammonium, calcium, ferric hydroxides, isopropylamine, triethylamine, 2-ethylamino ethanol, histidine, procaine, and the like.

The term "carrier", as used herein, refers to a pharmacologically inactive substance such as but not limited to a diluent, excipient, surfactants, stabilizers, physiological buffer solutions or vehicles with which the therapeutically active ingredient is administered. Such pharmaceutical carriers can be liquid or solid. Liquid carrier include but are not limited to sterile liquids, such as saline solutions in water and oils, including but not limited to those of petroleum, animal, vegetable or synthetic origin, such as peanut oil, soybean oil, mineral oil, sesame oil and the like.

Saline solutions and aqueous dextrose and glycerol solutions can also be employed as liquid carriers, particularly for injectable solutions. A saline solution is a preferred carrier when the pharmaceutical composition is administered intravenously. Examples of suitable pharmaceutical carriers are described in "Remington's Pharmaceutical Sciences" by E. W. Martin.

Suitable pharmaceutical "excipients" include starch, glucose, lactose, sucrose, gelatine, malt, rice, flour, chalk, silica gel, sodium stearate, glycerol monostearate, talc, sodium chloride, dried skim milk, glycerol, propylene, glycol, water, ethanol and the like.

"Surfactants" include anionic, cationic, and non-ionic surfactants such as but not limited to sodium deoxycholate, sodium dodecylsulfate, Triton X-100, and polysorbates such as polysorbate 20, polysorbate 40, polysorbate 60, polysorbate 65 and polysorbate 80. "Stabilizers" include but are not limited to mannitol, sucrose, trehalose, albumin, as well as protease and/or nuclease antagonists.

"Physiological buffer solution" include but are not limited to sodium chloride solution, demineralized water, as well as suitable organic or inorganic buffer solutions such as but not limited to phosphate buffer, citrate buffer, tris buffer (tris (hydroxymethyl)aminomethane), HEPES buffer ([4 (2 hydroxyethyl)piperazino]ethanesulphonic acid) or MOPS buffer (3 morpholino-1 propanesulphonic acid). The choice of the respective buffer in general depends on the desired buffer molarity. Phosphate buffer are suitable, for example, for injection and infusion solutions.

The term "adjuvant" refers to agents that augment, stimulate, activate, potentiate, or modulate the immune response to the active ingredient of the composition at either the cellular or humoral level, e.g. immunologic adjuvants stimulate the response of the immune system to the actual antigen, but have no immunological effect themselves. Examples of such adjuvants include but are not limited to inorganic adjuvants (e.g. inorganic metal salts such as aluminium phosphate or aluminium hydroxide), organic adjuvants (e.g. saponins or squalene), oil-based adjuvants (e.g. Freund's complete adjuvant and Freund's incomplete adjuvant), cytokines (e.g. IL-1β, IL-2, IL-7, IL-12, IL-18, GM-CFS, and INF-γ) particulate adjuvants (e.g. immuno-stimulatory complexes (ISCOMS), liposomes, or biodegradable microspheres), virosomes, bacterial adjuvants (e.g. monophosphoryl lipid A, or muramyl peptides), synthetic adjuvants (e.g. non-ionic block copolymers, muramyl peptide analogues, or synthetic lipid A), or synthetic polynucleotides adjuvants (e.g polyarginine or polylysine).

An "effective amount" or "therapeutically effective amount" is an amount of a therapeutic agent sufficient to achieve the intended purpose. The effective amount of a given therapeutic agent will vary with factors such as the nature of the agent, the route of administration, the size and species of the animal to receive the therapeutic agent, and the purpose of the administration. The effective amount in each individual case may be determined empirically by a skilled artisan according to established methods in the art.

Embodiments

In a first aspect the present invention relates to a complex comprising (i) an immunoglobulin (Ig) binding moiety and (ii) a pharmaceutically active moiety, wherein the Ig binding moiety specifically binds to the constant domain 1 of the heavy chain ($C_H1$) of an Ig molecule.

In preferred embodiments, the Ig binding moiety prolongs the serum half-life of the pharmaceutically active moiety, i.e. the pharmaceutically active moiety exhibits a prolonged serum half-life when being part of the complex of the first aspect of the invention. In preferred embodiments the complex of the first aspect is thus, used for extending the serum half-life, preferably the serum half-life of the pharmaceutically active moiety. It is particularly preferred that the initial and/or the terminal serum half-life are extended. It is further preferred that the bioavailabilty, more preferably the bioavailabilty of the pharmaceutically active moiety, is increased.

In the context of the present invention it is preferred that the Ig binding moiety binds to mammalian, avian, fish or reptile Ig, in particular to Igs of laboratory animals including but not limited to mouse, rat and rabbit, and/or domestic animals including but not limited to guinea pig, rabbit, horse, donkey, camel, cow, sheep, goat, pig, chicken, duck, goose, parrot, canary bird, cat, dog, goldfish, trout, pangasius, carp, koi, perch, catfish, salmon, turtle, tortoise, snake, and lizard, and/or primates including but not limited to gibbons, lemurs, chimpanzees, bonobos, gorillas, and human beings. It is particularly preferred that the Ig binding moiety binds to the Ig of human beings. Preferably, the binding of the Ig binding moiety to the Ig molecule occurs in vivo, i.e. within the body of a mammal, bird, fish, or reptile, in particular within the body of a mammal, bird, fish, or reptile as specified above. Accordingly, preferably, the Ig binding moiety binds to an Ig molecule in vivo.

In further embodiments of the present invention, the Ig binding moiety binds to IgA, IgD, IgE, IgG, and/or IgM, preferably to an IgG of subclasses IgG1, IgG2, IgG3, and/or IgG4, more preferably to IgG, IgG2, and/or IgG4.

The Ig binding moiety preferably binds to the Fab fragment and/or the Fc portion of an immunoglobulin molecule. It is particularly preferred that the Ig binding moiety binds to the Fab portion of an Ig molecule, and that it optionally also binds to the Fc fragment. Thus, in preferred embodiments, the Ig binding moiety has a structure allowing for the binding to both, the Fc portion and the Fab portion of an immunoglobulin molecule (e.g. as illustrated in FIG. 1b). In further preferred embodiments the Ig binding moiety has a structure allowing for the binding to either the Fc portion or the Fab portion of an immunoglobulin molecule (e.g. as illustrated in FIG. 1c for a Fab-binding Ig binding moiety). Preferably, the ability to bind to only one of the Fc portion or the Fab portion of an immunoglobulin molecule is due to the functional inactivation (e.g. the structural deletion of all or parts of the Fab- or Fc-binding site, or the functional inactivation via amino acid deletions, replacements, additions, mutations or exchanges) of the respective binding site of Ig binding moiety via genetic engineering. In preferred embodiments, the Ig binding moiety has an affinity to bind to an Ig molecule at neutral pH (i.e. pH 7), preferably with an affinity of below $10^{-6}$ to below $10^{-9}$ M, i.e. with an affinity of below $10^{-6}$ below $10^{-7}$ M, below $10^{-8}$ M, or below $10^{-9}$ M. It is particularly preferred that the Ig binding moiety binds to the Fab fragment of an Ig molecule with an affinity of $10^{-7}$ M to $10^{-6}$ M (i.e. with an affinity of $1\times10^{-7}$ M, $1.1\times10^{-7}$ M, $1.2\times10^{-7}$ M, $1.3\times10^{-7}$ M, $1.4\times10^{-7}$ M, $1.5\times10^{-7}$ M, $1.6\times10^{-7}$ M, $1.7\times10^{-7}$ M, $1.8\times10^{-7}$ M, $1.9\times10^{-7}$ M, $2\times10^{-7}$ M, $2.1\times10^{-7}$ M, $2.2\times10^{-7}$ M, $2.3\times10^{-7}$ M, $2.4\times10^{-7}$ M, $2.5\times10^{-7}$ M, $2.6\times10^{-7}$ M, $2.7\times10^{-7}$ M, $2.8\times10^{-7}$ M, $2.9\times10^{-7}$ M, $3\times10^{-7}$ M, $3.1\times10^{-7}$ M, $3.2\times10^{-7}$ M, $3.3\times10^{-7}$ M, $3.4\times10^{-7}$ M, $3.5\times10^{-7}$ M, $3.6\times10^{-7}$ M, $3.7\times10^{-7}$ M, $3.8\times10^{-7}$ M, $3.9\times10^{-7}$ M, $4\times10^{-7}$ M, $4.1\times10^{-7}$ M, $4.2\times10^{-7}$ M, $4.3\times10^{-7}$ M, $4.4\times10^{-7}$ M, $4.5\times10^{-7}$ M, $4.6\times10^{-7}$ M, $4.7\times10^{-7}$ M, $4.8\times10^{-7}$ M, $4.9\times10^{-7}$ M, $5\times10^{-7}$ M, $5.1\times10^{-7}$ M, $5.2\times10^{-7}$ M, $5.3\times10^{-7}$ M, $5.4\times10^{-7}$ M, $5.5\times10^{-7}$ M, $5.6\times10^{-7}$ M, $5.7\times10^{-7}$ M, $5.8\times10^{-7}$ M, $5.9\times10^{-7}$ M, $6\times10^{-7}$ M, $6.1\times10^{-7}$ M, $6.2\times10^{-7}$ M, $6.3\times10^{-7}$ M, $6.4\times10^{-7}$ M, $6.5\times10^{-7}$ M, $6.6\times10^{-7}$ M, $6.7\times10^{-7}$ M, $6.8\times10^{-7}$ M, $6.9\times10^{-7}$ M, $7\times10^{-7}$ M, $7.1\times10^{-7}$ M, $7.2\times10^{-7}$ M, $7.3\times$ $10^{-7}$ M, $7.4 \times 10^{-7}$ M, $7.5 \times 10^{-7}$ M, $7.6 \times 10^{-7}$ M, $7.7 \times 10^{-7}$ M, $7.8 \times 10^{-7}$ M, $7.9 \times 10^{-7}$ M, $8 \times 10^{-7}$ M, $8.1 \times 10^{-7}$ M, $8.2 \times 10^{-7}$ M, $8.3 \times 10^{-7}$ M, $8.4 \times 10^{-7}$ M, $8.5 \times 10^{-7}$ M, $8.6 \times 10^{-7}$ M, $8.7 \times 10^{-7}$ M, $8.8 \times 10^{-7}$ M, $8.9 \times 10^{-7}$ M, $9 \times 10^{-7}$ M, $9.1 \times 10^{-7}$ M, $9.2 \times 10^{-7}$ M, $9.3 \times 10^{-7}$ M, $9.4 \times 10^{-7}$ M, $9.5 \times 10^{-7}$ M, $9.6 \times 10^{-7}$ M, $9.7 \times 10^{-7}$ M, $9.8 \times 10^{-7}$ M, $9.9 \times 10^{-7}$ M, or $1 \times 10^{-6}$ M) and/or to the the Fc portion of an Ig molecule with an affinity of $10^{-8}$ M to $10^{-7}$ M (i.e. with an affinity of $1 \times 10^{-8}$ M, $1.1 \times 10^{-8}$ M, $1.2 \times 10^{-8}$ M, $1.3 \times 10^{-8}$ M, $1.4 \times 10^{-8}$ M, $1.5 \times 10^{-8}$ M, $1.6 \times 10^{-8}$ M, $1.7 \times 10^{-8}$ M, $1.8 \times 10^{-8}$ M, $1.9 \times 10^{-8}$ M, $2 \times 10^{-8}$ M, $2.1 \times 10^{-8}$ M, $2.2 \times 10^{-8}$ M, $2.3 \times 10^{-8}$ M, $2.4 \times 10^{-8}$ M, $2.5 \times 10^{-8}$ M, $2.6 \times 10^{-8}$ M, $2.7 \times 10^{-8}$ M, $2.8 \times 10^{-8}$ M, $2.9 \times 10^{-8}$ M, $3 \times 10^{-8}$ M, $3.1 \times 10^{-8}$ M, $3.2 \times 10^{-8}$ M, $3.3 \times 10^{-8}$ M, $3.4 \times 10^{-8}$ M, $3.5 \times 10^{-8}$ M, $3.6 \times 10^{-8}$ M, $3.7 \times 10^{-8}$ M, $3.8 \times 10^{-8}$ M, $3.9 \times 10^{-8}$ M, $4 \times 10^{-8}$ M, $4.1 \times 10^{-8}$ M, $4.2 \times 10^{-8}$ M, $4.3 \times 10^{-8}$ M, $4.4 \times 10^{-8}$ M, $4.5 \times 10^{-8}$ M, $4.6 \times 10^{-8}$ M, $4.7 \times 10^{-8}$ M, $4.8 \times 10^{-8}$ M, $4.9 \times 10^{-8}$ M, $5 \times 10^{-8}$ M, $5.1 \times 10^{-8}$ M, $5.2 \times 10^{-8}$ M, $5.3 \times 10^{-8}$ M, $5.4 \times 10^{-8}$ M, $5.5 \times 10^{-8}$ M, $5.6 \times 10^{-8}$ M, $5.7 \times 10^{-8}$ M, $5.8 \times 10^{-8}$ M, $5.9 \times 10^{-8}$ M, $6 \times 10^{-8}$ M, $6.1 \times 10^{-8}$ M, $6.2 \times 10^{-8}$ M, $6.3 \times 10^{-8}$ M, $6.4 \times 10^{-8}$ M, $6.5 \times 10^{-8}$ M, $6.6 \times 10^{-8}$ M, $6.7 \times 10^{-8}$ M, $6.8 \times 10^{-8}$ M, $6.9 \times 10^{-8}$ M, $7 \times 10^{-8}$ M, $7.1 \times 10^{-8}$ M, $7.2 \times 10^{-8}$ M, $7.3 \times 10^{-8}$ M, $7.4 \times 10^{-8}$ M, $7.5 \times 10^{-8}$ M, $7.6 \times 10^{-8}$ M, $7.7 \times 10^{-8}$ M, $7.8 \times 10^{-8}$ M, $7.9 \times 10^{-8}$ M, $8 \times 10^{-8}$ M, $8.1 \times 10^{-8}$ M, $8.2 \times 10^{-8}$ M, $8.3 \times 10^{-8}$ M, $8.4 \times 10^{-8}$ M, $8.5 \times 10^{-8}$ M, $8.6 \times 10^{-8}$ M, $8.7 \times 10^{-8}$ M, $8.8 \times 10^{-8}$ M, $8.9 \times 10^{-8}$ M, $9 \times 10^{-8}$ M, $9.1 \times 10^{-8}$ M, $9.2 \times 10^{-8}$ M, $9.3 \times 10^{-8}$ M, $9.4 \times 10^{-8}$ M, $9.5 \times 10^{-8}$ M, $9.6 \times 10^{-8}$ M, $9.7 \times 10^{-8}$ M, $9.8 \times 10^{-8}$ M, $9.9 \times 10^{-8}$ M, or $1 \times 10^{-7}$ M).

In preferred embodiments the Ig binding moiety specifically binds to the surface-exposed region of the CH1 domain of an Ig molecule. The term "surface exposed region of an Ig molecule" preferably refers to those amino acids of an Ig molecule, which are free to specifically interact with a binding moiety, if the binding moiety and the Ig molecule are in solution, preferably in a physiological solution. Preferably the "surface exposed regions" of an Ig molecule are those, which can elicit an immune response, preferably a B cell specific immune response. Preferred is the surface-exposed region of the CH1 domain of an IgG molecule.

Preferably, the Ig binding moiety interacts with the seventh β-stand of the CH1 domain of the Ig molecule. It is particularly preferred that the Ig binding moiety specifically binds to an epitope formed by amino acid positions 122-127 and/or 207-214 of an Ig molecule according to EU index as in Kabat (see FIG. 12). Preferably, the Ig binding moiety specifically binds to an epitope formed by amino acid positions 122-127 and/or 207-214 according to EU index as in Kabat of an human Ig γ1 according to SEQ ID NO: 4, human Ig γ2 according to SEQ ID NO: 5, human Ig γ3 according to SEQ ID NO: 6, human Ig γ4 according to SEQ ID NO: 7, mouse Ig γ1 according to SEQ ID NO: 8, mouse Ig γ2a according to SEQ ID NO: 9, mouse Ig γ2b according to SEQ ID NO: 10, mouse Ig γ3 according to SEQ ID NO: 11, and/or rat γ1 according to SEQ ID NO: 12, or variants thereof. Preferably, the Ig binding moiety has an affinity to the CH1 domain of an Ig molecule, more preferably to the surface-exposed region of the CH1 domain of an IgG molecule of below $10^{-6}$ to below $10^{-9}$ M or the preferred affinities set out above in more detail.

In the context of the present invention, the Ig binding moiety preferably comprises an immunoglobulin binding domain (IgBD). Preferably, the IgBD is derived from an Ig binding protein of gram-positive bacteria, more preferably the IgBD is a *streptococcus*-derived IgBD. In preferred embodiments, the Ig binding moiety comprises a CH1 binding-IgBD, preferably of a streptococcal strain, more preferably a CH1 binding-IgBD of streptococcal protein G.

It is further preferred that the Ig binding moiety comprises the C3 IgBD of streptococcal protein G (the abbreviations "SpG-C3" or "SpG$_{C3}$", are used interchangeably herein), more preferably comprising an amino acid sequence according to SEQ ID NO: 1 or variants thereof. In preferred embodiments variants comprise an amino acid sequence of at least 70% identity to the amino acid sequence of SpG-C3, preferably of SEQ ID NO: 1, i.e. comprise an amino acid sequence of at least 70%, of at least 71%, of at least 72% of at least 73% of at least 74%, of at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, or at least 98% to the amino acid sequence according to SEQ ID NO: 1. In particularly preferred embodiments, variants comprise an amino acid sequence of at least 94% identity to the amino acid sequence of SpG-C3, preferably of SEQ ID NO: 1, i.e. comprise an amino acid sequence of at least 94%, at least 95%, at least 96%, at least 97%, or at least 98% to the amino acid sequence according to SEQ ID NO: 1. Thus, it is preferred that variants of SpG-C3, preferably of SEQ ID NO: 1, have between 1 and 14 amino acids substitutions, deletions and/or insertions, e.g. 1, 2, 3, 4, 5, 6, 7, 8, 9, 10, 11, 12, 13 or 14 substitutions, deletions and/or insertions.

It is preferred that the plasma half-life, preferably the initial and/or the terminal plasma half-life, or the serum half-life, preferably the initial and/or the terminal serum half-life, of the variant is not altered with respect to the naturally occurring $C_H1$-binding IgBD, preferably the Ig binding protein of a gram-positive bacteria, on which the variant is based. In further preferred embodiments, the plasma half-life, preferably the initial and/or the terminal plasma half-life; or the serum half-life, preferably the initial and/or the terminal serum half-life, of the var the active compound iant is increased with respect to the naturally occurring $C_H1$-binding IgBD on which the variant is based. Preferably, the plasma half-life, more preferably the initial and/or the terminal plasma half-life; or serum half-life, more preferably the initial and/or the terminal serum half-life, is increased by at least 10%, at least 20%, at least 30%, at least 40%, at least 50%, at least 60%, at least 70%, more preferably by at least 80%.

It is also preferred that the bioavailability of the variant is not altered with respect to the naturally occurring $C_H1$-binding IgBD. It is further preferred that the bioavailability of the variant is increased with respect to the naturally occurring $C_H1$-binding IgBD. Preferably, the bioavailability of the variant is increased by at least 10%, at least 20%, at least 30%, at least 40%, at least 50%, at least 60%, at least 70%, more preferably by at least 80%.

In preferred embodiments such variant comprises amino acid exchanges, insertions, deletions, or N- or C-terminal truncations, or any combination of these changes, which may occur at one or several sites. Optionally such variants may alter the binding properties of the IgBD, preferably by increasing the binding affinity of the IgBD to the Ig molecule. An increased binding affinity to an Ig molecule may be achieved by preventing the binding of the IgBD to the Fc- or the Fab-fragment ("C3-Fc" or "C3-Fab", respectively), e.g. by exchanging one or more amino acid positions to contain the amino acid alanine. Preferably, the Fab-binding of the C3 IgBD of streptococcal protein G is prohibited by the amino acid exchanges Thr10Ala, Lys12Ala, and Glu14Ala, as shown in SEQ ID NO: 2 (C3-Fc). The Fc-binding of the C3 IgBD of streptococcal protein G is prohibited by the amino acid exchanges Glu26Ala, Lys27Ala, and Lys30Ala, as shown in SEQ ID NO: 3 (C3-Fab).

In embodiments of the first aspect of the present invention, the pharmaceutically active moiety comprises a biological and/or chemical pharmaceutical. Preferably, the pharmaceutically active moiety comprises a biological such as but not limited to pharmaceutically, preferably therapeutically, active peptides, polypeptides, or proteins produced via biotechnological means. Suitable biologicals include but are not limited to hormones (e.g. insulin, hGH, FSH, Glucagon-like peptide 1, parathyroid hormone, calcitonin, lutropin, glucagon), blood factors (e.g. factor VIII, factor IX, factor XI), growth factors (e.g. erythropoietin, G-CSF/GM-CSF, IGF-1), interferons (e.g. IFN-α, IFN-β, IFN-γ), interleukins (e.g. IL-2, IL-11, IL-1Ra), coagulation factors (e.g. factor VIII, factor IX, factor VIIa, thrombin), thrombolytics and anti-coagulants (e.g. t-PA, hirudin, activated protein C), enzymes (e.g. α-glucosidase, glucocerebrosidase, iduronate-2-sulfatase, galactosidase, urate oxidase, DNase), vaccines (e.g. parasitic, fungal, bacterial, or viral antigens such as e.g. hepatitis B surface antigens), antigen-binding molecule such as antibodies and antibody fragments (e.g. IgG, Fab), and fusion proteins thereof (e.g. TNFR2-Fc, TMP-Fc, CTLA-4-Fc, IL-1R-Fc, LFA-3-Fc, IL-2-DT).

In preferred embodiments, the pharmaceutically active moiety does not comprise the N-terminal domain of the diphteria toxin, a cellulose-binding domain (CBD), diagnostic proteins, in particular a firefly luciferase and/or the green fluorescent protein (GFP) of *Aequorea victoria*. Diagnostic proteins are those, which are capable to fluoresce.

In the context of the present invention it is particularly preferred that the pharmaceutically active moiety comprises an antigen-binding molecule such as an immunoglobulin molecule. Preferably, the antigen-binding molecule is selected from the group consisting of an antibody fragment, a Fab fragment, a Fab' fragment, a F(ab')$_2$ fragment, a heavy chain antibody, a single-domain antibody (sdAb), a single-chain variable fragment (scFv), a di-scFv, a bispecific T-cell engager (BITEs), a diabody, a single-chain diabody, a DART molecule, a triple body, an alternative scaffold protein, and a fusion proteins thereof. In particularly preferred embodiments the antigen-binding molecule is a scFv or a diabody or a fusion protein comprising a scFv or a diabody. Preferably, the antigen-binding molecule does not comprise a cellulose-binding domain (CBD).

Additionally or alternatively, the antigen-binding molecule may further comprise a radioactive moiety, a cytotoxic drug, a chelating moiety, a photosensitizer, or an imaging reagent.

In preferred embodiments the antigen-binding molecule comprises a radioactive moiety, i.e. a radionuclide. The radioactive moiety may be an isotpe of F, Br, Mn, Co, Ga, As, Zr, P, C, S, H, I, In, Lu, Cu, Rh, Bi, At, Y, Re, Ac, Tc, or Hg atom. The radioactive moiety labels the antigen-binding molecule radioactively allowing for its detection, e.g in the human body, rendering it not only useful for diagnostic approaches (radioimmunodetection: RAID) but also suitable in therapeutic applications (radioimmunotherapy: RAIT).

Photosensitizers are chemical compounds capable of light emission or formation of free radicals and singlet oxygen after being excited by light of a specific wavelength. Photosensitizer are used e.g. for photodynamic therapy. In preferred embodiments photosenitizer include but are not limited to compounds of the porphyrin family, texaphyrin family, the chlorin family and the phthalocyanine family, in particular including HpD, ALA, M-ALA, Vertiporfin, Lutexaphyrin, Temoporfin, Talaporfin, HPPH, Phthalocyanine, and Napthalocyanine.

Imaging reagents include bioluminescent, chemiluminescent and fluorescent imaging reagent such as but not limited to luciferase from *Renilla reniformis* and/or *Metridia Longa*, peroxalate, polymethines (e.g. cyanine dyes such as Cy3, Cy5, Cy5.5, Cy7) squaraine derivatives, phthalocyanine, porphhyrin derivatives, and BODIPY analogous (BODIPY FL, BODIPY R6G, BODIPY TR, BODIPY TMR, BODIPY 581/591, BODIPY 630/650, BODIPY 650/665), as well as fluorescent proteins such as but not limited to CFP, BFP, YFP, DsRED (Chudakov et al. (2010) Physiol. Rev. 90:1103-1163). Preferably, the fluorescent protein is not GFP.

In preferred embodiments the antigen-binding molecule is a cytotoxic drug which has a toxic effect on cells such as but not limited to antimitotic drugs, drugs prohibiting cell growths and drugs causing cell death. Non-limiting examples of cytotoxic drugs are alkylating agents (e.g. cisplatin, carboplatin, oxaloplatin, mechlorethamine, cyclophosphamide, chlorambucil), anti-metabolites (5-fluorouracil (5-FU), capecitabine (Xeloda®), 6-mercaptopurine (6-MP), methotrexate, gemcitabine), plant alkaloids (e.g. ajmaline, atropine, scopolamine, hyoscyamine, vinca alkaloids, codeine cocaine colchicine morphine, reserpine, tubocurarine, physostigmine, quinidine, quinine, emetine, ergot alkaloids), antitumor antibiotics (e.g. actinomycin-D, bleomycin, and mitomycin-C, mitoxantrone, and anthracyclines such as daunorubicin, doxorubicin), topoisomerase inhibitors (e.g. topotecan, irinotecanetoposide (VP-16) and teniposide), and mitotic inhibitors (estramustine, taxanes such as paclitaxel and docetaxel, epothilones such as ixabepilone, and vinca alkaloids such as vinblastine, vincristine, vindesine and vinorelbine).

The antigen-binding molecule may further comprise a chelating moiety capable of binding at least one metal ion, such as but not limited to calcium, magnesium, iron, aluminium, zinc, copper, arsenic, lead, thallium, and mercury ions, by chelation. Such chelating moiety may comprise ethylenediamine tetraacetic acid (EDTA), ethylenediamine tetraacetic acid (calcium disodium versante) (CaNa$_2$-EDTA), dimercaprol (BAL), dimercaptosuccinic acid (DMSA), dimercapto-propane sulfonate (DMPS), ferritin, deferoxamine and deferasirox, deferiprone (1,2-dimethyl-3-hydroxyl-4-pyridinone), DOTA, DTPA, DADT, DADS, DO3A, N2S2MAMA, Triamidethiol, phosphonates, organic gadolinium complexes, penicillamine, and antibiotic drugs of the tetracycline family. A chelating moiety is of particular interest in chelating therapy, e.g. in the treatment of atherosclerosis, rheumatoid arthritis, and poisoning such as mercury poisoning, copper toxicity, gold toxicity, arsenic poisoning, lead poisoning, acute iron poisoning, and iron overload. Chelating moieties are also important for radiotherapy.

Preferably, the antigen binding molecule is a fusion protein, which additionally or alternatively further comprises a proapoptotic protein, an immuno-(co)stimulatory protein, immuno-suppressive protein, a cytokine (e.g. interleukins and/or interferons), a chemokine (e.g. an α-, β-, or γ-chemokine), a toxin, a growth factor or an enzyme, preferably a RNase, a prodrug-converting enzyme or a kinase (e.g. AGC kinases, CaM kinases, CK1 kinases, CMGC kinases, STE kinases, TK kinases, and TKL kinases).

In preferred embodiments proapoptotic protein include but are not limited to Bid, Bik, Puma, and Bim, and proapoptic cytokines (death ligands) such as but not limited to TNF, TRAIL, and FasL.

In preferred embodiments immuno-(co)stimulatory protein include but are not limited to B7.1, B7.2, 4-1BBL, LIGHT, ICOSL, GITR, CD40, OX40L, and CD70.

Immuno-suppressive proteins preferably include but are not limited to IL1-Ra and toxins preferably include but are not limited to *Pseudomonas* exotoxin A and ricin. Preferably, the toxin is not diphteria toxin.

In preferred embodiments, cytokines are interleukins and/or interferons. Interleukins (IL) include but are not limited to Interleukin-1, Interleukin-2, Interleukin-3, Interleukin-4, Interleukin-5, Interleukin-6, Interleukin-7, Interleukin-8, Interleukin-9, Interleukin-10, Interleukin-11, Interleukin 12, Interleukin-13, Interleukin-14, Interleukin-15, Interleukin-16, Interleukin-17, Interleukin-18, Interleukin-19, Interleukin-20, Interleukin-21, Interleukin-22, Interleukin-23, Interleukin-24, Interleukin-25, Interleukin-26 Interleukin-27, Interleukin-28, Interleukin-29, Interleukin-30, Interleukin-31, Interleukin-32, Interleukin-33, Interleukin-34 and Interleukin-35. Interferons (IFN) include but are not limited to interferon type I (e.g. IFN-α, IFN-β and IFN-ω), interferon type II (e.g. IFN-γ), and interferon type III. In particular included are interferon A1, interferon A2, interferon A4, interferon A5, interferon A6, interferon A7, interferon A8, interferon A10, interferon A13, interferon A14, interferon A16, interferon A17, interferon A21, interferon B1, TNF, TRAIL, and FasL.

In preferred embodiments growth factors include but are not limited to Adrenomedullin (AM), Angiopoietin (Ang), Autocrine motility factor, Bone morphogenetic proteins (BMPs), Brain-derived neurotrophic factor (BDNF), Epidermal growth factor (EGF), Erythropoietin (EPO), Fibroblast growth factor (FGF), Glial cell line-derived neurotrophic factor (GDNF), Granulocyte colony-stimulating factor (G-CSF), Granulocyte macrophage colony-stimulating factor (GM-CSF), Growth differentiation factor-9 (GDF9), Hepatocyte growth factor (HGF), Hepatoma-derived growth factor (HDGF), Insulin-like growth factor (IGF), Migration-stimulating factor Myostatin (GDF-8), Nerve growth factor (NGF) and other neurotrophins, Platelet-derived growth factor (PDGF), Thrombopoietin (TPO), Transforming growth factor alpha (TGF-α), Transforming growth factor beta (TGF-β), Vascular endothelial growth factor (VEGF), Wnt Signaling Pathway, and placental growth factor (PlGF).

RNAses include endoribonucleases such as but are not limited to RNase A, RNase H, RNase I, RNase III, RNase L, RNase P, RNase PhyM, RNase T1, RNase T2, RNase U2, RNase Vl, and RNase V, and exoribonucleases such as but not limited to Polynucleotide Phosphorylase (PNPase), RNase PH, RNase II, RNase R, RNase D, RNase T, Oligoribonuclease Exoribonuclease I, and Exoribonuclease II.

Pro-drug-converting enzymes include but are not limited to esterases such as but not limited to acetylesterase, thiolester hydrolases, phosphoric monoester hydrolases, phosphoric diester hydrolases, triphosphoric monoester hydrolases, sulfuric ester hydrolases (sulfatases), diphosphoric monoester hydrolases, and phosphoric triester hydrolases; phosphatases such as but not limited to tyrosine-specific phosphatases, serine/threonine specific phosphatases, dual specificity phosphatases, histidine phosphatase, and lipid phosphatase; and reductases such as but not limited to 5-alpha reductase, dihydrofolate reductase, HMG-CoA reductase, methemoglobin reductase, ribonucleotide reductase, thioredoxin reductase, *E. coli* nitroreductase, methylenetetrahydrofolate reductase, and carboxypeptidase G2, cytosine deaminase, nitroreductase, thymidine kinase.

Kinases include but are not limited to AGC kinases such as PKA, PKC and PKG, CaM kinases such as calcium/calmodulin-dependent protein kinases and serine/threonine protein kinases (e.g. DAPK2), CK1 such as the casein kinase 1 group, CMGC such as CDK, MAPK, GSK3 and CLK kinases, STE such as homologs of yeast Sterile 7, Sterile 11, and Sterile 20 kinases, tyrosine kinases (TK), the tyrosine-kinase like group of kinases (TKL), receptor-associated tyrosine kinases, MAP kinases, and histidine kinases.

In particularly preferred embodiments the pharmaceutically active moiety is a peptide-linked or a disulfide-linked single-chain diabody. It is particularly preferred that the pharmaceutically active moiety is a single-chain diabody with a first specificity (A) directed against a target molecule, and a second specificity (B) directed against an effector molecule. Preferably, the single-chain diabody comprises the structure [VH(A)-VL(B)-P-VH(B)-VL(A)] or [VL(B)-VH(A)-P-VL(A)-VH(B)]. In preferred embodiments the first specificity (A) is directed against a tumor-associated antigen or an antigen of a pathogen. Preferably, the tumor-associated antigen is selected from the group consisting of CEA, EGFR, HER2, HER3, HER4, VEGFRs, integrin receptor family, fibroblast activation protein, galectin, EpCAM, CEA, CD44, CD44v, CD2, CD5, CD7, CD19, CD20, CD21, CD22, CD24, CD25, CD30, CD33, CD38, CD40, CD52, CD56, CD71, CD72, CD73, CD105, CD117, CD123, c-Met, PDGFR, IGF1-R, HMW-MAA, TAG-72, GD2, GD3, GM2, folate receptor, Le$^y$, MUC-1, MUC-2, PSMA, PSCA and uPAR. In further preferred embodiments the second specificity (B) is directed against molecules of cell membranes, cytokines, chemokines, growth factors, proteins of the complement system, proteins of the coagulation system, fibrinolytic proteins, enzymes which are able to convert the inactive precursor of a drug into an active drug on the target structure, peptide hormones, steroid hormones, the constant part of an immunoglobulin, cytotoxic peptide, and pharmaceuticals. Preferably, the second specificity (B) is directed against molecules on the cell membrane of lymphocytes, macrophages, monocytes or granulocytes, more preferably against molecules on the cell membrane of T-cells. It is particularly preferred that the second specificity (B) is directed against CD3, more preferably against the extracellular region of CD3.

In further embodiments of the present invention the Ig binding moiety and the pharmaceutically active moiety are connected via covalent or non-covalent bond(s). It is particularly preferred that the Ig binding moiety and the pharmaceutically active moiety are connected directly or indirectly via one or more linkers. Preferably, the one or more linkers comprise peptide linkers, more preferably flexible peptide linkers. In preferred embodiments, a peptide linker according to the present invention has a minimum length of at least 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 amino acids, preferably of at least 1, 2, 3, 4, 5, 6, 7, 8, 9, 10, 11, 12, 13, 14, 15 amino acids. Preferably, a peptide linker according to the present invention has a maximum length of at least 100, 95, 90, 85, 80, 75, 70, 65, 60, 55, 50, 45, 40, 35, 34, 33, 32, 31, 30, 29, 28, 27, 26, 25, 24, 23, 22, 21, 20, 19, 18, 17, 16, or 15 amino acids or less. Preferably, the linker has a length of 1-40, preferably of 5-20, more preferably of 18-12, most preferably of 10 amino acids. In preferred embodiments of the present invention, the peptide linker has an increased content of small amino acids, in particular of glycins and/or alanines, and/or hydrophilic amino acids such as serines, threonines, asparagines and glutamines. Preferably, more than 20%, 30%, 40%, 50%, 60% or more of the amino acids of the peptide linker are small and/or hydrophilic amino acids. Preferably the amino acids of the linker are selected from glycines and serines. In further preferred embodiments, the peptide linker of the present invention is non-immunogenic; in particularly preferred embodiments, the peptide linker is non-immunogenic to humans. A peptide linker having the sequence GGSGGGGSGG (SEQ ID NO: 17) is particularly preferred.

In preferred embodiments the Ig binding moiety comprises a streptococcal IgBD, more preferably the C3 IgBD of streptococcal Protein G (SpG-C3), which is connected via a flexible linker to the pharmaceutically active moiety, preferably to an antigen binding molecule selected from the group consisting of an antibody fragment, a Fab fragment, a Fab' fragment, a F(ab')$_2$ fragment, a heavy chain antibody, a single-domain antibody (sdAb), a single-chain variable fragment (scFv), a di-scFv, a bispecific T-cell engager (BITEs), a diabody, a single-chain diabody, a DART molecule, a triple body, an alternative scaffold protein, and a fusion protein thereof.

In particularly preferred embodiments of the first aspect of the present invention, the complex of the present invention comprises an amino acid sequence according to SEQ ID NO: 13, SEQ ID NO: 14 or SEQ ID NO: 15 or variants thereof. Preferably, such variant has a sequence identity of at least 94%, i.e. of at least 94%, at least, 95%, at least 96%, at least 97%, at least 98%, at least 99% sequence identity, to an amino acid sequence according to SEQ ID NO: 13, SEQ ID NO: 14 or SEQ ID NO: 15.

In further embodiments the one or more peptide linkers comprise one or more cleavage sites, preferably one or more endopeptidase cleavage sites. It is preferred that the cleavage site allows for the release of the pharmaceutically active moiety once the intended destination is reached. Preferably, an endopeptidase cleavage site relates to cleavage cite within the amino acid sequence where this sequence is cleaved or is cleavable by an endopeptidase such as but not limited to trypsin, pepsin, elastase, thrombin, collagenase, furin, thermolysin, endopeptidase V8, metalloproteinases and cathepsins.

In a second aspect, the present invention provides a nucleic acid molecule comprising a sequence encoding the complex of the first aspect. Preferably such nucleic acid molecule comprises a DNA and/or RNA molecule.

In a third aspect, the present invention provides a vector comprising the nucleic acid of the second aspect. It is understood that suitable vectors include but are not limited to plasmids, cosmids, phages, viruses and/or artificial chromosomes.

In a fourth aspect, the present invention provides an isolated cell containing the complex of the first aspect and/or the nucleic acid molecule of the second aspect and/or the vector of the third aspect. It is understood that such cell includes but is not limited to prokaryotic (e.g. a bacterial cell) or eukaryotic cells (e.g. a fungal, plant or animal cell).

In a fifth aspect, the present invention provides a composition comprising the complex of the first aspect, the nucleic acid of the second aspect, the vector of the third aspect and/or the cell of the fourth aspect and a pharmaceutical acceptable carrier and/or excipient. Preferably, such composition is a pharmaceutical composition. In preferred embodiments the pharmaceutical composition further comprises a pharmaceutically acceptable carrier and/or excipient and optionally one or more additional active substances.

Preferably, the composition of the fifth aspect contains a therapeutically effective amount of the compound, preferably in purified form, together with a suitable amount of carrier and/or excipient so as to provide the form for proper administration to the patient. The formulation should suit the mode of administration.

The pharmaceutical compositions can take the form of solutions, suspensions, emulsion, tablets, pills, capsules, powders, sustained-release formulations and the like. The pharmaceutical composition can be formulated as a suppository, with traditional binders and carriers such as triglycerides.

For preparing pharmaceutical compositions of the present invention, pharmaceutically acceptable carriers can be either solid or liquid. Solid form compositions include powders, tablets, pills, capsules, lozenges, cachets, suppositories, and dispersible granules. A solid excipient can be one or more substances, which may also act as diluents, flavouring agents, binders, preservatives, tablet disintegrating agents, or an encapsulating material. In powders, the excipient is preferably a finely divided solid, which is in a mixture with the finely divided inhibitor of the present invention. In tablets, the active ingredient is mixed with the carrier having the necessary binding properties in suitable proportions and compacted in the shape and size desired. Suitable excipients are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. For preparing suppositories, a low melting wax, such as a mixture of fatty acid glycerides or cocoa butter, is first melted and the active component is dispersed homogeneously therein, as by stirring. The molten homogeneous mixture is then poured into convenient sized moulds, allowed to cool, and thereby to solidify. Tablets, powders, capsules, pills, cachets, and lozenges can be used as solid dosage forms suitable for oral administration.

Liquid form compositions include solutions, suspensions, and emulsions, for example, water, saline solutions, aqueous dextrose, glycerol solutions or water/propylene glycol solutions. For parenteral injections (e.g. intravenous, intraarterial, intraosseous infusion, intramuscular, subcutaneous, intraperitoneal, intradermal, and intrathecal injections), liquid preparations can be formulated in solution in, e.g. aqueous polyethylene glycol solution. A saline solution is a preferred carrier when the pharmaceutical composition is administered intravenously.

Preferably, the pharmaceutical composition is in unit dosage form. In such form the composition may be subdivided into unit doses containing appropriate quantities of the active component. The unit dosage form can be a packaged composition, the package containing discrete quantities of the composition, such as packaged tablets, capsules, and powders in vials or ampoules. Also, the unit dosage form can be a capsule, an injection vial, a tablet, a cachet, or a lozenge itself, or it can be the appropriate number of any of these in packaged form.

The composition, if desired, can also contain minor amounts of wetting or emulsifying agents, or pH buffering agents.

Furthermore, such pharmaceutical composition may also comprise other pharmacologically active substance such as but not limited to adjuvants and/or additional active ingredients. Adjuvants in the context of the present invention include but are not limited to inorganic adjuvants, organic adjuvants, oil-based adjuvants, cytokines, particulate adjuvants, virosomes, bacterial adjuvants, synthetic adjuvants, or synthetic polynucleotides adjuvants.

In a sixth aspect, the present invention provides the complex of the first aspect of the present invention as described above, for the use in extending the serum half-life and/or the plasma half-life. It is preferred that the complex of the first aspect of the present invention is for the use in extending the initial and/or terminal serum half-life. In preferred embodiments the serum half-life, more preferably the initial and/or terminal serum half-life, of the pharmaceutically active moiety is prolonged. Preferably, the serum half-life, more preferably the initial and/or terminal serum half-life, of the pharmaceutically active moiety is prolonged due to its complexing to an immunoglobulin-binding moiety, preferably to an IgBD, more preferably to the C3-IgBD of streptococcal Protein G.

It is further preferred that the complex of the first aspect of the present invention is for the use in extending the initial and/or terminal plasma half-life. In preferred embodiments the plasma half-life, more preferably the initial and/or terminal plasma half-life, of the pharmaceutically active moiety is prolonged. Preferably, the plasma half-life, more preferably the initial and/or terminal plasma half-life, of the pharmaceutically active moiety is prolonged due to its complexing to an immunoglobulin-binding moiety, preferably to an IgBD, more preferably to the C3-IgBD of streptococcal Protein G.

In a seventh aspect, the present invention provides the complex of the first aspect of the present invention as described in detail above for use as a medicament. In preferred embodiments the complex is for use in medicine, i.e. for use in the prophylaxis, treatment or diagnosis of a disorder or disease such as but not limited to autoimmune diseases, allergic diseases, cancer type diseases, cutaneous conditions, endocrine diseases, eye diseases and disorders, genetic disorders, infectious diseases, intestinal diseases, neurological disorders, and mental illness. Exemplified, autoimmune diseases include but are not limited to Diabetes mellitus type 1, rheumatoid arthritis, psoriasis, Crohns Disease, autoimmune cardiomyopathy, autoimmune hepatitis, Hashimoto's thyroiditis, and Sjogern's syndrome. Exemplified, allergic diseases include but are not limited to allergic rhinitis, asthma, atopic eczema, anaphylaxis, insect venom allergies, drug allergies, and food allergies. Exemplified, cancer type diseases include but are not limited to Basal cell carcinoma, Bladder cancer, Bone cancer, Brain tumor, Breast cancer, Burkitt lymphoma, Cervical cancer, Colon Cancer, Cutaneous T-cell lymphoma, Esophageal cancer, Retinoblastoma, Gastric (Stomach) cancer, Gastrointestinal stromal tumor, Glioma, Hodgkin lymphoma, Kaposi sarcoma, Leukemias, Lymphomas, Melanoma, Oropharyngeal cancer, Ovarian cancer, Pancreatic cancer, Pleuropulmonary blastoma, Prostate cancer, Throat cancer, Thyroid cancer, and Urethral cancer. Exemplified, cutaneous conditions include but are not limited to Acne, Dermatitis, Eczema, conditions of the skin appendages, conditions of the subcutaneous fat, disturbances of pigmentation, epidermal nevi, epidermal neoplasms, epidermal cysts, erythemas, frostbites genodermatoses, mucinoses, neurocutaneous conditions (e.g. Wiskott-Aldrich syndrome), and psoriasis. Exemplified, endocrine diseases include but are not limited to Diabetes mellitus type 1 and type 2, Osteoporosis, and Cushing's disease. Exemplified, genetic disorders include but are not limited to color blindness, cystic fibrosis, Down syndrome, Sickle-cell disease, and Turner syndrome. Exemplified, infectious diseases include but are not limited to infections diseases caused by viruses, bacteria, worms, prions or other pathogens or parasites such as African sleeping sickness, AIDS, HIV infection, Anthrax, Borreliosis, Calicivirus infection (Norovirus and Sapovirus), Chickenpox, *Chlamydia* infection, Cholera, *Clostridium* infection, Colorado tick fever (CTF), common cold, Creutzfeldt-Jakob disease, Dengue fever (DEN-1, DEN-2, DEN-3 and DEN-4), Ebola, Enterovirus infection, infections with Human herpesvirus 6 (HHV-6) and Human herpesvirus 7 (HHV-7), Gonorrhea, Streptoccocal infections (group A and B), Hand, foot and mouth disease (HFMD), *Helicobacter pylori* infection, Hepatitis (A, B, C, and D), Herpes infection, Papillomavirus infection, Parainfluenza virus infection, Influenza, Lassa fever, Marburg fever, Measles, Meningitis, Mumps, Pasteurellosis, *Pediculus* infection, Plague, Pneumococcal infection, Respiratory syncytial virus infection, Rotavirus infection, Rubella virus infection, *Salmonella* food poisoning and infection, SARS, Scabies infections, Schistosomiasis, Smallpox, Staphylococcal food poisoning and infection, Syphilis, Tetanus, *Trichophyton* infection, Tuberculosis, Typhus, Venezuelan equine encephalitis, and Yellow fever. Exemplified, intestinal diseases include but are not limited to Gastroenteritis, Ileus, Ileitis, Colitis, Appendicitis, Coeliac disease, Irritable bowel syndrome, Diverticular disease, Diarrhea, Polyp, and Ulcerative colitis. Exemplified, neurological disorders include but are not limited to Amyotrophic Lateral Sclerosis (ALS), Alzheimer's disease, Brain damage, Creutzfeldt-Jakob disease, Cushing's syndrome, Dyslexia, Encephalitis, Epilepsy, Headache, Huntington's disease, Migraine, Multiple sclerosis, Parkinson's disease, Polio, Rabies, Schizophrenia, and Stroke. Exemplified, mental illness include but are not limited to Acute stress disorder, attention-deficit hyperactivity disorder (ADHD), Autistic disorder, Borderline personality disorder, Bulimia nervosa, Burn Out, Schizophrenia, Depression, Cognitive disorder, Communication disorder, Eating disorder, Kleptomania, Learning disorders, Male erectile disorder, Melancholia, Obsessive-compulsive disorder (OCD), Paranoia Pathological gambling, Posttraumatic stress disorder (PTSD), Psychotic disorder, Hypersomnia, Insomnia, and Tourette's syndrome.

The following examples are merely illustrative of the present invention and should not be construed to limit the scope of the invention as indicated by the appended claims in any way.

EXAMPLES

Example 1: Construction and Production of scDb-IgBD Fusion Proteins

Figure 2:
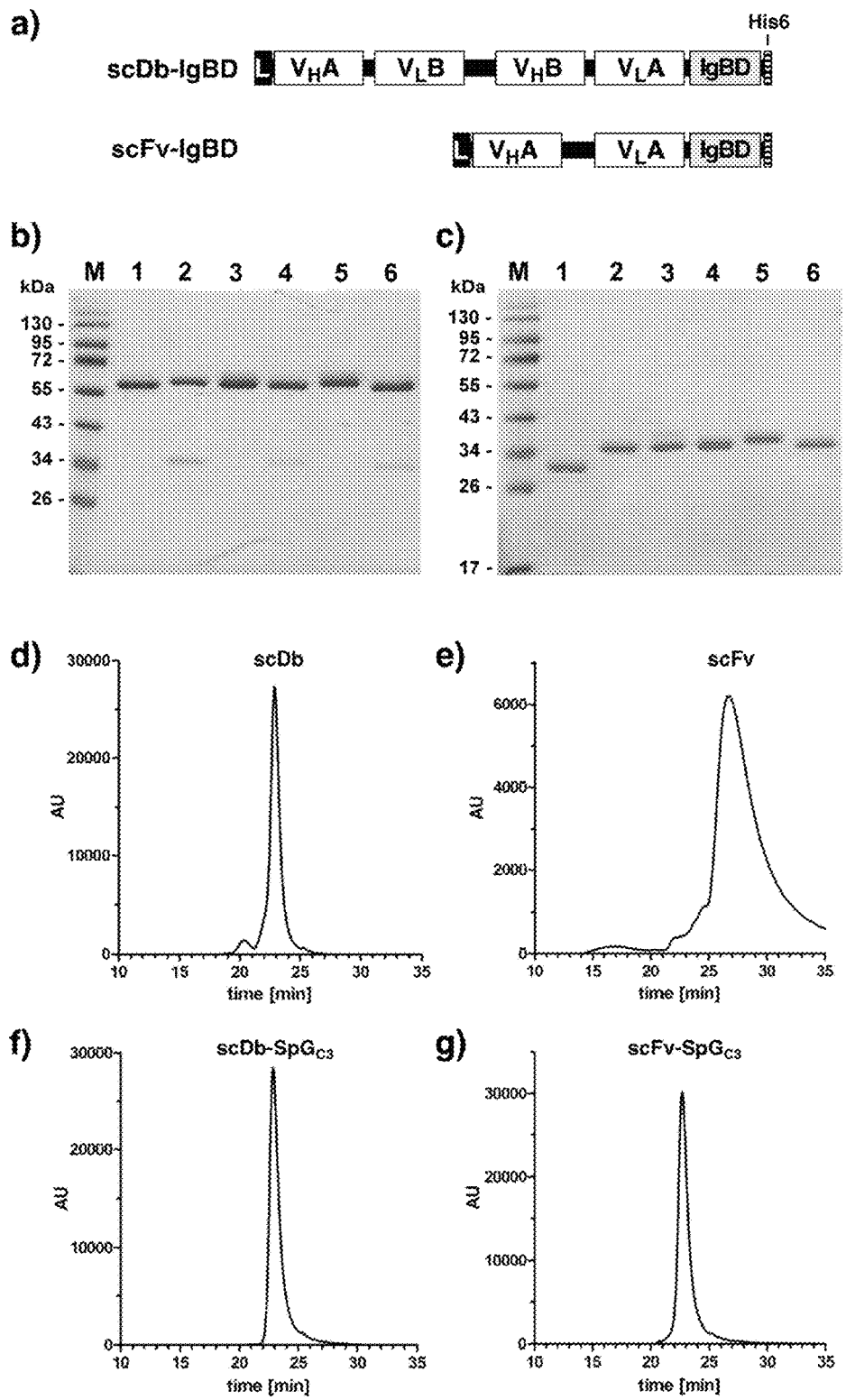
FIG. 2: Construction of scDb-IgBDs and scFv-IgBDs. a) Composition of the scDb-IgBD and scFv-IgBD fusion protein. IgBDs are fused to the C-terminus of a bispecific scDb or a scFv. b) SDS-PAGE analysis of purified scDb-CEACD3 (1), scDb-$SpA_B$ (2), scDb-$SpA_D$ (3), scDb-$SpA_{EZ4}$(4), scDb-$SpG_{C3}$ (5), and scDb-$PpL_{C4}$* (6) under reducing conditions. c) SDS-PAGE analysis of purified anti-CEA scFv (1), scFv-$SpA_B$ (2), scFv-$SpA_D$ (3), scFv-$SpA_{EZ4}$(4), scFv-$SpG_{C3}$ (5), and scFv-$PpL_{C4}$* (6) under reducing conditions. Two micrograms of the proteins were analyzed per lane and the gel was stained with Coomassie brilliant blue G-250 (M, molecular weight standards). d-g) Purified scDb, scFv as well as the scDb-$SpG_{C3}$ and scFv-$SpG_{C3}$ fusion proteins were analyzed by SEC.
Figure 3:
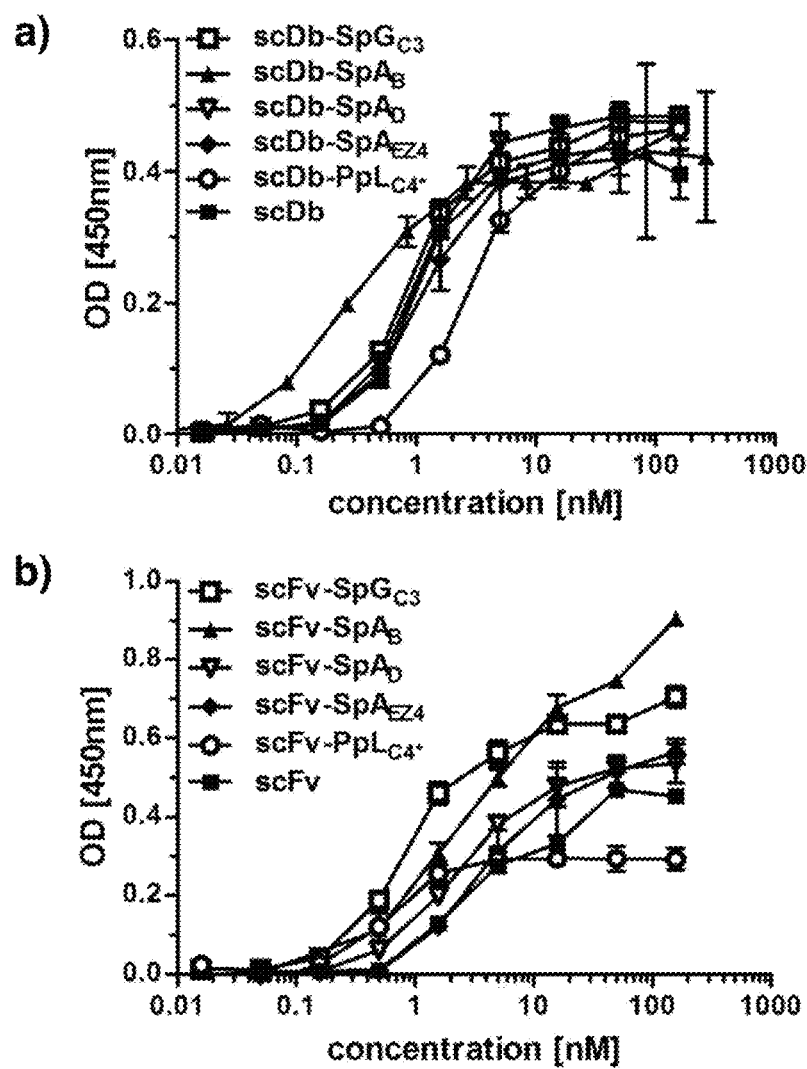
FIG. 3. Binding of scDb-IgBD and scFv-IgBD fusion proteins to CEA in ELISA. Increasing concentrations of the scDb-IgBD (a) or scFv-IgBD (b) fusion proteins were analyzed for binding to immobilized CEA.

DNA encoding the IgBDs (IgBD SpA$_B$, SpA$_D$, SpA$_{EZ4}$, SpG$_{C3}$, and PpL$_{C4}$*) including a hexahistidyl-tag at the C-terminus were synthesized by GeneArt (Regensburg, Germany) adding a NotI at the 5' end and an EcoRI and XbaI site at the 3' end. IgBD SpA$_B$ was cloned into mammalian expression vector pSecTagAHis scDb-CEACD3-ABD-L (Hopp et al. (2010) Protein Eng. Des. Sel. 23:827-834) cut with NotI and XbaI. The IgBD SpA$_D$, SpA$_{EZ4}$, SpG$_{C3}$, and PpL$_{C4}$* were then cloned into scDb-CEACD3-SpA$_B$ as NotI-EcoRI fragments substituting the SpA$_B$ IgBD. Composition of the scDb-IgBD fusion proteins are given in FIG. 2a. HEK293 cells were stably transfected and the fusion proteins scDb-SpA$_B$, scDb-SpA$_D$, scDb-SpA$_{EZ4}$, scDb-SpG$_{C3}$, and scDb-PpLC$_4$* were purified from cell culture supernatant by IMAC essentially as described previously (Müller et al. (2007) J. Biol. Chem. 282:12650-12660). Yields of 2 to 22 mg/L supernatant were obtained. SDS-PAGE of purified fusion proteins was performed. Two micrograms proteins were analyzed per lane and the gel was stained with Coomassie brilliant blue G-250 (M, molecular weight standards). SDS-PAGE analysis revealed a single band under reducing and non-reducing conditions (FIG. 2b). Compared with unmodified scDb, the molecular mass was increased by approximately 5 kDa under reducing conditions.

Example 2: Construction and Production of scFv-IgBD Fusion Proteins

DNA encoding the IgBDs (IgBD $SpA_B$, $SpA_D$, $SpA_{EZ4}$, $SpG_{C3}$, and $PpL_{C4}$*) including a hexahistidyl-tag at the C-terminus were synthesized by GeneArt (Regensburg, Germany) adding a NotI at the 5' end and an EcoRI and XbaI site at the 3' end. The DNA was digested with NotI and EcoRI and cloned into vector pSecTagA-scFvCEA-4-1BBL (Müller et al. (2008) J. Immunol. 31:714-722). Composition of the scFv-IgBD fusion proteins are given in FIG. 2a. HEK293 cells were stably transfected and the fusion proteins scFv-$SpA_B$, scFv-$SpA_D$, scFv-$SpA_{EZ4}$, scFv-$SpG_{C3}$, and scFv-$PpL_{C4}$* were purified from cell culture supernatant by IMAC essentially as described previously (Müller et al., (2007) J. Biol. Chem. 282:12650-12660). SDS-PAGE of purified fusion proteins was performed. Two micrograms proteins were analyzed per lane and the gel was stained with Coomassie brilliant blue G-250 (M, molecular weight standards). SDS-PAGE analysis revealed a single band under reducing and non-reducing conditions (FIG. 2c). Compared with unmodified scFv, the molecular mass was increased by approximately 5 kDa under reducing conditions.

Example 3: Size Exclusion Chromatography (SEC)

Purity and stokes radii of the scDb-IgBD and scFv-IgBD fusions proteins were analyzed by HPLC size exclusion chromatography using a BioSuite 250 (Waters Corporation, Milford, USA) and a flow rate of 0.5 ml/min (FIG. 2d-g). The following standard proteins were used: thyroglobulin, β-amylase, bovine serum albumin, carbonic anhydrase, cytochrome c. All fusion proteins showed a single peak corresponding to monomeric molecules. The measured Stokes radii of the fusion proteins were in the range of 2.3 to 2.7 nm. Interestingly, the Stokes radii of the scFv-IgBD fusion proteins were similar to those of the scDb-IgBD fusion proteins, while the unmodified scFv had a Stokes radius of 1.2 nm (see also FIG. 8).

Example 4: Binding of scDb-IgBD and scFv-IgBD Fusion Proteins to CEA in ELISA

Increasing concentrations of the scDb-IgBD (a) or scFv-IgBD (b) fusion proteins were analyzed for binding to immobilized CEA by ELISA. Carcinoembryonic antigen (CEA) (300 ng/well) was coated overnight at 4° C. and remaining binding sites were blocked with 2% (w/v) dry milk/PBS. Purified recombinant scDb, scFV, as well as scDb-IgBD and scFv-IgBD fusion proteins were titrated in duplicates and incubated for 1 h at RT. Detection was performed with mouse HRP-conjugated anti-His-tag antibody using TMB substrate (0.1 mg/ml TMB, 100 mM sodium acetate buffer pH 6.0, 0.006% $H_2O_2$). The reaction was stopped with 50 µl of 1 M $H_2SO_4$. Absorbance was measured at 450 nm in an ELISA-reader.

Figure 4:
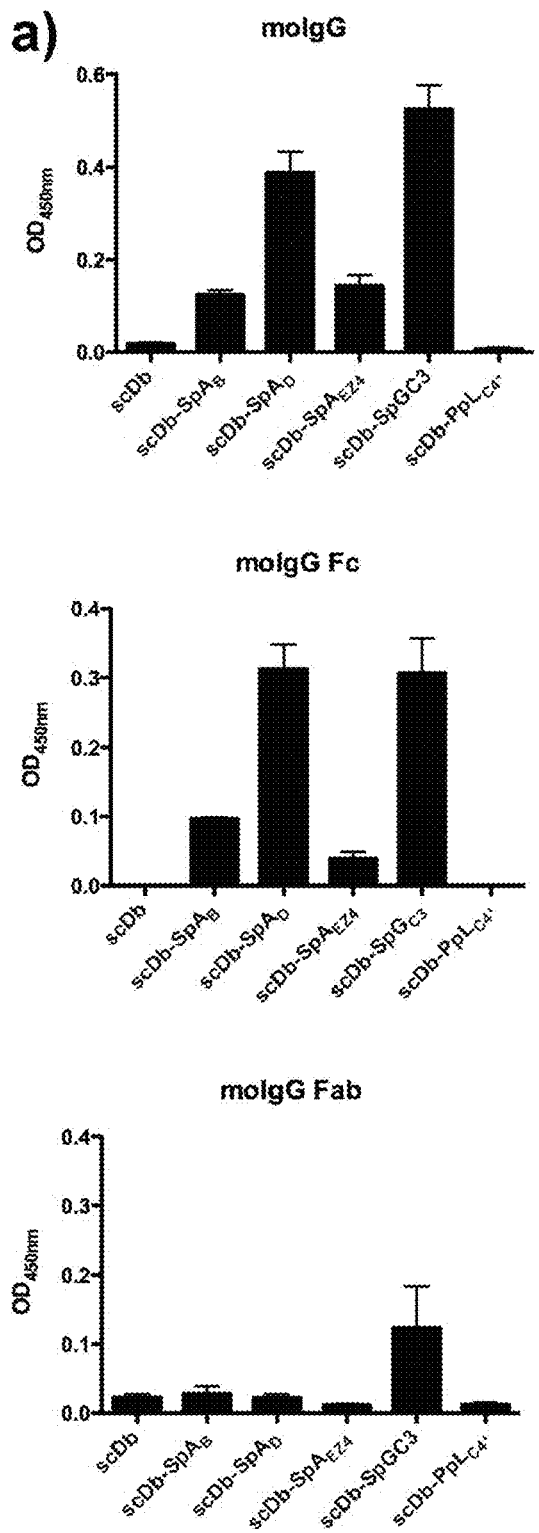
FIG. 4: Binding of scDb-IgBD to IgG, Fab and Fc analyzed by ELISA. scDb, scDb-$SpA_B$, scDb-$SpA_D$, scDb-$SpA_{E4}$, scDb-$SpG_{C3}$, and scDb-$PpL_{C4}$* were analyzed for binding to immobilized mouse (a) and human (b) serum IgG as well as Fab and Fc fragments thereof. Furthermore, human IgM and human IgA were analyzed for binding of these fusion proteins.
Figure 4:
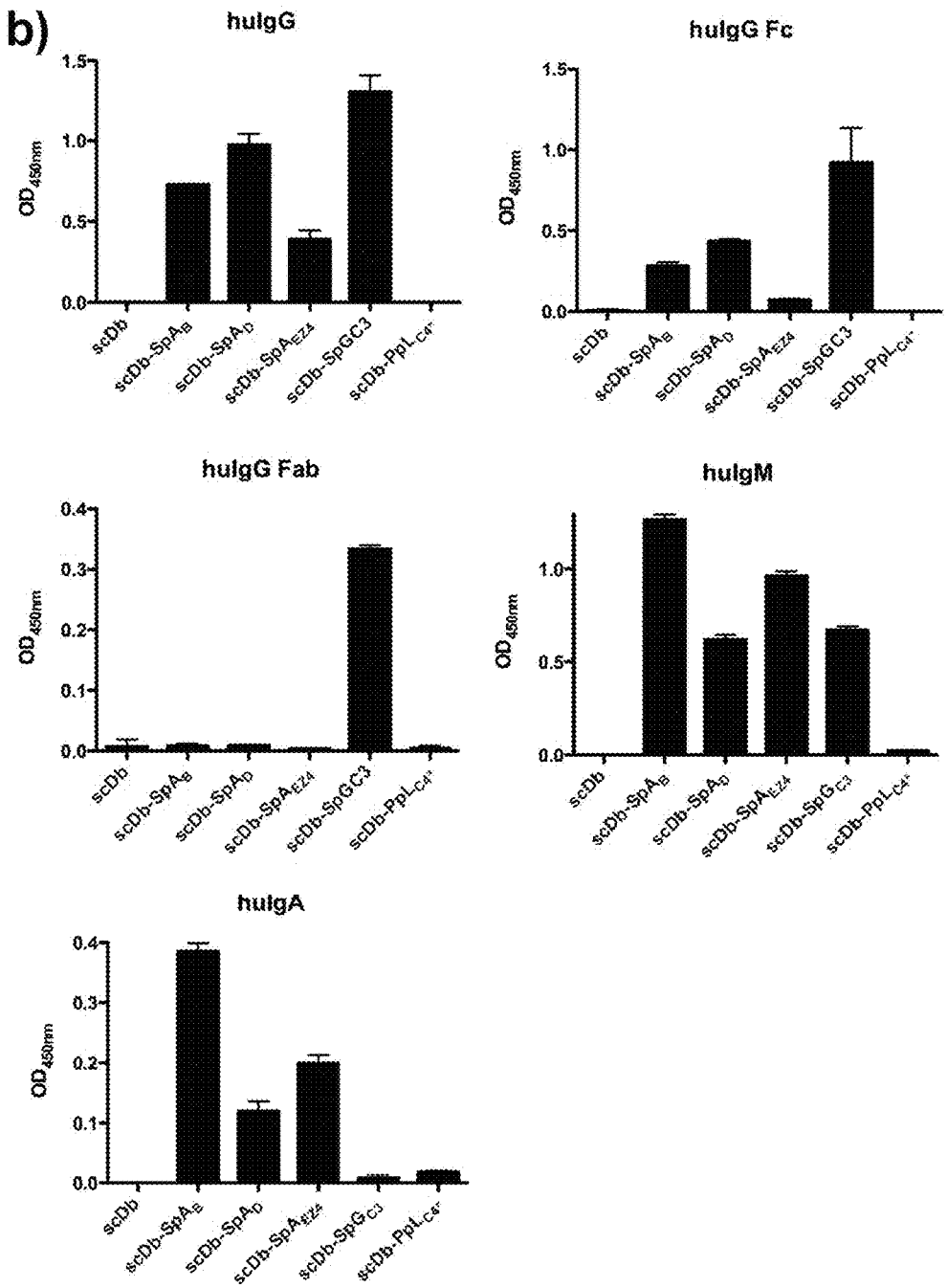

Example 5: Binding of scDb-IgBD Fusion Proteins to Human and Mouse IgG, Human Fab- and Fc-Fragments The fusion proteins scDb-$SpG_{C3}$, scDb-$SpA_B$, scDb-$SpA_D$, scDb-$SpA_{EZ4}$, and scDb-$PpL_{C4}$* were analyzed for binding to immobilized human serum IgG as well as Fab and Fc fragments thereof by ELISA. Human or mouse IgG, human Fab or human Fc fragments (100 ng/well) was coated overnight at 4° C. and remaining binding sites were blocked with 2% (w/v) dry milk/PBS. Purified recombinant antibodies and serum samples were titrated in duplicates and incubated for 1 h at RT. Detection was performed with mouse HRP-conjugated anti-His-tag antibody using TMB substrate (0.1 mg/ml TMB, 100 mM sodium acetate buffer pH 6.0, 0.006% $H_2O_2$). The reaction was stopped with 50 µl of 1 M $H_2SO_4$. Absorbance was measured at 450 nm in an ELISA-reader. Strongest binding to human serum IgG (huIgG), as well as human Ig Fc (huIgFc) was observed for scDb-$SpG_{C3}$ (FIG. 4b). Also, scDb-$SpA_B$, scDb-$SpA_D$, scDb-$SpA_{EZ4}$ were able to bind to huIgG and huIgFc, however their binding was weaker than the binding of scDb-$SpG_{C3}$. Hardly any binding could be observed for scDb-$PpL_{C4}$*. Binding to huIgFab could be observed for scDb-$SpG_{C3}$, whilst all other fusion protein showed hardly any binding to huIgFab. The fusion proteins scDb-$SpG_{C3}$, scDb-$SpA_B$, scDb-$SpA_D$, and scDb-$SpA_{EZ4}$ were also able to bind to huIgM (FIG. 4b) with scDb-$SpA_B$ exhibiting the strongest binding (FIG. 4b). In addition, the fusion proteins scDb-$SpA_B$, scDb-$SpA_D$, and scDb-$SpA_{EZ4}$ also showed binding to huIgA.

Binding of all fusion proteins (except scDb-$PpL_{C4}$*) was also seen with mouse serum IgG (moIgG) as well as mouse Ig Fc (moIgFc), although binding was generally weaker than that seen for the human IgGs (FIG. 4a). Binding to and mouse Ig Fab (moIgFab) fragments was only observed for scDb-$SpG_{C3}$.

Example 6: Affinity Measurements

Figure 5:
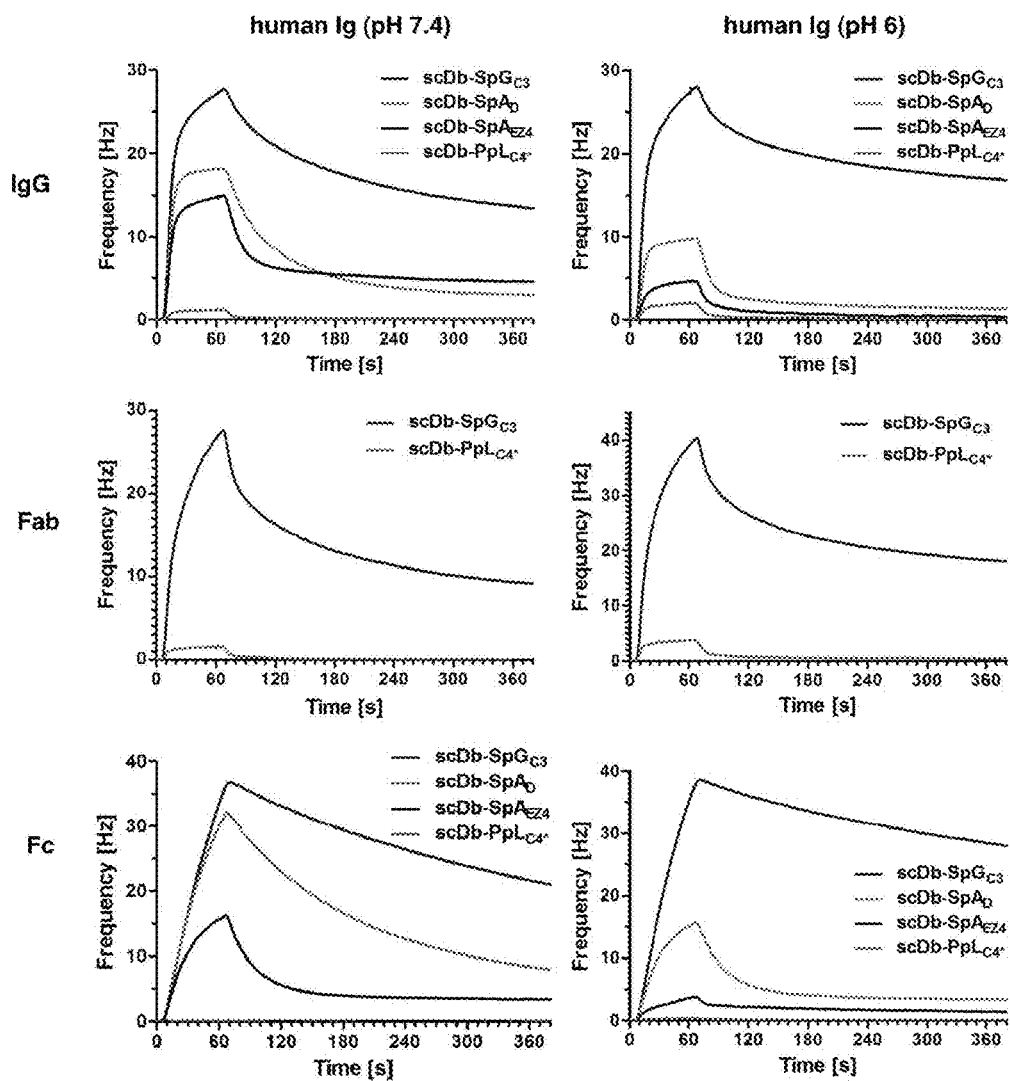
FIG. 5. Binding of scDb-IgBD to IgG, Fab and Fc analyzed by quartz crystal microbalance measurements. Human and mouse IgG as well as Fab and Fc fragments thereof were immobilized on a QCM chip and binding of the scDb-IgBD fusion proteins was determined at 1.5 µM (Fab fragments), 500 nM (IgGs), 40 nM (human IgG) or x nM (IgG-Fc fragments), and 1.28 nM (mouse IgG-Fc fragments).
Figure 6:
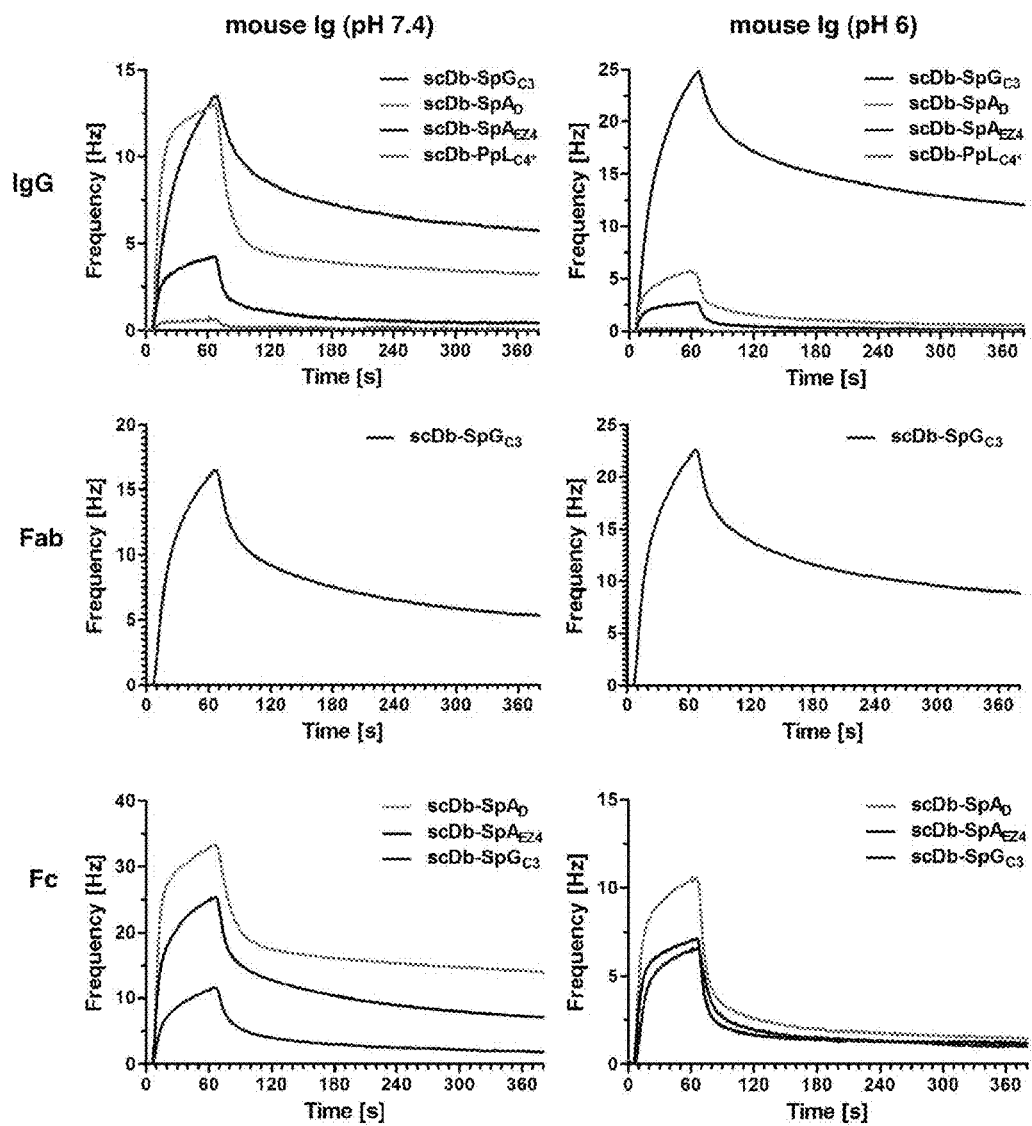
FIG. 6: Affinities. Affinities of the scDb-IgBD fusion proteins for human and mouse IgG and Fab and Fc fragments thereof determined at neutral pH (7.4) and acidic pH (6.0) by quartz crystal microbalance measurements using an Attana A100 and sensorchips with chemically conjugated immunoglobulins.

Affinities of scDb-IgBD fusion proteins for human and mouse serum IgG well as Fab and Fc fragments at neutral or acidic pH were determined by quartz crystal microbalance measurements (Attana A-100 C-Fast system). IgGs as well as Fab and Fc fragments were chemically immobilized on an LNB (low nonspecific binding) carboxyl sensor chip according to the manufacturer's protocol at a density resulting in a signal increase of 65-95 Hz. Binding experiments were performed in PBST (0.1% Tween 20) pH 7.4 or pH 6.0 with at a flow rate of 25 µl/min. The chip was regenerated with 25 µl 10 mM glycine-HCl pH 3.0. Before each measurement, a baseline was measured which was subtracted from the binding curve. Data were collected by Attester 3.0 (Version 3.1.1.8, Attana, Stockholm, Sweden) and analyzed by Attache Office Evaluation Software (Version 3.3.4, Attana, Stockholm, Sweden), using a mass transport model for curve fitting (see Fig. the active compound 5, FIG. 5). Strong binding in the low nanomolar range to human and mouse IgG as well as IgG-Fc was observed for the different SpA-IgBD and the $SpG_{C3}$ fusion proteins. Binding to human and mouse Fab fragments was only observed for scDb-$SpG_{C3}$. The binding of the scDb-SpA-IgBD fusion protein was found to be is pH-dependent and was strongly reduced at pH 6. For example, lowering the pH from 7.4 to 6.0 resulted in an approximately 45-fold reduced affinity of scDb-$SpA_B$ for human serum IgG and a 43-fold reduced affinity for mouse serum IgG. A pH-dependent binding may have a direct influence on FcRn-mediated recycling, which requires that the SpA fusion protein stays bound to IgG-FcRn complexes in the acidic environment of the early endosome (pH ~6.3 to 6.8) and tubular recycling endosomes (pH ~6.5). In contrast, similar or even an increased binding affinity of scDb-SpG$_{C3}$ to human IgFc, human IgFab, mouse IgG and mouse IgFab were observed by lowering the pH value from 7.4 to 6 (FIG. 5).

Example 7: Pharmacokinetics

Figure 7:
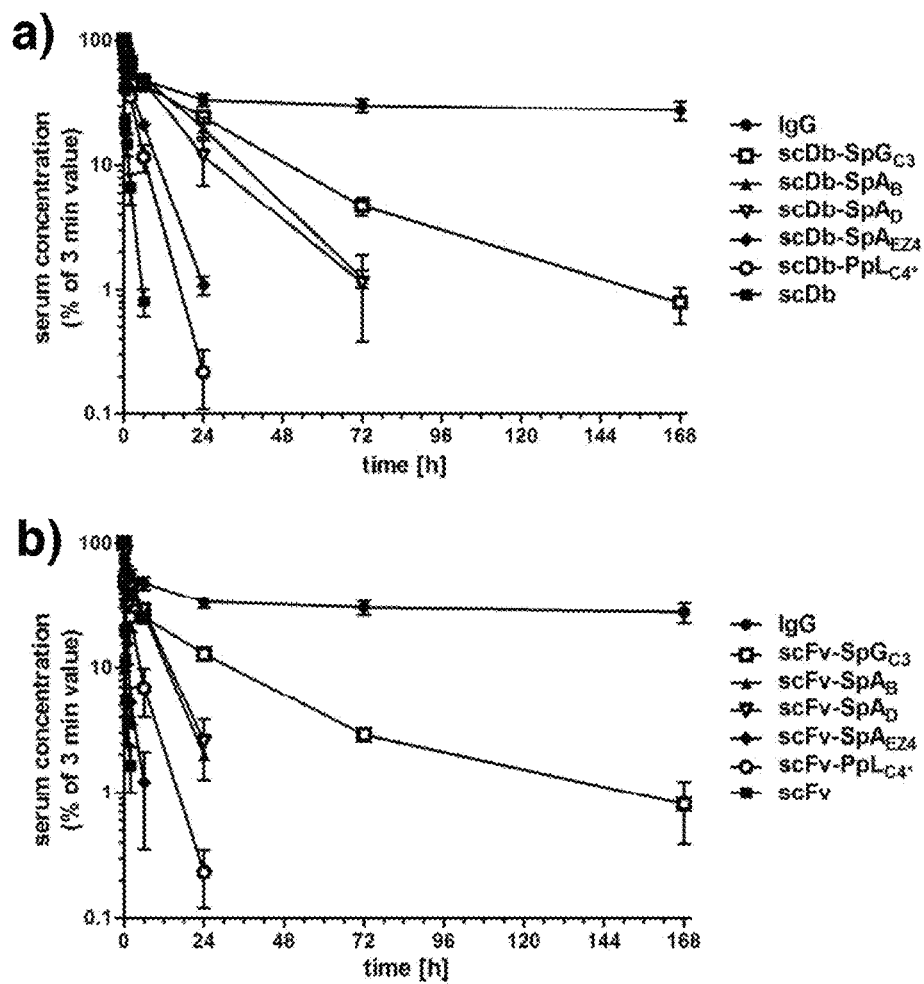
FIG. 7. Plasma half-life of scDb-IgBD and scFv-IgBD fusion proteins in comparison to unmodified proteins (scDb, scFv) and IgG. ScDb-IgBD (a) and scFv-IgBD (b) fusion proteins were i.v. injected into CD1 mice (25 g/animal) and serum concentrations of the antibody molecules were determined at different time points by ELISA. Data were normalized considering maximal concentration at the first time point (3 min).

CD1 mice were purchased from Elevage Janvier (Le Genest St. Isle, France). Animal care and all experiments performed were in accordance with federal guidelines and have been approved by university and state authorities. CD1 mice (8-16 weeks, weight between 30-40 g) received an i.v. injection of 25 g a scDb-IGBD or a scFv-IGBD fusion protein in a total volume of 150 µl. In time intervals of 3 min, 30 min, 1 h, 2 h, 6 h, 1 day, and 3 days blood samples (50 µl) were taken from the tail and incubated on ice. Clotted blood was centrifuged at 13,000 g for 10 min, 4° C. and serum samples stored at −20° C. The active compound Serum concentrations of CEA-binding recombinant antibodies were determined by ELISA. Carcinoembryonic antigen (CEA) (300 ng/well) or IgG (500 ng/well) was coated overnight at 4° C. and remaining binding sites were blocked with 2% (w/v) dry milk/PBS. Purified recombinant antibodies and serum samples were titrated in duplicates and incubated for 1 h at RT. For determination of pH dependence of binding, all incubation and washing steps were performed with PBS adjusted to the indicated pH. Detection was performed with mouse HRP-conjugated anti-His-tag antibody using TMB substrate (0.1 mg/ml TMB, 100 mM sodium acetate buffer pH 6.0, 0.006% $H_2O_2$). The reaction was stopped with 50 µl of 1 M $H_2SO_4$. Absorbance was measured at 450 nm in an ELISA-reader. For comparison, the first value (3 min) was set to 100%. Half-life of scDb-IgBD and scFv-IgBD fusion proteins was analyzed after a single i.v. injection into CD1 mice. The initial plasma half-live ($t_{1/2}\alpha$), the terminal plasma half-life ($t_{1/2}\beta$) and the bioavailability (AUC) were calculated for scDb-IgBD and scFv-IgBD fusion proteins using Excel (FIG. 8). For statistics, Student's t-test was applied. The bioavailability of all fusion proteins was increased in comparison to the non-fused scDb or scFv, respectively. The highest increase in the bioavailability was obtained by scDb-SpG$_{C3}$ and scFv-SpG$_{C3}$ in comparison to the non-fused scDb or scFv, respectively, with scDb-SpG$_{C3}$ exhibiting a 36-fold increase and scFv-SpG$_{C3}$ exhibiting a 65-fold increase in their bioavailability (FIG. 8). Compared to scDb exhibiting a terminal half-life of 1.3 h, the scDb-IgBD fusion proteins showed a strongly prolonged circulation in the blood (FIG. 7a). A terminal half-life of 23.3 h was determined for scDb-SpG$_{C3}$ compared to terminal half-lives of 2.4 h for scDb-PpL$_{C4}$*, 4.2 h for scDb-SpA$_{EZ4}$, 9 h for scDb-SpA$_D$, and 11.8 h for scDb-SpA$_B$ (FIG. 8). Also, scFv-IgBD fusion proteins showed a strongly prolonged circulation in the blood (FIG. 7b). A terminal half-life of 20.8 h was determined for scFv-SpG$_{C3}$ compared to terminal half-lives of 1 to 5 h for scDb-SpA$_B$, scDb-SpA$_D$, scDb-SpA$_{EZ4}$, and scDb-Pp the active compound L$_{C4}$*.

Example 8: IL-2 Release Assay

Figure 9:
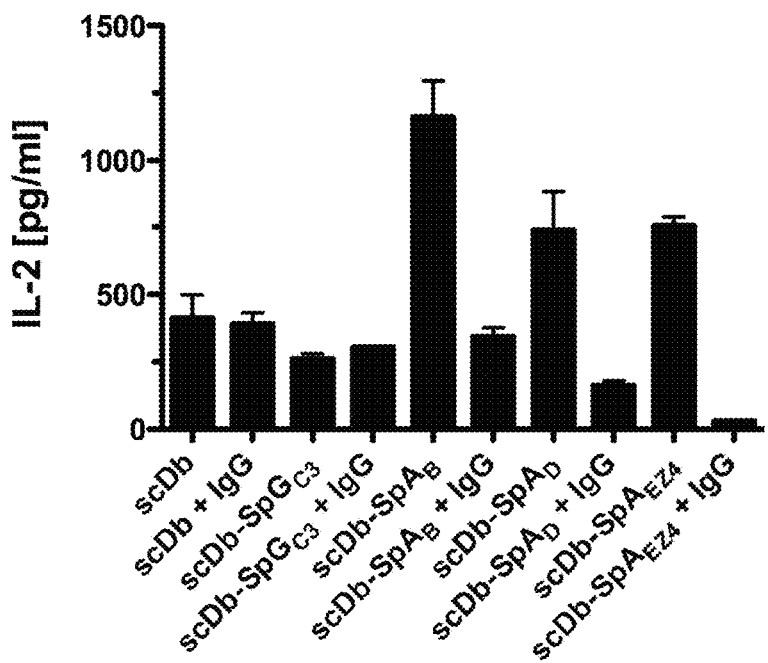
FIG. 9. Immunostimulatory activity of scDb-IgBD fusion proteins. The bispecific anti-CEA×anti-CD3 scDb-IgBD fusion proteins were analyzed in vitro for triggering of IL-2 release from human PBMCs in a target cell-dependent manner in the absence or presence of human IgG (100 µg/ml). CEA-positive target cells (LS1S74T) were grown in microtiter plates and subsequently PBMCs and fusion proteins were added and incubated for 24 h. Subsequently, IL-2 released from activated T cells was determined by ELISA. Unmodified scDb was included as control.

The scDb-fusion proteins were analyzed in vitro for their ability to induce IL-2 release (FIG. 9). Peripheral blood mononuclear cells (PBMC) from healthy donors were isolated from buffy coat as described before (Müller et al. (2007) J. Biol. Chem. 282:12650-12660). 1×10⁵ LS 174T cells/100 l/well were seeded in 96-well plates. The next day supernatant was removed and 150 µl of recombinant antibody added. After 1 h preincubation at 37° C., 2×10⁵ PBMC/50 µl/well were added. PBMCs had been thawed the day before and seeded on a culture dish. Only cells that remained in suspension were used for the assay. After addition of PBMCs, the 96-well plate was incubated for 24 h at 37° C., 5% $CO_2$. Plates were centrifuged and cell-free supernatant collected. Concentration of human IL-2 in the supernatant was determined using the DuoSet IL-2 ELISA kit (R&D Systems) following the manufacturer's protocol. Compared with the unmodified scDb, the scDb-SpA$_B$, scDb-SpA$_D$ and scDb-SpA$_{EZ4}$ fusion proteins showed a strongly increased IL-2 release in the absence of human IgG which indicates that the SpA$_B$ domain induces activation of PBMCs (FIG. 9). In contrast, scDb-SpG$_{C3}$ did not induce an IL-2 release exceeding the IL-2 release induced by scDb.

Example 9: SpG$_{C3}$ Mutants

Figure 10:
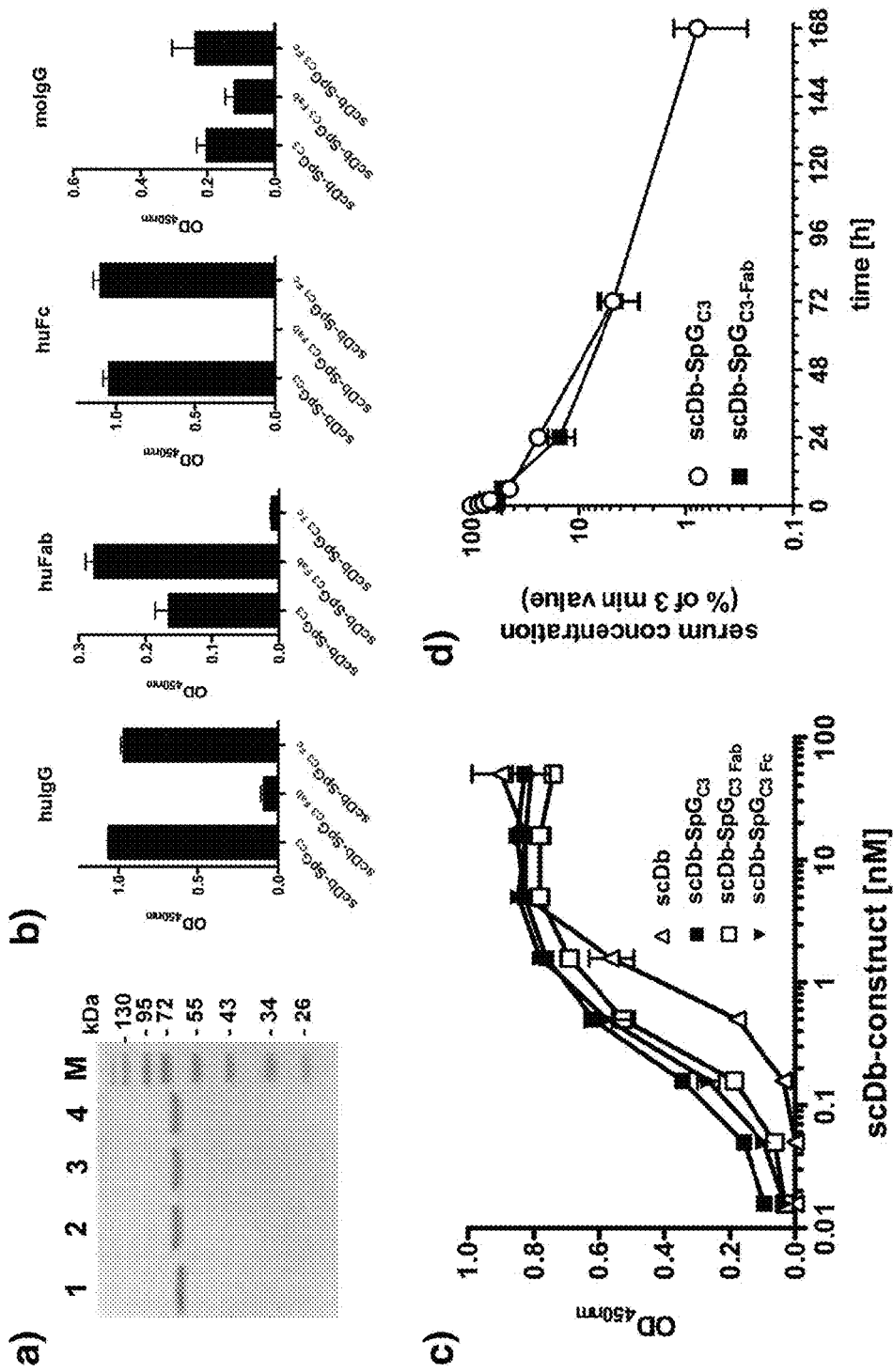
FIG. 10: $SpG_{C3}$ Mutants. a) SDS-PAGE analysis of scDb (1), scDb-$SpG_{C3}$ (2), scDb-$SpG_{C3-Fab}$ (3), scDb-$SpG_{C3}$-Fe (4). Gel was stained with Coomassie brilliant blue G-250. b) Binding of scDb-$SpG_{C3}$, scDb-$SpG_{C3-Fab}$, scDb-$SpG_{C3}$-Fe to human IgG, Fab and Fc analyzed by ELISA. scDb-$SpG_{C3}$, scDb-$SpG_{C3-Fab}$, scDb-$SpG_{C3-Fc}$, were analyzed for binding to immobilized human serum IgG as well as Fab and Fc fragments thereof. c) Binding of scDb, scDb-SpG$_{C3}$, scDb-SpG$_{C3-Fab}$, scDb-SpG$_{C3}$-Fc to CEA analyzed by ELISA. d) Plasma half-life of scDb-SpG$_{C3-Fab}$: scDb-SpG$_{C3-Fab}$ was i.v. injected into CD1 mice (25 μg/animal) and serum concentrations of the antibody molecules were determined at different time points by ELISA. Data were normalized considering maximal concentration at the first time point (3 min).

Variants of scDb-SpG$_{C3}$ lacking the binding site to the Ig Fc fragment (scDb-SpG$_{C3-Fab}$) or the Ig Fab fragment (scDb-SpG$_{C3-Fc}$) were produced in stably transfected HEK293 cells, purified by IMAC and analyzed for binding to human IgG, IgG-Fab fragments and IgG-Fc fragments (FIG. 10a). Binding to the human Fc-fragment could be observed for scDb-SpG$_{C3}$ and scDb-SpG$_{C3-Fc}$ whilst scDb-SpG$_{C3-Fab}$ was not able to bind to huIgFc. In contrast, binding to the human Fab-fragment could be observed for scDb-SpG$_{C3}$ and scDb-SpG$_{C3-Fab}$ whilst scDb-SpG$_{C3}$-Fc was not able to bind to huIgFab (FIG. 10b). scDb-SpG$_{C3-Fab}$ was further analyzed for plasma half-life in CD1 mice as described in Example 7. A terminal half-life of 21.2±5.6 h (n=3) was determined for scDb-SpG$_{C3-Fab}$ (FIGS. 10 c and d), demonstrating that binding to the Fab fragment of immunoglobulins is sufficient to retain the long half-life of the wild-type fusion protein (terminal half-life 23.3±5.9 h (n=6)).

Example 10: A SpG$_{C3}$-Diabody-scTRAIL Fusion Protein

Figure 11:
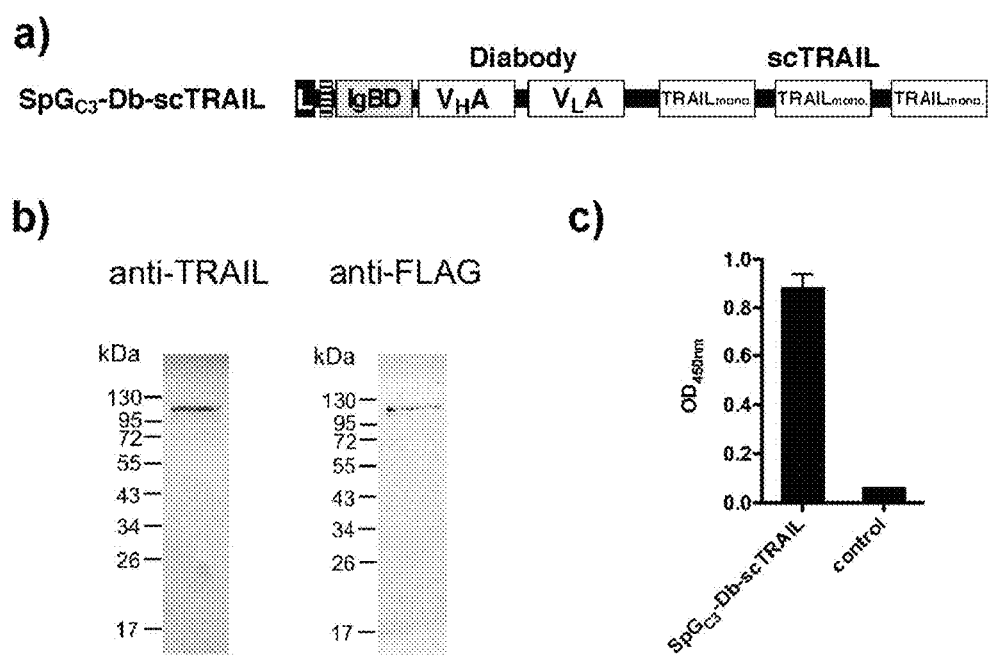
FIG. 11: Production and IgG-binding of an SpG-C3-Diabody-scTRAIL fusion protein. a) Composition of the fusion protein composed of an N-terminal SpG$_{C3}$ domain, an anti-EGFR diabody and a single-chain derivative of TRAIL (scTRAIL). b) Detection of purified fusion protein by Westernblot with anti-TRAIL or anti-FLAG-tag antibodies. A band corresponding to the expected size of approximately 100 kDa is detected. c) Binding of the fusion protein (10 μg/ml) to immobilized human serum IgG in ELISA. Bound fusion protein was detected with an anti-FLAG-tag antibody and an HRP-conjugated anti-mouse antibody. The fusion protein was omitted in the control.

A SpG$_{C3}$-diabody-scTRAIL fusion protein was generated by fusing the SpG$_{C3}$ to an anti-EGFR diabody (VH-VL domains of a humanized anti-EGFR antibody huC225 connected by a 5 residue GGGGS linker) fused by an additional linker to a single-chain derivative of human TRAIL (FIGS. 11 and 13). For purification and detection, the protein contains a FLAG-tag at the N-terminus. The fusion protein was produced by stably transfected HEK293 cells and purified by anti-FLAG affinity chromatography from cell culture supernatant. Westernblot with an anti-TRAIL antibody or an anti-FLAG antibody showed a single band of approximately 100 kDa, corresponding to the expected molecular mass. The purified fusion protein showed strong binding to human IgG in ELISA demonstrating that the SpG$_{C3}$ domain is also functional when fused to the N-terminus of a protein.

Example 11: Comparison of the Pharmacokinetic Properties of scDb-SpG$_{C3}$ and scDb-ABD$_H$ Similar to IgBDs, an albumin-binding domain (ABD) derived from *Streptococcus* protein G has been shown to strongly improve the half-life of small recombinant proteins by recycling via the FcRn when bound to albumin (Stork et al., 2007, Protein Eng. Des. Sel., 20, 569-576; Andersen et al., 2010, J. Biol. Chem. 286, 5234-5241). Several mutants of the ABD with altered affinity for mouse and human albumin have been described and tested for their half-life extension properties (Jonsson et al., 2008, Protein Eng. Des. Sel. 21, 515-527; Hopp et al., 2010, Protein Eng. Des. Sel. 23, 827-834). Amongst them, $ABD_H$ (albumin-binding domain with high affinity) has proven to show the best pharmacokinetic properties and seems therefore a suitable fusion protein for comparison. Furthermore, the affinity of the $ABD_H$ towards albumin is similar to the affinity of $SpG_{C3}$ towards IgG (Hopp et al., 2010, Protein Eng. Des. Sel. 23, 827-834). Therefore, we compared the plasma half-lives of scDb-$ABD_H$ and scDb-$SpG_{C3}$ after a single dose i.v. injection (25 µg/animal) into CD1 mice (FIGS. 16a and *b*), as described above in Example 7. Over the first 24 hours, scDb-$SpG_{C3}$ showed a significantly (p<0.01) increased plasma concentration, displayed by an AUC of 997±79% h compared to 836±81% h for the scDb-$ABD_H$ and 56±15% h for unmodified scDb (FIG. 16c). Additionally, initial plasma half-life was calculated (using the first 3 values) and revealed a 1.6-fold increase in $t_{1/2}\alpha$ for scDb-$SpG_{C3}$ (2.4±0.7 h) compared to scDb-$ABD_H$ (1.5±0.5 h), which was significantly different (p<0.05) (FIG. 16d). Further investigating the biphasic profile of the fusion protein pharmacokinetics resulted in a very similar terminal plasma half-life of 20.6±11.5 h for scDb-$ABD_H$ and 21.0±4.8 h for scDb-$SpG_{C3}$, calculated from 6 h to 24 h. This finding indicates that $SpG_{C3}$ fusion proteins compared to $ABD_H$ fusion proteins, have an improved initial distribution phase resulting in an increased bioavailability as measured by the AUC.

Figure 17:
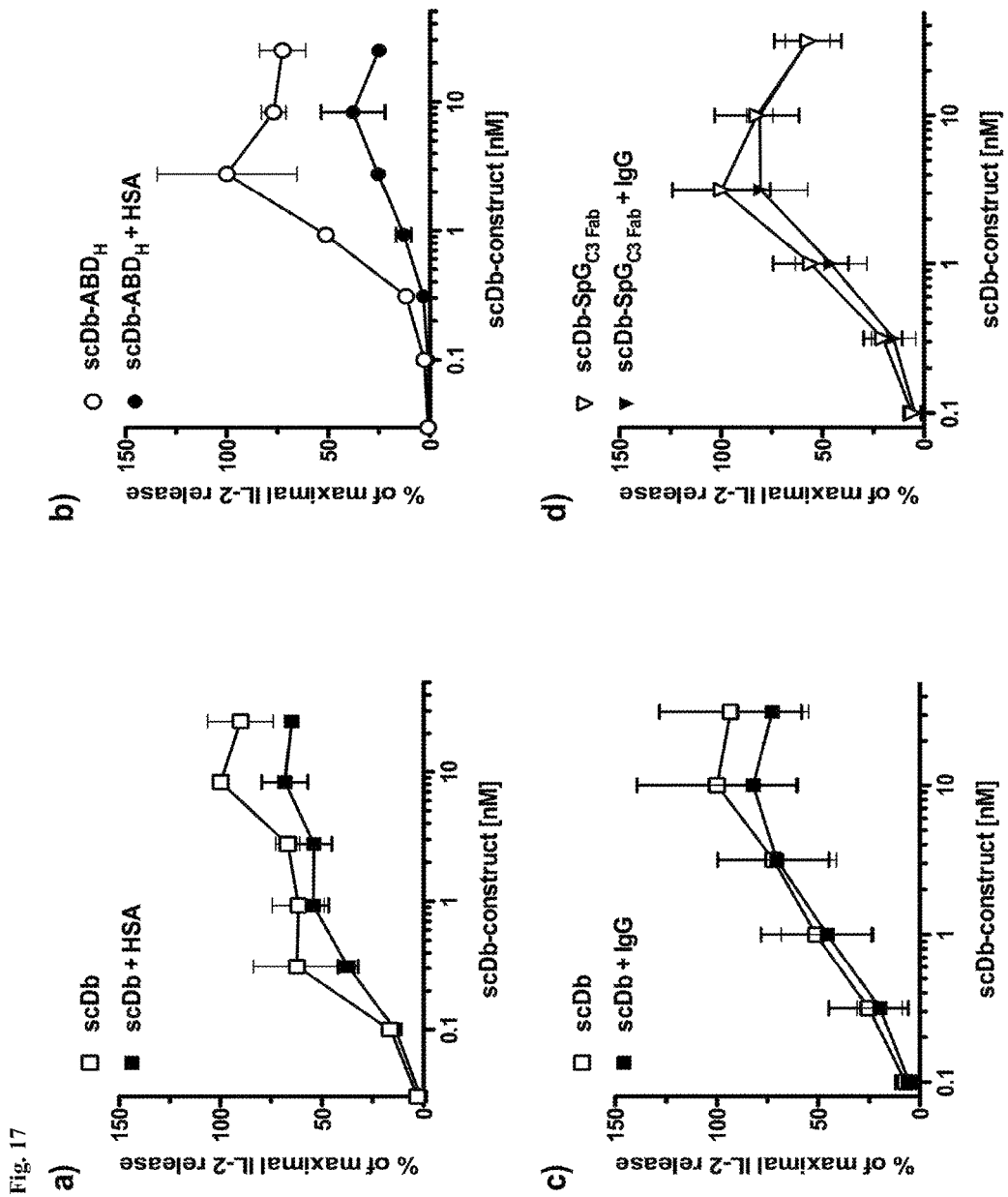
FIG. 17: Comparison of IL-2 release using scDb-SpG$_{C3-Fab}$ and scDb-ABD$_H$ fusion proteins. LS174T cells were incubated with varying concentrations of scDb (a and c), scDb-ABD$_H$ (b) or scDb-SpG$_{C3-Fab}$ (d) before adding human PBMCs. The scDb fusion proteins were either pre-incubated without (white symbols) or with 1 mg/ml HSA (a, b) or 100 μg/ml human IgG (c, d) corresponding approximately to 1/50 of the normal plasma concentrations (black symbols). After 24 h, IL-2 release into the supernatant was determined by ELISA.

Example 12: Comparison of IL-2 Release by scDb-$SpG_{C3\text{-}Fab}$ and scDb-$ABD_H$ in the Absence or Presence of Albumin or IgG The potential of the bispecific anti-CEA×anti-CD3 scDb fusion proteins to stimulate T cells was analyzed using an IL-2 release assay. Following the protocol described above in Example 8, scDb-$SpG_{C3\text{-}Fab}$ and scDb-$ABD_H$ were used in different protein concentrations ranging from 0.1 nM to 31.6 nM (FIG. 17). While the unmodified scDb as reference molecule showed no or only a marginal reduction in IL-2 release in the presence of IgG or human serum albumin (using 1/50 of the physiological concentrations), scDb-$ABD_H$ showed a strong reduction in signal when preincubated with HSA. In contrast, the $SpG_{C3}$ variant $SpG_{C3\text{-}Fab}$, lacking the binding site for the Ig Fc fragment, showed strong activation even in the presence of IgG similar to the unmodified scDb, demonstrating that $SpG_{C3\text{-}Fab}$ is especially suitable for half-life extension of bispecific molecules retargeting effector T cells and that this domain is superior over the established ABD domain.

```
                  Sequence Listing-Free Text Information

SEQ ID NO: 1    Amino acid sequence of the C3 domain of SpG:
                TTYKLVINGKTLKGETTTKAVDAETAEKAFKQYANDNGVDGVW
                TYDDATKTFTVTE SEQ ID NO: 2    Amino acid sequence of C3-Fc:
                TTYKLVINGKALAGATTTKAVDAETAEKAFKQYANDNGVDGVW
                TYDDATKTFTVTE SEQ ID NO: 3    Amino acid sequence of C3-Fab:
                TTYKLVINGKTLKGETTTKAVDAETAAAAFAQYANDNGVDGVW
                TYDDATKTFTVTE SEQ ID NO: 4    Amino acid positions 122-127 and 207-214 of a human Ig γ1 molecule
                according to EU index as in Kabat:
                Gly Pro Ser Val Phe Pro ... Ser Asn Thr Lys Val Asp Lys Lys SEQ ID NO: 5    Amino acid positions 122-127 and 207-214 of a human Ig γ2 molecule
                according to EU index as in Kabat:
                Gly Pro Ser Val Phe Pro ... Ser Asn Thr Lys Val Asp Lys Thr SEQ ID NO: 6    Amino acid positions 122-127 and 207-214 of a human Ig γ3 molecule
                according to EU index as in Kabat:
                Gly Pro Ser Val Phe Pro ... Ser Asn Thr Lys Val Asp Lys Arg SEQ ID NO: 7    Amino acid positions 122-127 and 207-214 of a human Ig γ4 molecule
                according to EU index as in Kabat:
                Gly Pro Ser Val Phe Pro ... Ser Asn Thr Lys Val Asp Lys Arg SEQ ID NO: 8    Amino acid positions 122-127 and 207-214 of a mouse Ig γ1 molecule
                according to EU index as in Kabat:
                Pro Pro Ser Val Tyr Pro ... Ser Ser Thr Lys Val Asp Lys Lys SEQ ID NO: 9    Amino acid positions 122-127 and 207-214 of a mouse Ig γ2a molecule
                according to EU index as in Kabat:
                Ala Pro Ser Val Tyr Pro ... Ser Ser Thr Lys Val Asp Lys Lys SEQ ID NO: 10   Amino acid positions 122-127 and 207-214 of a mouse Ig γ2b molecule
                according to EU index as in Kabat:
                Ala Pro Ser Val Tyr Pro ... Ser Ser Thr Thr Val Asp Lys Lys SEQ ID NO: 11   Amino acid positions 122-127 and 207-214 of a mouse Ig γ3 molecule
                according to EU index as in Kabat:
                Ala Pro Ser Val Tyr Pro ... Ser Lys Thr Glu Leu Ile Lys Arg SEQ ID NO: 12   Amino acid positions 122-127 and 207-214 of a rat Ig g1 molecule
                according to EU index as in Kabat:
                Ala Pro Ser Val Tyr Pro ... Ser Ser Thr Lys Val Asp Lys Lys
```

| Sequence Listing-Free Text Information |
| --- |
| SEQ ID NO: 13   Amino acid sequence of scFv-SpG-C3 (anti-CEA) |
| SEQ ID NO: 14   Amino acid sequence of scDb-SpG-C3 (anti-CEA x anti-CD3) |
| SEQ ID NO: 15   Amino acid sequence of SpG-C3-Db-scTRAIL (anti-human EGFR) |
| SEQ ID NO: 16   Amino acid sequence of the C1 domain of SpG: |
| SEQ ID NO: 17   Amino acid sequence of the C2 domain of SpG: |

The invention claimed is:

1. An immunoglobulin (Ig) binding moiety comprising a $C_H1$ binding-immunoglobulin binding domain (IgBD) of a streptococcal protein G, which is a variant of SEQ ID NO: 1, wherein the three amino acids Glu26, Lys27, and Lys30 of SEQ ID NO: 1 are substituted with Ala and which may have up to 3 further amino acid substitutions, wherein the Ig binding moiety specifically binds to the constant domain 1 of the heavy chain ($C_H1$) of an Ig molecule wherein the variant has the amino acid sequence TTYKLVINGKTLK-GETTTKAVDAETAAAAFAQYANDNGVDGVWTYDD-ATKTFTVTE (SEQ ID NO: 3).

2. An immunoglobulin (Ig) binding moiety comprising a $C_H1$ binding-immunoglobulin binding domain (IgBD) of a streptococcal protein G, which is a variant of SEQ ID NO: 1, wherein the three amino acids Glu26, Lys27, and Lys30 of SEQ ID NO: 1 are substituted with Ala and which may have up to 3 further amino acid substitutions, wherein the Ig binding moiety specifically binds to the constant domain 1 of the heavy chain $C_H1$ of an Ig molecule wherein the variant consists of the amino acid sequence TTYKLVING-KTLKGETTTKAVDAETAAAAFAQYANDNGVDGVW-TYDDATKTFTVTE (SEQ ID NO: 3).

3. A nucleic acid molecule comprising a sequence encoding the Ig binding moiety of claim 1 or 2.

4. A vector comprising the nucleic acid of claim 3.

5. A cell comprising the Ig binding moiety of claim 1 or 2, the nucleic acid of claim 3 and/or the vector of claim 4.

6. A method for forming a complex comprising the step of contacting the Ig binding moiety of claim 1 or 2 with a pharmaceutically active moiety comprising a $C_H1$ of an Ig molecule.

* * * * *

UNITED STATES PATENT AND TRADEMARK OFFICE
CERTIFICATE OF CORRECTION

PATENT NO. : 10,428,120 B2  
APPLICATION NO. : 15/410363  
DATED : October 1, 2019  
INVENTOR(S) : Roland Kontermann et al.

It is certified that error appears in the above-identified patent and that said Letters Patent is hereby corrected as shown below:

On the Title Page

At item (72), Line 1, "Nurtingen (DE);" should be -- Nürtingen (DE); --.

At item (72), Line 3, "Schomdorf (DE)" should be -- Schorndorf (DE) --.

In the Claims

At Column 67, Line 62, "TTYKLVINGKTLK" should be -- TYKLVINGKTLK --.

At Column 68, Line 58, "TTYKLVINGKTLK" should be -- TYKLVINGKTLK --.

Signed and Sealed this  
Seventh Day of July, 2020

Andrei Iancu  
*Director of the United States Patent and Trademark Office*

SEQUENCE LISTING

```
<160> NUMBER OF SEQ ID NOS: 18

<210> SEQ ID NO 1
<211> LENGTH: 55
<212> TYPE: PRT
<213> ORGANISM: Peptostreptococcus magnus

<400> SEQUENCE: 1

Thr Tyr Lys Leu Val Ile Asn Gly Lys Thr Leu Lys Gly Glu Thr Thr
1               5                   10                  15

Thr Lys Ala Val Asp Ala Glu Thr Ala Glu Lys Ala Phe Lys Gln Tyr
            20                  25                  30

Ala Asn Asp Asn Gly Val Asp Gly Val Trp Thr Tyr Asp Asp Ala Thr
        35                  40                  45

Lys Thr Phe Thr Val Thr Glu
    50                  55

<210> SEQ ID NO 2
<211> LENGTH: 55
<212> TYPE: PRT
<213> ORGANISM: Peptostreptococcus magnus

<400> SEQUENCE: 2

Thr Tyr Lys Leu Val Ile Asn Gly Lys Ala Leu Ala Gly Ala Thr Thr
1               5                   10                  15

Thr Lys Ala Val Asp Ala Glu Thr Ala Glu Lys Ala Phe Lys Gln Tyr
            20                  25                  30

Ala Asn Asp Asn Gly Val Asp Gly Val Trp Thr Tyr Asp Asp Ala Thr
        35                  40                  45

Lys Thr Phe Thr Val Thr Glu
    50                  55

<210> SEQ ID NO 3
<211> LENGTH: 55
<212> TYPE: PRT
<213> ORGANISM: Peptostreptococcus magnus

<400> SEQUENCE: 3

Thr Tyr Lys Leu Val Ile Asn Gly Lys Thr Leu Lys Gly Glu Thr Thr
1               5                   10                  15

Thr Lys Ala Val Asp Ala Glu Thr Ala Ala Ala Ala Phe Ala Gln Tyr
            20                  25                  30

Ala Asn Asp Asn Gly Val Asp Gly Val Trp Thr Tyr Asp Asp Ala Thr
        35                  40                  45

Lys Thr Phe Thr Val Thr Glu
    50                  55
```

<210> SEQ ID NO 4
<211> LENGTH: 330
<212> TYPE: PRT
<213> ORGANISM: Homo sapiens
<220> FEATURE:
<221> NAME/KEY: BINDING
<222> LOCATION: (5)..(10)
<223> OTHER INFORMATION: SpG-C3 binding epitope
<220> FEATURE:
<221> NAME/KEY: BINDING
<222> LOCATION: (90)..(97)
<223> OTHER INFORMATION: SpG-C3 binding epitope

<400> SEQUENCE: 4

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```

```
<210> SEQ ID NO 5
<211> LENGTH: 326
<212> TYPE: PRT
<213> ORGANISM: Homo sapiens
<220> FEATURE:
<221> NAME/KEY: BINDING
<222> LOCATION: (5)..(10)
<223> OTHER INFORMATION: SpG-C3 binding epitope
<220> FEATURE:
<221> NAME/KEY: BINDING
<222> LOCATION: (90)..(97)
<223> OTHER INFORMATION: SpG-C3 binding epitope

<400> SEQUENCE: 5

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ser Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly Lys
                325
```

```
<210> SEQ ID NO 6
<211> LENGTH: 377
<212> TYPE: PRT
<213> ORGANISM: Homo sapiens
<220> FEATURE:
<221> NAME/KEY: BINDING
<222> LOCATION: (5)..(10)
<223> OTHER INFORMATION: SpG-C3 binding epitope
<220> FEATURE:
<221> NAME/KEY: BINDING
<222> LOCATION: (90)..(97)
<223> OTHER INFORMATION: SpG-C3 binding epitope

<400> SEQUENCE: 6

Ala Ser Thr Lys Gly Pro Ser Val Phe Pro Leu Ala Pro Cys Ser Arg
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Thr Cys Asn Val Asn His Lys Pro Ser Asn Thr Lys Val Asp Lys
                85                  90                  95

Arg Val Glu Leu Lys Thr Pro Leu Gly Asp Thr Thr His Thr Cys Pro
            100                 105                 110

Arg Cys Pro Glu Pro Lys Ser Cys Asp Thr Pro Pro Pro Cys Pro Arg
        115                 120                 125

Cys Pro Glu Pro Lys Ser Cys Asp Thr Pro Pro Pro Cys Pro Arg Cys
    130                 135                 140

Pro Glu Pro Lys Ser Cys Asp Thr Pro Pro Pro Cys Pro Arg Cys Pro
145                 150                 155                 160

Ala Pro Glu Leu Leu Gly Gly Pro Ser Val Phe Leu Phe Pro Pro Lys
                165                 170                 175

Pro Lys Asp Thr Leu Met Ile Ser Arg Thr Pro Glu Val Thr Cys Val
            180                 185                 190

Val Val Asp Val Ser His Glu Asp Pro Glu Val Gln Phe Lys Trp Tyr
        195                 200                 205

Val Asp Gly Val Glu Val His Asn Ala Lys Thr Lys Pro Arg Glu Glu
    210                 215                 220

Gln Tyr Asn Ser Thr Phe Arg Val Val Ser Val Leu Thr Val Leu His
225                 230                 235                 240

Gln Asp Trp Leu Asn Gly Lys Glu Tyr Lys Cys Lys Val Ser Asn Lys
                245                 250                 255

Ala Leu Pro Ala Pro Ile Glu Lys Thr Ile Ser Lys Thr Lys Gly Gln
            260                 265                 270

Pro Arg Glu Pro Gln Val Tyr Thr Leu Pro Pro Ser Arg Glu Glu Met
        275                 280                 285

Thr Lys Asn Gln Val Ser Leu Thr Cys Leu Val Lys Gly Phe Tyr Pro
    290                 295                 300

Ser Asp Ile Ala Val Glu Trp Glu Ser Ser Gly Gln Pro Glu Asn Asn
305                 310                 315                 320

Tyr Asn Thr Thr Pro Pro Met Leu Asp Ser Asp Gly Ser Phe Phe Leu
                325                 330                 335
```

-continued

```
Tyr Ser Lys Leu Thr Val Asp Lys Ser Arg Trp Gln Gln Gly Asn Ile
            340                 345                 350

Phe Ser Cys Ser Val Met His Glu Ala Leu His Asn Arg Phe Thr Gln
            355                 360                 365

Lys Ser Leu Ser Leu Ser Pro Gly Lys
            370                 375

<210> SEQ ID NO 7
<211> LENGTH: 327
<212> TYPE: PRT
<213> ORGANISM: Homo sapiens
<220> FEATURE:
<221> NAME/KEY: BINDING
<222> LOCATION: (5)..(10)
<223> OTHER INFORMATION: SpG-C3 binding epitope
<220> FEATURE:
<221> NAME/KEY: BINDING
<222> LOCATION: (90)..(97)
<223> OTHER INFORMATION: SpG-C3 binding epitope

<400> SEQUENCE: 7

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285
```

```
Arg Leu Thr Val Asp Lys Ser Arg Trp Gln Glu Gly Asn Val Phe Ser
            290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 8
<211> LENGTH: 324
<212> TYPE: PRT
<213> ORGANISM: Mus musculus
<220> FEATURE:
<221> NAME/KEY: BINDING
<222> LOCATION: (5)..(10)
<223> OTHER INFORMATION: SpG-C3 binding epitope
<220> FEATURE:
<221> NAME/KEY: BINDING
<222> LOCATION: (89)..(96)
<223> OTHER INFORMATION: SpG-C3 binding epitope

<400> SEQUENCE: 8

Ala Lys Thr Thr Pro Pro Ser Val Tyr Pro Leu Ala Pro Gly Ser Ala
1               5                   10                  15

Ala Gln Thr Asn Ser Met Val Thr Leu Gly Cys Leu Val Lys Gly Tyr
            20                  25                  30

Phe Pro Glu Pro Val Thr Val Thr Trp Asn Ser Gly Ser Leu Ser Ser
        35                  40                  45

Gly Val His Thr Phe Pro Ala Val Leu Gln Ser Asp Leu Tyr Thr Leu
    50                  55                  60

Ser Ser Ser Val Thr Val Pro Ser Ser Pro Arg Pro Ser Glu Thr Val
65                  70                  75                  80

Thr Cys Asn Val Ala His Pro Ala Ser Ser Thr Lys Val Asp Lys Lys
                85                  90                  95

Ile Val Pro Arg Asp Cys Gly Cys Lys Pro Cys Ile Cys Thr Val Pro
            100                 105                 110

Glu Val Ser Ser Val Phe Ile Phe Pro Pro Lys Pro Lys Asp Val Leu
        115                 120                 125

Thr Ile Thr Leu Thr Pro Lys Val Thr Cys Val Val Val Asp Ile Ser
    130                 135                 140

Lys Asp Asp Pro Glu Val Gln Phe Ser Trp Phe Val Asp Asp Val Glu
145                 150                 155                 160

Val His Thr Ala Gln Thr Gln Pro Arg Glu Glu Gln Phe Asn Ser Thr
                165                 170                 175

Phe Arg Ser Val Ser Glu Leu Pro Ile Met His Gln Asp Trp Leu Asn
            180                 185                 190

Gly Lys Glu Phe Lys Cys Arg Val Asn Ser Ala Ala Phe Pro Ala Pro
        195                 200                 205

Ile Glu Lys Thr Ile Ser Lys Thr Lys Gly Arg Pro Lys Ala Pro Gln
    210                 215                 220

Val Tyr Thr Ile Pro Pro Lys Glu Gln Met Ala Lys Asp Lys Val
225                 230                 235                 240

Ser Leu Thr Cys Met Ile Thr Asp Phe Phe Pro Glu Asp Ile Thr Val
                245                 250                 255

Glu Trp Gln Trp Asn Gly Gln Pro Ala Glu Asn Tyr Lys Asn Thr Gln
            260                 265                 270

Pro Ile Met Asn Thr Asn Gly Ser Tyr Phe Val Tyr Ser Lys Leu Asn
        275                 280                 285
```

```
Val Gln Lys Ser Asn Trp Glu Ala Gly Asn Thr Phe Thr Cys Ser Val
        290                 295                 300

Leu His Glu Gly Leu His Asn His His Thr Glu Lys Ser Leu Ser His
305                 310                 315                 320

Ser Pro Gly Lys
```

<210> SEQ ID NO 9
<211> LENGTH: 330
<212> TYPE: PRT
<213> ORGANISM: Mus musculus
<220> FEATURE:
<221> NAME/KEY: BINDING
<222> LOCATION: (5)..(10)
<223> OTHER INFORMATION: SpG-C3 binding epitope
<220> FEATURE:
<221> NAME/KEY: BINDING
<222> LOCATION: (89)..(96)
<223> OTHER INFORMATION: SpG-C3 binding epitope

<400> SEQUENCE: 9

```
Ala Lys Thr Thr Ala Pro Ser Val Tyr Pro Leu Ala Pro Val Cys Gly
1               5                   10                  15

Asp Thr Thr Gly Ser Ser Val Thr Leu Gly Cys Leu Val Lys Gly Tyr
            20                  25                  30

Phe Pro Glu Pro Val Thr Leu Thr Trp Asn Ser Gly Ser Leu Ser Ser
        35                  40                  45

Gly Val His Thr Phe Pro Ala Val Leu Gln Ser Asp Leu Tyr Thr Leu
    50                  55                  60

Ser Ser Ser Val Thr Val Thr Ser Ser Thr Trp Pro Ser Gln Ser Ile
65                  70                  75                  80

Thr Cys Asn Val Ala His Pro Ala Ser Ser Thr Lys Val Asp Lys Lys
                85                  90                  95

Ile Glu Pro Arg Gly Pro Thr Ile Lys Pro Cys Pro Pro Cys Lys Cys
            100                 105                 110

Pro Ala Pro Asn Leu Leu Gly Gly Pro Ser Val Phe Ile Phe Pro Pro
        115                 120                 125

Lys Ile Lys Asp Val Leu Met Ile Ser Leu Ser Pro Ile Val Thr Cys
130                 135                 140

Val Val Val Asp Val Ser Glu Asp Asp Pro Asp Val Gln Ile Ser Trp
145                 150                 155                 160

Phe Val Asn Asn Val Glu Val His Thr Ala Gln Thr Gln Thr His Arg
                165                 170                 175

Glu Asp Tyr Asn Ser Thr Leu Arg Val Val Ser Ala Leu Pro Ile Gln
            180                 185                 190

His Gln Asp Trp Met Ser Gly Lys Glu Phe Lys Cys Lys Val Asn Asn
        195                 200                 205

Lys Asp Leu Pro Ala Pro Ile Glu Arg Thr Ile Ser Lys Pro Lys Gly
    210                 215                 220

Ser Val Arg Ala Pro Gln Val Tyr Val Leu Pro Pro Pro Glu Glu Glu
225                 230                 235                 240

Met Thr Lys Lys Gln Val Thr Leu Thr Cys Met Val Thr Asp Phe Met
                245                 250                 255

Pro Glu Asp Ile Tyr Val Glu Trp Thr Asn Asn Gly Lys Thr Glu Leu
            260                 265                 270

Asn Tyr Lys Asn Thr Glu Pro Val Leu Asp Ser Asp Gly Ser Tyr Phe
        275                 280                 285
```

-continued

```
Met Tyr Ser Lys Leu Arg Val Glu Lys Lys Asn Trp Val Glu Arg Asn
290                 295                 300
Ser Tyr Ser Cys Ser Val Val His Glu Gly Leu His Asn His His Thr
305                 310                 315                 320
Thr Lys Ser Phe Ser Arg Thr Pro Gly Lys
            325                 330

<210> SEQ ID NO 10
<211> LENGTH: 335
<212> TYPE: PRT
<213> ORGANISM: Mus musculus
<220> FEATURE:
<221> NAME/KEY: BINDING
<222> LOCATION: (4)..(9)
<223> OTHER INFORMATION: SpG-C3 binding epitope
<220> FEATURE:
<221> NAME/KEY: BINDING
<222> LOCATION: (88)..(95)
<223> OTHER INFORMATION: SpG-C3 binding epitope

<400> SEQUENCE: 10

Lys Thr Thr Pro Pro Ser Val Tyr Pro Leu Ala Pro Gly Cys Gly Asp
1               5                   10                  15
Thr Thr Gly Ser Ser Val Thr Leu Gly Cys Leu Val Lys Gly Tyr Phe
            20                  25                  30
Pro Glu Ser Val Thr Val Thr Trp Asn Ser Gly Ser Leu Ser Ser Ser
        35                  40                  45
Val His Thr Phe Pro Ala Leu Leu Gln Ser Gly Leu Tyr Thr Met Ser
    50                  55                  60
Ser Ser Val Thr Val Pro Ser Ser Thr Trp Pro Ser Gln Thr Val Thr
65                  70                  75                  80
Cys Ser Val Ala His Pro Ala Ser Ser Thr Thr Val Asp Lys Lys Leu
                85                  90                  95
Glu Pro Ser Gly Pro Ile Ser Thr Ile Asn Pro Cys Pro Pro Cys Lys
            100                 105                 110
Glu Cys His Lys Cys Pro Ala Pro Asn Leu Glu Gly Gly Pro Ser Val
        115                 120                 125
Phe Ile Phe Pro Pro Asn Ile Lys Asp Val Leu Met Ile Ser Leu Thr
    130                 135                 140
Pro Lys Val Thr Cys Val Val Asp Val Ser Glu Asp Asp Pro Asp
145                 150                 155                 160
Val Gln Ile Ser Trp Phe Val Asn Asn Val Glu Val His Thr Ala Gln
                165                 170                 175
Thr Gln Thr His Arg Glu Asp Tyr Asn Ser Thr Ile Arg Val Val Ser
            180                 185                 190
Thr Leu Pro Ile Gln His Gln Asp Trp Met Ser Gly Lys Glu Phe Lys
        195                 200                 205
Cys Lys Val Asn Asn Lys Asp Leu Pro Ser Pro Ile Glu Arg Thr Ile
    210                 215                 220
Ser Lys Ile Lys Gly Leu Val Arg Ala Pro Gln Val Tyr Ile Leu Pro
225                 230                 235                 240
Pro Pro Ala Glu Gln Leu Ser Arg Lys Asp Val Ser Leu Thr Cys Leu
                245                 250                 255
Val Val Gly Phe Asn Pro Gly Asp Ile Ser Val Glu Trp Thr Ser Asn
            260                 265                 270
Gly His Thr Glu Glu Asn Tyr Lys Asp Thr Ala Pro Val Leu Asp Ser
        275                 280                 285
```

Asp Gly Ser Tyr Phe Ile Tyr Ser Lys Leu Asn Met Lys Thr Ser Lys
    290                 295                 300

Trp Glu Lys Thr Asp Ser Phe Ser Cys Asn Val Arg His Glu Gly Leu
305                 310                 315                 320

Lys Asn Tyr Tyr Leu Lys Lys Thr Ile Ser Arg Ser Pro Gly Lys
                325                 330                 335

<210> SEQ ID NO 11
<211> LENGTH: 398
<212> TYPE: PRT
<213> ORGANISM: Mus musculus
<220> FEATURE:
<221> NAME/KEY: BINDING
<222> LOCATION: (4)..(9)
<223> OTHER INFORMATION: SpG-C3 binding epitope
<220> FEATURE:
<221> NAME/KEY: BINDING
<222> LOCATION: (88)..(95)
<223> OTHER INFORMATION: SpG-C3 binding epitope

<400> SEQUENCE: 11

Thr Thr Thr Ala Pro Ser Val Tyr Pro Leu Val Pro Gly Cys Ser Asp
1               5                   10                  15

Thr Ser Gly Ser Ser Val Thr Leu Gly Cys Leu Val Lys Gly Tyr Phe
                20                  25                  30

Pro Glu Pro Val Thr Val Lys Trp Asn Tyr Gly Ala Leu Ser Ser Gly
            35                  40                  45

Val Arg Thr Val Ser Ser Val Leu Gln Ser Gly Phe Tyr Ser Leu Ser
        50                  55                  60

Ser Leu Val Thr Val Pro Ser Ser Thr Trp Pro Ser Gln Thr Val Ile
65                  70                  75                  80

Cys Asn Val Ala His Pro Ala Ser Lys Thr Glu Leu Ile Lys Arg Ile
                85                  90                  95

Glu Pro Arg Ile Pro Lys Pro Ser Thr Pro Pro Gly Ser Ser Cys Pro
            100                 105                 110

Pro Gly Asn Ile Leu Gly Gly Pro Ser Val Phe Ile Phe Pro Pro Lys
        115                 120                 125

Pro Lys Asp Ala Leu Met Ile Ser Leu Thr Pro Lys Val Thr Cys Val
    130                 135                 140

Val Val Asp Val Ser Glu Asp Asp Pro Asp Val His Val Ser Trp Phe
145                 150                 155                 160

Val Asp Asn Lys Glu Val His Thr Ala Trp Thr Gln Pro Arg Glu Ala
                165                 170                 175

Gln Tyr Asn Ser Thr Phe Arg Val Val Ser Ala Leu Pro Ile Gln His
            180                 185                 190

Gln Asp Trp Met Arg Gly Lys Glu Phe Lys Cys Lys Val Asn Asn Lys
        195                 200                 205

Ala Leu Pro Ala Pro Ile Glu Arg Thr Ile Ser Lys Pro Lys Gly Arg
    210                 215                 220

Ala Gln Thr Pro Gln Val Tyr Thr Ile Pro Pro Arg Glu Gln Met
225                 230                 235                 240

Ser Lys Lys Lys Val Ser Leu Thr Cys Leu Val Thr Asn Phe Phe Ser
                245                 250                 255

Glu Ala Ile Ser Val Glu Trp Glu Arg Asn Gly Glu Leu Glu Gln Asp
            260                 265                 270

Tyr Lys Asn Thr Pro Pro Ile Leu Asp Ser Asp Gly Thr Tyr Phe Leu
        275                 280                 285

```
Tyr Ser Lys Leu Thr Val Asp Thr Asp Ser Trp Leu Gln Gly Glu Ile
        290                 295                 300

Phe Thr Cys Ser Val Val His Glu Ala Leu His Asn His His Thr Gln
305                 310                 315                 320

Lys Asn Leu Ser Arg Ser Pro Glu Leu Glu Leu Asn Glu Thr Cys Ala
                325                 330                 335

Glu Ala Gln Asp Gly Glu Leu Asp Gly Leu Trp Thr Thr Ile Thr Ile
            340                 345                 350

Phe Ile Ser Leu Phe Leu Leu Ser Val Cys Tyr Ser Ala Ser Val Thr
                355                 360                 365

Leu Phe Lys Val Lys Trp Ile Phe Ser Ser Val Val Gln Val Lys Gln
370                 375                 380

Thr Ala Ile Pro Asp Tyr Arg Asn Met Ile Gly Gln Gly Ala
385                 390                 395

<210> SEQ ID NO 12
<211> LENGTH: 326
<212> TYPE: PRT
<213> ORGANISM: Rattus norvegicus
<220> FEATURE:
<221> NAME/KEY: BINDING
<222> LOCATION: (5)..(10)
<223> OTHER INFORMATION: SpG-C3 binding epitope
<220> FEATURE:
<221> NAME/KEY: BINDING
<222> LOCATION: (89)..(96)
<223> OTHER INFORMATION: SpG-C3 binding epitope

<400> SEQUENCE: 12

Ala Glu Thr Thr Ala Pro Ser Val Tyr Pro Leu Ala Pro Gly Thr Ala
1               5                   10                  15

Leu Lys Ser Asn Ser Met Val Thr Leu Gly Cys Leu Val Lys Gly Tyr
            20                  25                  30

Phe Pro Glu Pro Val Thr Val Thr Trp Asn Ser Gly Ala Leu Ser Ser
        35                  40                  45

Gly Val His Thr Phe Pro Ala Val Leu Gln Ser Gly Leu Tyr Thr Leu
    50                  55                  60

Thr Ser Ser Val Thr Val Pro Ser Ser Thr Trp Pro Ser Gln Thr Val
65                  70                  75                  80

Thr Cys Asn Val Ala His Pro Ala Ser Ser Thr Lys Val Asp Lys Lys
                85                  90                  95

Ile Val Pro Arg Asn Cys Gly Gly Asp Cys Lys Pro Cys Ile Cys Thr
            100                 105                 110

Gly Ser Glu Val Ser Ser Val Phe Ile Phe Pro Pro Lys Pro Lys Asp
        115                 120                 125

Val Leu Thr Ile Thr Leu Thr Pro Lys Val Thr Cys Val Val Val Asp
    130                 135                 140

Ile Ser Gln Asp Asp Pro Glu Val His Phe Ser Trp Phe Val Asp Asp
145                 150                 155                 160

Val Glu Val His Thr Ala Gln Thr Arg Pro Pro Glu Glu Gln Phe Asn
                165                 170                 175

Ser Thr Phe Arg Ser Val Ser Glu Leu Pro Ile Leu His Gln Asp Trp
            180                 185                 190

Leu Asn Gly Arg Thr Phe Arg Cys Lys Val Thr Ser Ala Ala Phe Pro
        195                 200                 205

Ser Pro Ile Glu Lys Thr Ile Ser Lys Pro Glu Gly Arg Thr Gln Val
    210                 215                 220
```

```
Pro His Val Tyr Thr Met Ser Pro Thr Lys Glu Glu Met Thr Gln Asn
225                 230                 235                 240

Glu Val Ser Ile Thr Cys Met Val Lys Gly Phe Tyr Pro Pro Asp Ile
            245                 250                 255

Tyr Val Glu Trp Gln Met Asn Gly Gln Pro Gln Glu Asn Tyr Lys Asn
        260                 265                 270

Thr Pro Pro Thr Met Asp Thr Asp Gly Ser Tyr Phe Leu Tyr Ser Lys
    275                 280                 285

Leu Asn Val Lys Lys Glu Lys Trp Gln Gln Gly Asn Thr Phe Thr Cys
    290                 295                 300

Ser Val Leu His Glu Gly Leu His Asn His His Thr Glu Lys Ser Leu
305                 310                 315                 320

Ser His Ser Pro Gly Lys
                325

<210> SEQ ID NO 13
<211> LENGTH: 343
<212> TYPE: PRT
<213> ORGANISM: Artificial Sequence
<220> FEATURE:
<223> OTHER INFORMATION: ScFv-SpG-C3 (anti-CEA) protein

<400> SEQUENCE: 13

Met Glu Thr Asp Thr Leu Leu Leu Trp Val Leu Leu Leu Trp Val Pro
1               5                   10                  15

Gly Ser Thr Gly Asp Ala Ala Gln Pro Ala Met Ala Gln Val Lys Leu
            20                  25                  30

Gln Gln Ser Gly Ala Glu Leu Val Arg Ser Gly Thr Ser Val Lys Leu
        35                  40                  45

Ser Cys Thr Ala Ser Gly Phe Asn Ile Lys Asp Ser Tyr Met His Trp
    50                  55                  60

Leu Arg Gln Gly Pro Glu Gln Gly Leu Glu Trp Ile Gly Trp Ile Asp
65                  70                  75                  80

Pro Glu Asn Gly Asp Thr Glu Tyr Ala Pro Lys Phe Gln Gly Lys Ala
                85                  90                  95

Thr Phe Thr Thr Asp Thr Ser Ser Asn Thr Ala Tyr Leu Gln Leu Ser
            100                 105                 110

Ser Leu Thr Ser Glu Asp Thr Ala Val Tyr Tyr Cys Asn Glu Gly Thr
        115                 120                 125

Pro Thr Gly Pro Tyr Tyr Phe Asp Tyr Trp Gly Gln Gly Thr Thr Val
    130                 135                 140

Thr Val Ser Ser Gly Gly Gly Gly Ser Gly Gly Gly Gly Ser Gly Gly
145                 150                 155                 160

Gly Gly Ser Asp Ile Glu Leu Thr Gln Ser Pro Ala Ile Met Ser Ala
                165                 170                 175

Ser Pro Gly Glu Lys Val Thr Ile Thr Cys Ser Ala Ser Ser Ser Val
            180                 185                 190

Ser Tyr Met His Trp Phe Gln Gln Lys Pro Gly Thr Ser Pro Lys Leu
        195                 200                 205

Trp Ile Tyr Ser Thr Ser Asn Leu Ala Ser Gly Val Pro Ala Arg Phe
    210                 215                 220

Ser Gly Ser Gly Ser Gly Thr Ser Tyr Ser Leu Thr Ile Ser Arg Met
225                 230                 235                 240

Glu Ala Glu Asp Ala Ala Thr Tyr Tyr Cys Gln Gln Arg Ser Ser Tyr
                245                 250                 255
```

```
Pro Leu Thr Phe Gly Ala Gly Thr Lys Leu Glu Leu Lys Arg Ala Ala
            260                 265                 270

Ala Gly Gly Ser Gly Gly Thr Thr Tyr Lys Leu Val Ile Asn Gly Lys
        275                 280                 285

Thr Leu Lys Gly Glu Thr Thr Thr Lys Ala Val Asp Ala Glu Thr Ala
    290                 295                 300

Glu Lys Ala Phe Lys Gln Tyr Ala Asn Asp Asn Gly Val Asp Gly Val
305                 310                 315                 320

Trp Thr Tyr Asp Asp Ala Thr Lys Thr Phe Thr Val Thr Glu Gly Gly
                325                 330                 335

Ser His His His His His His
            340

<210> SEQ ID NO 14
<211> LENGTH: 583
<212> TYPE: PRT
<213> ORGANISM: Artificial Sequence
<220> FEATURE:
<223> OTHER INFORMATION: scDb-SpG-C3 (anti-CEA x anti-CD3) protein

<400> SEQUENCE: 14

Met Glu Thr Asp Thr Leu Leu Leu Trp Val Leu Leu Leu Trp Val Pro
1               5                   10                  15

Gly Ser Thr Gly Asp Ala Ala Gln Pro Ala Met Ala Gln Val Lys Leu
            20                  25                  30

Gln Gln Ser Gly Ala Glu Leu Val Arg Ser Gly Thr Ser Val Lys Leu
        35                  40                  45

Ser Cys Thr Ala Ser Gly Phe Asn Ile Lys Asp Ser Tyr Met His Trp
    50                  55                  60

Leu Arg Gln Gly Pro Glu Gln Gly Leu Glu Trp Ile Gly Trp Ile Asp
65                  70                  75                  80

Pro Glu Asn Gly Asp Thr Glu Tyr Ala Pro Lys Phe Gln Gly Lys Ala
                85                  90                  95

Thr Phe Thr Thr Asp Thr Ser Ser Asn Thr Ala Tyr Leu Gln Leu Ser
            100                 105                 110

Ser Leu Thr Ser Glu Asp Thr Ala Val Tyr Tyr Cys Asn Glu Gly Thr
        115                 120                 125

Pro Thr Gly Pro Tyr Tyr Phe Asp Tyr Trp Gly Gln Gly Thr Thr Val
    130                 135                 140

Thr Val Ser Ser Gly Gly Gly Gly Ser Asp Ile Gln Met Thr Gln Ser
145                 150                 155                 160

Pro Ser Ser Leu Ser Ala Ser Val Gly Asp Arg Val Thr Ile Thr Cys
                165                 170                 175

Arg Ala Ser Gln Asp Ile Arg Asn Tyr Leu Asn Trp Tyr Gln Gln Lys
            180                 185                 190

Pro Gly Lys Ala Pro Lys Leu Leu Ile Tyr Tyr Thr Ser Arg Leu Glu
        195                 200                 205

Ser Gly Val Pro Ser Arg Phe Ser Gly Ser Gly Ser Gly Thr Asp Tyr
    210                 215                 220

Thr Leu Thr Ile Ser Ser Leu Gln Pro Glu Asp Phe Ala Thr Tyr Tyr
225                 230                 235                 240

Cys Gln Gln Gly Asn Thr Leu Pro Trp Thr Phe Gly Gln Gly Thr Lys
                245                 250                 255

Val Glu Ile Lys Arg Gly Gly Gly Ser Gly Gly Arg Ala Ser Gly
            260                 265                 270
```

Gly Gly Gly Ser Glu Val Gln Leu Val Glu Ser Gly Gly Leu Val
            275                 280                 285

Gln Pro Gly Gly Ser Leu Arg Leu Ser Cys Ala Ala Ser Gly Tyr Ser
290                 295                 300

Phe Thr Gly Tyr Thr Met Asn Trp Val Arg Gln Ala Pro Gly Lys Gly
305                 310                 315                 320

Leu Glu Trp Val Ala Leu Ile Asn Pro Tyr Lys Gly Val Ser Thr Tyr
                325                 330                 335

Asn Gln Lys Phe Lys Asp Arg Phe Thr Ile Ser Val Asp Lys Ser Lys
            340                 345                 350

Asn Thr Ala Tyr Leu Gln Met Asn Ser Leu Arg Ala Glu Asp Thr Ala
        355                 360                 365

Val Tyr Tyr Cys Ala Arg Ser Gly Tyr Tyr Gly Asp Ser Asp Trp Tyr
370                 375                 380

Phe Asp Val Trp Gly Gln Gly Thr Leu Val Thr Val Ser Ser Gly Gly
385                 390                 395                 400

Gly Gly Ser Asp Ile Glu Leu Thr Gln Ser Pro Ala Ile Met Ser Ala
                405                 410                 415

Ser Pro Gly Glu Lys Val Thr Ile Thr Cys Ser Ala Ser Ser Ser Val
            420                 425                 430

Ser Tyr Met His Trp Phe Gln Gln Lys Pro Gly Thr Ser Pro Lys Leu
        435                 440                 445

Trp Ile Tyr Ser Thr Ser Asn Leu Ala Ser Gly Val Pro Ala Arg Phe
    450                 455                 460

Ser Gly Ser Gly Ser Gly Thr Ser Tyr Ser Leu Thr Ile Ser Arg Met
465                 470                 475                 480

Glu Ala Glu Asp Ala Ala Thr Tyr Tyr Cys Gln Gln Arg Ser Ser Tyr
                485                 490                 495

Pro Leu Thr Phe Gly Ala Gly Thr Lys Leu Glu Leu Lys Arg Ala Ala
            500                 505                 510

Ala Gly Gly Ser Gly Gly Thr Thr Tyr Lys Leu Val Ile Asn Gly Lys
        515                 520                 525

Thr Leu Lys Gly Glu Thr Thr Thr Lys Ala Val Asp Ala Glu Thr Ala
    530                 535                 540

Glu Lys Ala Phe Lys Gln Tyr Ala Asn Asp Asn Gly Val Asp Gly Val
545                 550                 555                 560

Trp Thr Tyr Asp Asp Ala Thr Lys Thr Phe Thr Val Thr Glu Gly Gly
                565                 570                 575

Ser His His His His His His
            580

<210> SEQ ID NO 15
<211> LENGTH: 925
<212> TYPE: PRT
<213> ORGANISM: Artificial Sequence
<220> FEATURE:
<223> OTHER INFORMATION: SpG-C3-Db-scTRAIL (anti-human EGFR) protein

<400> SEQUENCE: 15

Met Asp Trp Thr Trp Arg Val Phe Cys Leu Leu Ala Val Ala Pro Gly
1               5                   10                  15

Ala His Ser Leu Glu Ala Ser Asp Tyr Lys Asp Asp Asp Asp Lys Gly
            20                  25                  30

Ala Thr Thr Tyr Lys Leu Val Ile Asn Gly Lys Thr Leu Lys Gly Glu
        35                  40                  45

```
Thr Thr Thr Lys Ala Val Asp Ala Glu Thr Ala Glu Lys Ala Phe Lys
    50              55                  60

Gln Tyr Ala Asn Asp Asn Gly Val Asp Gly Val Trp Thr Tyr Asp Asp
 65              70                  75                      80

Ala Thr Lys Thr Phe Thr Val Thr Glu Gly Ser Gly Gly Gly
                 85                  90                  95

Ser Gly Gly Glu Val Gln Leu Val Glu Ser Gly Gly Leu Val Gln
            100             105                 110

Pro Gly Gly Ser Leu Arg Leu Ser Cys Ala Ala Ser Gly Phe Ser Leu
            115             120             125

Thr Asn Tyr Gly Val His Trp Val Arg Gln Ala Pro Gly Lys Gly Leu
130             135                 140

Glu Trp Leu Gly Val Ile Trp Ser Gly Gly Asn Thr Asp Tyr Asn Thr
145             150                 155                 160

Pro Phe Thr Ser Arg Phe Thr Ile Ser Arg Asp Asn Ser Lys Asn Thr
                165                 170                 175

Leu Tyr Leu Gln Met Asn Ser Leu Arg Ala Glu Asp Thr Ala Val Tyr
            180                 185                 190

Tyr Cys Ala Arg Ala Leu Thr Tyr Tyr Asp Tyr Glu Phe Ala Tyr Trp
        195                 200                 205

Gly Gln Gly Thr Thr Val Thr Val Ser Ser Gly Gly Gly Gly Ser Asp
    210                 215                 220

Ile Gln Leu Thr Gln Ser Pro Ser Phe Leu Ser Ala Ser Val Gly Asp
225             230                 235                 240

Arg Val Thr Ile Thr Cys Arg Ala Ser Gln Ser Ile Gly Thr Asn Ile
                245                 250                 255

His Trp Tyr Gln Gln Lys Pro Gly Lys Ala Pro Lys Leu Leu Ile Lys
            260                 265                 270

Tyr Ala Ser Glu Ser Ile Ser Gly Val Pro Ser Arg Phe Ser Gly Ser
        275                 280                 285

Gly Ser Gly Thr Glu Phe Thr Leu Thr Ile Ser Ser Leu Gln Pro Glu
    290                 295                 300

Asp Phe Ala Thr Tyr Tyr Cys Gln Gln Asn Asn Asn Trp Pro Thr Thr
305             310                 315                 320

Phe Gly Ala Gly Thr Lys Leu Glu Ile Lys Arg Ala Ala Gly Asn
                325                 330                 335

Gly Thr Ser Asn Gly Thr Ser Glu Phe Thr Arg Gly Thr Ser Glu Glu
            340                 345                 350

Thr Ile Ser Thr Val Gln Glu Lys Gln Gln Asn Ile Ser Pro Leu Val
            355                 360                 365

Arg Glu Arg Gly Pro Gln Arg Val Ala Ala His Ile Thr Gly Thr Arg
370                 375                 380

Gly Arg Ser Asn Thr Leu Ser Ser Pro Asn Ser Lys Asn Glu Lys Ala
385                 390                 395                 400

Leu Gly Arg Lys Ile Asn Ser Trp Glu Ser Ser Arg Ser Gly His Ser
                405                 410                 415

Phe Leu Ser Asn Leu His Leu Arg Asn Gly Glu Leu Val Ile His Glu
            420                 425                 430

Lys Gly Phe Tyr Tyr Ile Tyr Ser Gln Thr Tyr Phe Arg Phe Gln Glu
            435                 440                 445

Glu Ile Lys Glu Asn Thr Lys Asn Asp Lys Gln Met Val Gln Tyr Ile
450                 455                 460

Tyr Lys Tyr Thr Ser Tyr Pro Asp Pro Ile Leu Leu Met Lys Ser Ala
```

```
                465                 470                 475                 480
Arg Asn Ser Cys Trp Ser Lys Asp Ala Glu Tyr Gly Leu Tyr Ser Ile
                    485                 490                 495

Tyr Gln Gly Gly Ile Phe Glu Leu Lys Glu Asn Asp Arg Ile Phe Val
                500                 505                 510

Ser Val Thr Asn Glu His Leu Ile Asp Met Asp His Glu Ala Ser Phe
            515                 520                 525

Phe Gly Ala Phe Leu Val Gly Gly Gly Ser Gly Gly Gly Ser Thr
        530                 535                 540

Ser Glu Glu Thr Ile Ser Thr Val Gln Glu Lys Gln Gln Asn Ile Ser
545                 550                 555                 560

Pro Leu Val Arg Glu Arg Gly Pro Gln Arg Val Ala Ala His Ile Thr
                565                 570                 575

Gly Thr Arg Gly Arg Ser Asn Thr Leu Ser Ser Pro Asn Ser Lys Asn
                580                 585                 590

Glu Lys Ala Leu Gly Arg Lys Ile Asn Ser Trp Glu Ser Ser Arg Ser
            595                 600                 605

Gly His Ser Phe Leu Ser Asn Leu His Leu Arg Asn Gly Glu Leu Val
        610                 615                 620

Ile His Glu Lys Gly Phe Tyr Tyr Ile Tyr Ser Gln Thr Tyr Phe Arg
625                 630                 635                 640

Phe Gln Glu Glu Ile Lys Glu Asn Thr Lys Asn Asp Lys Gln Met Val
                645                 650                 655

Gln Tyr Ile Tyr Lys Tyr Thr Ser Tyr Pro Asp Pro Ile Leu Leu Met
                660                 665                 670

Lys Ser Ala Arg Asn Ser Cys Trp Ser Lys Asp Ala Glu Tyr Gly Leu
            675                 680                 685

Tyr Ser Ile Tyr Gln Gly Gly Ile Phe Glu Leu Lys Glu Asn Asp Arg
        690                 695                 700

Ile Phe Val Ser Val Thr Asn Glu His Leu Ile Asp Met Asp His Glu
705                 710                 715                 720

Ala Ser Phe Phe Gly Ala Phe Leu Val Gly Gly Gly Ser Gly Gly
                725                 730                 735

Gly Ser Thr Ser Glu Glu Thr Ile Ser Thr Val Gln Glu Lys Gln Gln
                740                 745                 750

Asn Ile Ser Pro Leu Val Arg Glu Arg Gly Pro Gln Arg Val Ala Ala
            755                 760                 765

His Ile Thr Gly Thr Arg Gly Arg Ser Asn Thr Leu Ser Ser Pro Asn
        770                 775                 780

Ser Lys Asn Glu Lys Ala Leu Gly Arg Lys Ile Asn Ser Trp Glu Ser
785                 790                 795                 800

Ser Arg Ser Gly His Ser Phe Leu Ser Asn Leu His Leu Arg Asn Gly
                805                 810                 815

Glu Leu Val Ile His Glu Lys Gly Phe Tyr Tyr Ile Tyr Ser Gln Thr
                820                 825                 830

Tyr Phe Arg Phe Gln Glu Glu Ile Lys Glu Asn Thr Lys Asn Asp Lys
            835                 840                 845

Gln Met Val Gln Tyr Ile Tyr Lys Tyr Thr Ser Tyr Pro Asp Pro Ile
        850                 855                 860

Leu Leu Met Lys Ser Ala Arg Asn Ser Cys Trp Ser Lys Asp Ala Glu
865                 870                 875                 880

Tyr Gly Leu Tyr Ser Ile Tyr Gln Gly Gly Ile Phe Glu Leu Lys Glu
                885                 890                 895
```

```
Asn Asp Arg Ile Phe Val Ser Val Thr Asn Glu His Leu Ile Asp Met
            900                 905                 910
Asp His Glu Ala Ser Phe Phe Gly Ala Phe Leu Val Gly
        915                 920                 925

<210> SEQ ID NO 16
<211> LENGTH: 55
<212> TYPE: PRT
<213> ORGANISM: Peptostreptococcus magnus

<400> SEQUENCE: 16

Thr Tyr Lys Leu Ile Leu Asn Gly Lys Thr Leu Lys Gly Glu Thr Thr
1               5                   10                  15
Thr Glu Ala Val Asp Ala Ala Thr Ala Glu Lys Val Phe Lys Gln Tyr
            20                  25                  30
Ala Asn Asp Asn Gly Val Asp Gly Glu Trp Thr Tyr Asp Asp Ala Thr
        35                  40                  45
Lys Thr Phe Thr Val Thr Glu
    50                  55

<210> SEQ ID NO 17
<211> LENGTH: 55
<212> TYPE: PRT
<213> ORGANISM: Peptostreptococcus magnus

<400> SEQUENCE: 17

Thr Tyr Lys Leu Val Ile Asn Gly Lys Thr Leu Lys Gly Glu Thr Thr
1               5                   10                  15
Thr Glu Ala Val Asp Ala Ala Thr Ala Glu Lys Val Phe Lys Gln Tyr
            20                  25                  30
Ala Asn Asp Asn Gly Val Asp Gly Glu Trp Thr Tyr Asp Asp Ala Thr
        35                  40                  45
Lys Thr Phe Thr Val Thr Glu
    50                  55

<210> SEQ ID NO 18
<211> LENGTH: 10
<212> TYPE: PRT
<213> ORGANISM: Artificial Sequence
<220> FEATURE:
<223> OTHER INFORMATION: Linker

<400> SEQUENCE: 18

Gly Gly Ser Gly Gly Gly Gly Ser Gly Gly
1               5                   10
```